(12) United States Patent
Kasus-Jacobi et al.

(10) Patent No.: US 12,241,099 B2
(45) Date of Patent: Mar. 4, 2025

(54) PEPTIDE THERAPEUTICS FOR TREATING ALZHEIMER'S DISEASE AND RELATED CONDITIONS

(71) Applicant: The Board of Regents of the University of Oklahoma, Norman, OK (US)

(72) Inventors: Anne Kasus-Jacobi, Midwest City, OK (US); Heloise Anne Pereira, Edmond, OK (US); Amanda J. Stock, Nottingham, MD (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 1019 days.

(21) Appl. No.: 17/115,321

(22) Filed: Dec. 8, 2020

(65) Prior Publication Data

US 2021/0115426 A1 Apr. 22, 2021

Related U.S. Application Data

(63) Continuation-in-part of application No. PCT/US2019/036281, filed on Jun. 10, 2019.

(60) Provisional application No. 62/682,455, filed on Jun. 8, 2018.

(51) Int. Cl.
| | |
|---|---|
| *C07K 14/00* | (2006.01) |
| *A61K 38/00* | (2006.01) |
| *A61K 38/48* | (2006.01) |
| *A61P 25/28* | (2006.01) |
| *C07K 14/47* | (2006.01) |
| *C12N 9/64* | (2006.01) |
| *C12N 9/96* | (2006.01) |

(52) U.S. Cl.
CPC .......... *C12N 9/6424* (2013.01); *A61K 38/482* (2013.01); *A61K 38/486* (2013.01); *A61P 25/28* (2018.01); *C07K 14/4723* (2013.01); *C12N 9/6448* (2013.01); *C12N 9/96* (2013.01); *C12Y 304/2102* (2013.01); *C12Y 304/21037* (2013.01); *A61K 38/00* (2013.01)

(58) Field of Classification Search
CPC ...... C12N 9/6424; C12N 9/6448; C12N 9/96; A61K 38/482; A61K 38/486; A61K 38/00; A61K 38/48; A61P 25/28; C07K 14/4723; C07K 14/4711; C07K 14/00
See application file for complete search history.

(56) References Cited

U.S. PATENT DOCUMENTS

| | | | |
|---|---|---|---|
| 5,834,290 A | * | 11/1998 | Egelrud .................. A61Q 5/02 435/320.1 |
| 5,837,247 A | | 11/1998 | Oppenhelm et al. |
| 9,096,679 B2 | | 8/2015 | Pereira |
| 9,603,896 B2 | | 3/2017 | Pereira et al. |
| 9,624,283 B2 | | 4/2017 | Pereira et al. |
| 9,862,748 B2 | | 1/2018 | Pereira et al. |
| 2005/0069877 A1 | * | 3/2005 | Gandhi .................. A61P 43/00 435/325 |
| 2006/0008891 A1 | | 1/2006 | Wang et al. |
| 2007/0135341 A1 | | 6/2007 | Pereira et al. |
| 2013/0252901 A1 | | 9/2013 | Mediannikov et al. |
| 2014/0162938 A1 | * | 6/2014 | Pereira .................. A61P 31/00 514/21.3 |
| 2021/0115426 A1 | | 4/2021 | Kasus-Jacobi et al. |

FOREIGN PATENT DOCUMENTS

| | | |
|---|---|---|
| WO | 2014089088 A1 | 6/2014 |
| WO | 2014172747 A1 | 10/2014 |
| WO | 2019237101 A1 | 12/2019 |

OTHER PUBLICATIONS

Rudinger, J., "Characteristics of the amino acids as components of a peptide hormone sequence," Peptide Hormones, JA Parsons, Ed., 1976. pp. 1-7. (Year: 1976).*
Berendsen, HJC, "A Glimpse of the Holy Grail?" Science, 1998, 282: 642-643. (Year: 1998).*
Voet and Voet, Biochemistry, Second Edition, John Wiley & Sons, Inc., 1995, pp. 235-241. (Year: 1995).*
SIGMA, "Designing Custom Peptides," pp. 1-2. Accessed Dec. 16, 2004. (Year: 2004).*
Ngo et al., "Computational Complexity, Protein Structure Prediction, and the Levinthal Paradox," The Protein Folding Problem and Tertiary Structure Prediction, K. Merz Jr. and S. Le Grand Editors, 1994, pp. 491-495. (Year: 1994).*
Bradley et al., "Limits of Cooperativity in a Structurally Modular Protein: Response of the Notch Ankyrin Domain to Analogous Alanine Substitutions in Each Repeat," J. Mol. Biol., 2002, 324: 373-386. (Year: 2002).*
Yampolsky et al., "The Exchangeability of Amino Acids in Proteins," Genetics, 2005, 170: 1459-1472. (Year: 2005).*
Tausch, et al.; "Identification of Human Cathepsin G As a Functional Target of Boswellic Acids from the Anti-Inflammatory Remedy Frankincense"; The Journal of Immunology 183:5 (2009) 3433-3442.
PCT/US2019/036281; "International Search Report and Written Opinion"; International Bureau; Oct. 29, 2019; 11 pages.
PCT/US2021/062308; "International Search Report and Written Opinion"; mailed Jun. 3, 2022; 15 pages.

* cited by examiner

*Primary Examiner* — Julie Ha
(74) *Attorney, Agent, or Firm* — Hall Estill Law Firm

(57) ABSTRACT

Peptide compounds derived from cathepsin G (CG), neutrophil elastase (NE), and cationic antimicrobial protein of 37 kDa (CAP37), and methods of their use in inhibiting and/or reversing polymerization of amyloid β peptide into oligomers and/or fibrils, and/or disaggregating amyloid β plaques, and methods of use of the peptide compounds in treatments of, for example, Alzheimer's disease, cerebral amyloid angiopathy, dementia, and/or neuroinflammation, and/or symptoms thereof are disclosed.

18 Claims, 15 Drawing Sheets

Specification includes a Sequence Listing.

- ◆ Amyloid Beta
- + Fluorescence Background
- ○ Amyloid Beta + 1000 nM CAP37
- △ Amyloid Beta + 10 nM Neutrophil Elastase
- ▽ Amyloid Beta + 10 nM Cathepsin G

PEPTIDE THERAPEUTICS FOR TREATING ALZHEIMER'S DISEASE AND RELATED CONDITIONS

CROSS-REFERENCE TO RELATED APPLICATIONS

This application is a continuation-in-part of International Application No. PCT/US2019/036281, filed Jun. 10, 2019, which claims priority to U.S. Provisional Application No. 62/682,455, filed on Jun. 8, 2018, each of which is expressly incorporated herein by reference in its entirety.

GOVERNMENT SUPPORT

This invention was made with government support under Grant Numbers R21EY026229 and P20GM103640-06 awarded by the National Institutes of Health. The government has certain rights in the invention.

BACKGROUND

Alzheimer's disease (AD) is the most common cause of dementia among people 65 and older and the sixth leading cause of death in the United States. It currently affects ~5 million people, a number that is expected to double during the next 20 years. Currently, AD cannot be cured, prevented, or slowed so there is an important need for the development of efficient therapeutic approaches.

It was previously shown that cationic antimicrobial protein of 37 kDa (CAP37) is significantly up-regulated in neurons and the hippocampus vasculature in patients with AD compared to age-matched controls. It was also shown that CAP37 protein binds and cleaves amyloid beta (amyloid β, or Aβ), the main component of amyloid plaques found in the brain of patients with AD, and that CAP37 protein interacts with the pro-inflammatory receptor for advanced glycation end-products (RAGE). Aβ accumulates in the brain early during the progression of AD and is a key hallmark of AD pathology. As its concentration increases, Aβ polymerizes, first forming soluble oligomers and fibrils, which then precipitate to form insoluble amyloid plaques. Aβ accumulation in the brain can be the result of (1) an increased production from the cleavage of amyloid precursor protein (APP), (2) an increased influx from the blood, and/or (3) a decreased clearance.

RAGE belongs to the immunoglobulin superfamily of transmembrane receptors and mediates pro-inflammatory signals. Aβ (in the form of monomers, oligomers, and fibrils) is a known ligand of RAGE. Other known ligands of RAGE include the advanced glycation end-products (AGEs), S100/calgranulins, and high mobility group box-1 (HMGB 1) protein. RAGE is expressed at low levels in adult tissues, and is up-regulated by a positive feedback loop when concentrations of RAGE ligands increase. RAGE expression is up-regulated in the brain of patients with AD. In AD pathogenesis, RAGE is thought to play a role in mediating the toxic effects of Aβ oligomers and fibrils in neurons and microglial cells. In neurons, RAGE can mediate induction of oxidative stress and hyperphosphorylation of Tau. RAGE also mediates activation of microglial cells, perpetuating the chronic underlying neuroinflammation associated with AD. At the blood-brain-barrier, RAGE activation is thought to participate in the breakdown of the barrier function, another pathological feature associated with AD. Finally, RAGE mediates the influx of Aβ from the circulation into the brain through the transcytosis mechanism.

Previous findings have established that: (1) the expression of CAP37 is increased in neurons of patients with Alzheimer's disease (AD), more so than in patients without diagnosed AD, but of the same age. This established a positive correlation between the amount of CAP37 in the brain and the disease. This was not the case for two closely related proteins neutrophil elastase (NE) and cathepsin G (CG), (2) the regulation of CAP37, NE, and CG expression are generally correlated with the regulation of proteins that serve as ligands for the pro-inflammatory receptor for advanced glycation end-products (RAGE), (3) CAP37 binds to RAGE similarly to the Aβ peptide, a previously known ligand of RAGE, and NE and CG also bind to RAGE, (4) the CAP37-RAGE and NE-RAGE interactions are inhibited by a specific RAGE inhibitor, (5) CAP37, NE and CG bind to Aβ, and (6) CAP37, NE and CG exert protease activities on Aβ and cleave it at several identified cleaving sites.

Both Aβ and RAGE have thus been identified as important pharmacological targets in AD pathogenesis, and it is to the identification of drugs which target Aβ and RAGE, and thus can be used to treat patients with AD and/or neuroinflammation that the present disclosure is directed.

DETAILED DESCRIPTION

Figure 1:
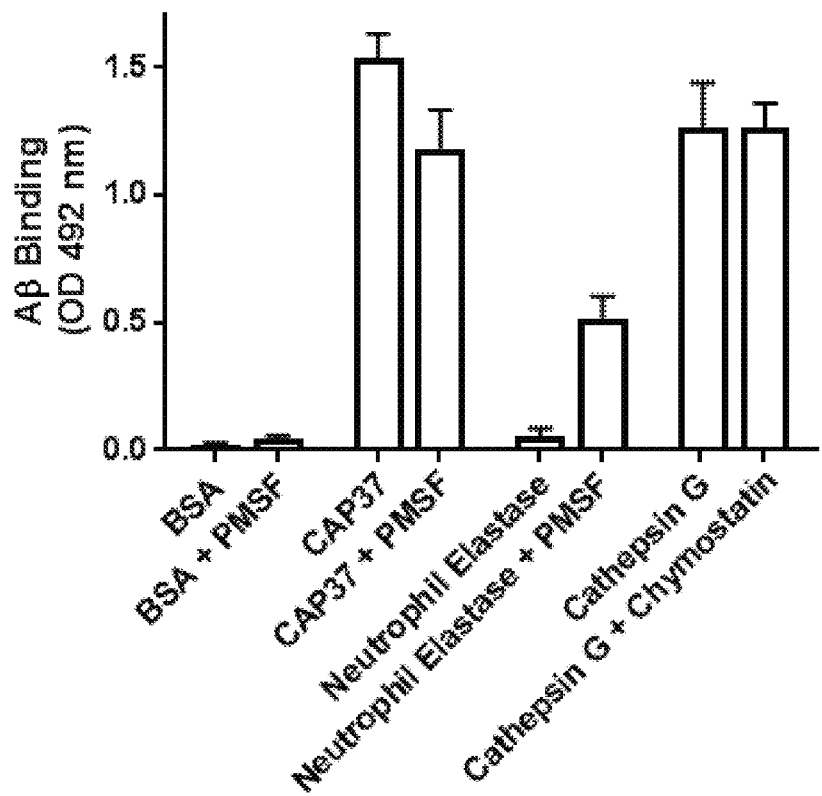
FIG. 1 shows binding of amyloid $\beta_{1-42}$ ($A\beta_{1-42}$) to full-length CAP37, NE, and CG proteins. The binding is stronger with CAP37 and CG, and is not significantly changed by the addition of antiproteases (phenylmethylsulfonyl fluoride (PMSF) or chymostatin). The binding of $A\beta_{1-42}$ to NE is almost undetectable, but significantly increased in the presence of PMSF, which inhibits the cleavage of $A\beta_{1-42}$ by NE.

The present disclosure, in at least certain embodiments, is directed to peptide compounds containing peptide sequences obtained from or derived from three neutrophil granule proteins cathepsin CE (CG), neutrophil elastase (NE) and cationic antimicrobial protein of 37 kDa (CAP37), methods of their use in inhibiting fibril formation and oligomerization of amyloid beta (Aβ), and methods of their use as therapeutics for treating, mitigating, and/or inhibiting diseases and conditions associated with Aβ, including for example, Alzheimer's disease (AD), cerebral amyloid angiopathy, dementia, and/or neuroinflammation, and/or the symptoms thereof. It was discovered that CAP37, NE, and CG could cleave $A\beta_{1-42}$ (the 42-amino acid form of Aβ) at different sites and with different kinetics. It was also observed that CAP37, but not NE or CG, is upregulated in the brain of patients with Ali. It has been found that CAP37 binds to RAGE, similarly to binding to Aβ peptide, a previously known ligand of RAGE. NE and CG also bind to RAGE. The CAP37-RAGE and NE-RAGE interactions are inhibited by a specific RAGE inhibitor. It was hypothesized that binding and cleavage of $A\beta_{1-42}$ would inhibit its ability to form toxic oligomers and fibrils. The present disclosure describes CAP37. E. and CG, and peptide derivatives that can inhibit Aβ aggregation (fibril formation). It is believed that oligomerized and polymerized forms of Aβ are more toxic than the monomeric form. Therefore, inhibiting Aβ oligomerization and aggregation can decrease the toxicity of Aβ and delay the progression of AD.

Without wishing to be bound by theory, it is believed that the peptide compounds of the present disclosure can bind to RAGE at the blood-brain-barrier, thereby inhibiting the binding of systemically produced Aβ and therefore inhibiting its transport into the brain. The peptide, rather than Aβ, would then be transported through the blood-brain-barrier and into the brain by RAGE-mediated transcytosis. Once inside the brain, the peptide inhibits oligomerization and/or polymerization of Aβ, and causes disaggregation of aggregated Aβ (depolymerizes the Aβ oligomers and fibrils), and thereby decreases and reversing both the neurotoxic effects of Aβ and deposition of Aβ in amyloid plaques. Additionally, the peptides bind and antagonize the pro-inflammatory effects of RAGE and TLR4 on neurons and microglial cells, mediated by aggregated Aβ and other agonists, thereby reducing neuroinflammation.

Before further detailed description of various embodiments of the compositions and methods of use thereof of the present disclosure, it is to be understood that the present disclosure is not limited in application to the details of methods and compositions as set forth in the following description. The description provided herein is intended for purposes of illustration only and is not intended to be construed in a limiting sense. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that various embodiments of the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure as defined herein. Thus the examples described below, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Thus, while the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts disclosed herein.

All patents, published patent applications, and non-patent publications mentioned in the specification are indicative of the level of skill of those skilled in the art to which the present disclosure pertains. Each patent, published patent application, and non-patent publication referenced in any portion of this application is expressly incorporated herein by reference in its entirety to the same extent as if the individual patent, or published patent application, or non-patent publication was specifically and individually indicated to be incorporated by reference. In particular, U.S. Pat. Nos. 9,096,679; 9,603,896; 9,624,283, and 9,862,748 are expressly incorporated herein by reference in their entireties.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, observer error, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 80% of the time, at least 90% of the time, at least 91% of the time, at least 92% of the time, at least 93% of the time, at least 94% of the time, at least 95% of the time, at least 96% of the time, at least 97% of the time, at least 98% of the time, or at least 99% of the time.

As used herein any reference to "one embodiment" or "an embodiment" means that a particular element, feature, composition, structure, or characteristic described in connection with the embodiment is included in at least one embodiment. The appearances of the phrase "in one embodiment" in various places in the specification are not necessarily all referring to the same embodiment.

The terms, "AEEA," "AEEEA," "AEEP," and "AEEEP," as used herein, refer to short polyethylene glycol molecules ("mini-PEGs") which comprise, in certain embodiments, portions of compounds disclosed herein, and have the following specific meanings.

The term AEEA represents —NH(CH$_2$CH$_2$O)$_2$CH$_2$CO— or NH$_2$(CH$_2$CH$_2$O)$_2$CH$_2$CO—, an N- or C-terminal group derived from [2-(2-amino-ethoxy)-ethoxy]-acetic acid (also known as 8-Amino-3,6-dioxaoctanoic acid).

The term AEEEA represents —NH(CH$_2$CH$_2$O)$_3$CH$_2$CO— or NH$_2$(CH$_2$CH$_2$O)$_3$CH$_2$CO—, an N- or C-terminal group derived from {2-[2-(2-amino-ethoxy)-ethoxy]-ethoxy}-acetic acid (also known as 11-Amino-3,6,9-trioxaundecanoic acid).

The term AEEP represents —NH(CH$_2$CH$_2$O)$_2$CH$_2$CH$_2$CO— or NH$_2$(CH$_2$CH$_2$O)$_2$CH$_2$CH$_2$CO—, an N- or C-terminal group derived from [3-(2-amino-ethoxy)-ethoxy]-propanoic acid (also known as 9-amino-4,7-dioxanonanoic acid).

The term AEEEP represents —NH(CH$_2$CH$_2$O)$_3$CH$_2$CH$_2$CO— or NH$_2$(CH$_2$CH$_2$O)$_3$CH$_2$CH$_2$CO—, an N- or C-terminal group derived from [3-[2-(2-amino-ethoxy)-ethoxy]-ethoxy]-propanoic acid (also known as 12-amino-4,7,10-trioxadodecananoic acid).

The following is a list of other abbreviations used herein, as well as the whole word or phrase represented thereby:

AGEs: advanced glycation end-products.
Aβ: Amyloid beta or amyloid β.
ANOVA: analysis of variance.
APP: amyloid precursor protein
CAP37: cationic antimicrobial protein of molecular weight 37 KDa.
CG: cathepsin G.
BCA: bicinchoninic acid.
BSA: bovine serum albumin.
DAB: diaminobenzidine tetrahydrochloride.
BPI: bactericidal permeability-increasing.
DAG: diacyl glycerol.
EDTA: ethylenediaminetetraacetic acid.
EGF: epidermal growth factor.
EGFR: epidermal growth factor receptor.
ERK: extracellular-signal-regulated kinase.
FBS: fetal bovine serum.
5RMP: Five arginine-mini-PEG.
GCSF: granulocyte colony-stimulating factor.
GM-CSF: granulocyte macrophage colony-stimulating factor.
GPCR: G protein-coupled receptor.
HB-EGF: heparin binding-epidermal growth factor.
HBSS: Hank's balanced salt solution.
HCEC(s): human corneal epithelial cell(s).
H&E: hematoxylin and eosin.
HGF: hepatocyte growth factor.
HBD-1: human beta-defensin-1.
HMGB 1: high mobility group box-1.
IL-6: interleukin-6.
IL-8: interleukin-8.
IP-10: interferon-inducible protein-10.
KC: keratinocyte-derived chemokine.
KSFM: keratinocyte serum free media.
LPS: lipopolysaccharide.
MCP-1: monocyte chemotactic protein-1.
NADP: nicotinamide adenine dinucleotide phosphate.
NE: neutrophil elastase.
PBS: phosphate buffered saline.
PDGF-BB: platelet derived growth factor -BB.
PKC: protein kinase C.
PMA: phorbol 12-myristate 13-acetate.
PMSF: phenylmethylsulfonyl fluoride.
RAGE: receptor for advanced glycation end-products.
RIPA: radioimmunoprecipitation assay.
ROS: reactive oxygen species.
SDS-PAGE: sodium dodecyl sulfate polyacrylamide gel electrophoresis.
SFM: serum free media.
TBS: Tris-buffered saline.
TBST: Tris-buffered saline TWEEN® 20 (Thermo Fisher Scientific, Pittsburgh, PA).
TGF-β: transforming growth factor beta.
TNF-α: tumor necrosis factor alpha.
CG$_{119-144}$: amino acids 119-144 of Cathepsin G protein.
NE$_{119-145}$: amino acids 119-145 of Neutrophil elastase.
CAP37$_{120-146}$: amino acids 120-146 of CAP37 protein.
CG$_{20-47}$: amino acids 20-47 of Cathepsin G protein.
NE$_{20-44}$: amino acids 20-44 of Neutrophil elastase.
CAP37$_{20-44}$: amino acids 20-44 of CAP37 protein.

The following standard amino acid abbreviations are used herein:

Alanine:ala:A, Cysteine:cys:C, Aspartic acid:asp:D, Glutamic acid:glu:E, Phenylalanine:phe:F, Glycine:gly:G, Histidine:his:H, Isoleucine:ile:I, Lysine:lys:K, Leucine:leu:L, Methionine:met:M, Asparagine:asn:N, Glutamine:gln:Q, Proline:pro:P, Arginine:arg:R, Serine:ser:S, Threonine:thr:T, Valine:val:V, Tryptophan:trp:W, and Tyrosine:tyr:T.

The term "mutant" or "variant" is intended to refer to a protein, peptide, nucleic acid or organism which has at least one amino acid or nucleotide which is different from the wild type version of the protein, peptide, nucleic acid, or organism and includes, but is not limited to, point substitutions, multiple contiguous or non-contiguous substitutions, insertions, chimeras, or fusion proteins, and the nucleic acids which encode them. Examples of conservative amino acid substitutions include, but are not limited to, substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, tyrosine) and small amino acids (such as glycine, alanine, serine, threonine, methionine). Other examples of possible substitutions are described below.

The terms "peptide", "peptide analog", "peptide derivative", or "peptide compound", where used herein may refer to a molecule comprising only amino acids, or may refer to a molecule comprising amino acids and one or more non-amino acid structures (e.g., PEG units). The terms "peptide", "peptide analog", "peptide derivative", or "peptide compound", may refer to a variant ("mutant") of a "wild-type" peptide, or to a molecule comprising amino acids and one or more non-amino acid structures (e.g., PEG units).

The term "amyloid beta" (Aβ) refers to the Aβ peptide comprising either 1-40 or 1-42 amino acids, or other forms, unless otherwise specifically designated.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rabbits, rats, mice, guinea pigs, chinchillas, hamsters, ferrets, horses, pigs, goats, cattle, sheep, zoo animals, camels, llamas, non-human primates, including Old and New World monkeys and non-human primates (e.g., cynomolgus macaques, chimpanzees, rhesus monkeys, orangutans, and baboons), and humans.

Where used herein the term "active agent" refers to a compound or composition having a biological activity as described herein.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic effect without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

The terms "peptide" or "peptide sequence" are used herein to designate a series of amino acid residues, connected one to another. In natural ("wild type") peptides, amino acids are connected by peptide bonds between the alpha-amino and carbonyl groups of the adjacent amino acids to form an amino acid sequence. In certain embodiments, the peptides can range in length from 5 to 15 to 25 to 40 to 60 to 75 amino acids or more, for example, 5, 6, 7, 8, 9, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 to 75 to 100 amino acids, or more. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A "fusion protein" or "fusion polypeptide" refers to proteins or polypeptides (and may be used interchangeably) which have been created by recombinant or synthetic methods to combine peptides in a serial configuration. In certain embodiments, the CAP37, NE and CG peptide derivatives described elsewhere herein can be shortened, for example by 1, 2, 3, 4, or 5 amino acids on one end or both ends, as long as the resulting variant peptide retains the biological activity described herein in relation to the inhibition of oligomerization and/or polymerization of Aβ and/or disaggregation of Aβ. In other embodiments, the variant peptides may comprise insertions of one, two or three amino acids.

Where used herein, the term "wild type" refers to an amino acid sequence or peptide which occurs under natural conditions or in nature, as opposed to a "non-wild type" amino acid sequence or peptide which does not occur under natural conditions or in nature. A non-wild type amino acid sequence or peptide may be an amino acid sequence or peptide that differs from the wild type such as via substitution, deletion, or insertion of one or more natural (alpha) amino acids in one or more amino acid positions of the wild type amino acid sequence or peptide. A non-wild type amino acid sequence or peptide may also be an amino acid sequence or peptide that differs from the wild type by one or more substitutions with a corresponding D-amino acid, β amino acid, homo-amino acid, β-homo amino acid, or peptoid monomer analog thereof. For example, where the wild type peptide comprises a serine, the non-wild type may instead comprise a D-serine, β serine, homoserine, β-homoserine, or peptoid monomer analog of serine. The non-wild type may differ from the wild type in only one amino acid position, or in a subset of the amino acid positions, or in all of the amino acid positions. For example, a peptide which comprises only D-amino acids is known as a retro-inverso peptide. A non-wild type amino acid or peptide may also be one in which the two or more of the amino acid monomers are linked via a non-peptide bond, such as a peptoid bond. In certain embodiments the non-peptide bond of the non-wild type may may be of the following types: reverse peptide bond (—NH—CO—), —CH$_2$—NH—, —CH$_2$S—, CH$_2$CH$_2$—, —CH=CH—, —COCH$_2$—, —CH(OH)CH$_2$—, and —CH$_2$SO—. Exemplary non-peptide bonds which may be employed are described in U.S. Pat. Nos. 4,897,445 and 10,064,926 for example. A peptide compound of the present disclosure may also comprise a wild type amino acid sequence or peptide which is conjugated to another natural peptide or amino acid sequence, which when conjugated together comprise a synthetic or non-natural amino acid sequence or peptide. A peptide compound of the present disclosure may also comprise a wild type amino acid sequence or peptide which is conjugated to a non-natural amino acid sequence or peptide, e.g., one or more D-amino acids, β amino acids, homo-amino acids, β-homo amino acids, or peptoid monomer analogs. A peptide compound of the present disclosure may comprise a wild type amino acid sequence or peptide conjugated to a non-amino acid molecule, such as a PEG molecule, for enhancing solubility, penetrability, or resistance to enzymatic degradation. In another embodiment, a peptide may be "stapled" into a particular helical configuration. Such "stapling" within peptides is also considered to be non-wild type difference from wild type peptides. Stapled peptides are discussed in further detail below.

The terms "synthetic amino acid" and "non-natural amino acid" may be used in place of the term non-wild type, and also refer to an organic compound that has a structure similar to a natural amino acid so that it mimics the structure and reactivity of a natural amino acid. The synthetic amino acid as defined herein generally increases or enhances the properties of a peptide (e.g., selectivity, stability) when the synthetic amino acid is either substituted for a natural amino acid or incorporated into a peptide.

A non-wild type homolog of a wild type amino acid sequence or peptide therefore refers to an non-wild type amino acid sequence or peptide which has at least one difference from the wild type amino acid sequence or peptide in at least one way as set forth above.

The term non-wild type, when used in reference to a single amino acid molecule, may also refer to a single amino acid or amino acid analog such as a peptoid monomer, which does not occur under natural conditions or in nature, as opposed to a wild type amino acid.

Non-wild-type amino acid sequences and peptides of the present disclosure may include the common natural amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, including but not limited to: alpha-asparagine, 2-aminobutanoic acid, 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-sioleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, NN-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine.

Peptides of the present disclosure and the nucleic acids which encode them include peptide and nucleic acid variants which comprise substitutions (conservative or non-conservative) of the native amino acids or bases. For example, the peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

One of ordinary skill in the art would readily know how to make, identify, select or test such variants for binding activity against the same receptors targeted by the non-variant peptides. Particular examples of conservative amino acid substitutions include, but are not limited to, gly:ala substitutions; val:ile:leu substitutions; asn:glu:his substitutions; asp:glu substitutions; ser:thr:met substitutions; lys:arg:his substitutions; and phe:tyr:trp substitutions. Other types of substitutions, variations, additions, deletions and derivatives that result in functional variant peptides are also encompassed by the present disclosure, and one of skill in the art would readily know how to make, identify, or select such variants or derivatives, and how to test for receptor binding activity of those variants. Examples of conservative amino acid substitutions include, but are not limited to, substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, tyrosine) and small amino acids (such as glycine, alanine, serine, threonine, methionine). Other examples of possible substitutions are described below.

The term "mutant" or "variant" is intended to refer to a protein, peptide, nucleic acid or organism which has at least one amino acid or nucleotide which is different from the wild type version of the protein, peptide, nucleic acid, or organism and includes, but is not limited to, point substitutions, multiple contiguous or non-contiguous substitutions, insertions, chimeras, or fusion proteins, and the nucleic acids which encode them, or other non-wild type features as described above.

The terms "peptide", "peptide analog", "peptide derivative", or "peptide compound", where used herein may refer to a molecule comprising only amino acids, or may refer to a molecule comprising amino acids and one or more non-amino acid structures (e.g., PEG units). The terms "peptide", "peptide analog", "peptide derivative", or "peptide compound", may refer to a variant ("mutant") of a "wild-type" peptide, or to a molecule comprising amino acids and one or more non-amino acid structures (e.g., PEG units).

The term "polypeptide" or "protein" is used herein to designate a series of amino acid residues, connected one to the other typically by peptide bonds between the alpha-amino and carbonyl groups of the adjacent amino acids, wherein the length is longer than a single peptide, or by other connecting bonds as described herein. A peptide compound of the present disclosure may be a peptide conjugate, which in a non-limiting embodiment is a compound comprising a peptide of the present disclosure which is conjugated (e.g., covalently linked, directly or indirectly via a linker sequence) to another molecule, such as (but not limited to) a carrier molecule such as (but not limited to) a protein or other polymeric molecule, e.g., a serum albumin molecule or antibody, or other therapeutic compound such as (but not limited to) a drug, or an imaging or diagnostic moiety, and wherein the peptide retains its activity (e.g., binding, targeting, imaging, or inhibitory) even when conjugated to the molecule. The peptides of the present disclosure may be produced using any nucleotide sequence which encodes the desired amino acid sequence. Any of the peptides described herein or active variants thereof may be used to make the peptide conjugates of the present disclosure.

The term "homologous" or "% identity" as used herein means a nucleic acid (or fragment thereof) or a peptide having a degree of homology to the corresponding natural reference nucleic acid or peptide that may be in excess of 60%, or in excess of 65%, or in excess of 70%, or in excess of 75%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%, or other specific percentages described herein. For example, in regard to peptides, the percentage of homology or identity as described herein is typically calculated as the percentage of amino acid residues found in the smaller of the two sequences which align with identical amino acid residues in the sequence being compared, when four gaps per 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

In at least one embodiment, "% identity" represents the number of amino acids or nucleotides which are identical at corresponding positions in two sequences of a peptide or nucleic acids encoding similar peptides. For example, two amino acid sequences each having 15 residues will have at least 60% identity when at least 9 of the amino acids at corresponding positions are the same, at least 66% identity when at least 10 of the amino acids at corresponding positions are the same, at least 73% identity when at least 11 of the amino acids at corresponding positions are the same, at least 80% identity when at least 12 of the amino acids at corresponding positions are the same, at least 86% identity when at least 13 of the amino acids at corresponding positions are the same, and at least 93% identity when at least 14 of the amino acids at corresponding positions are the same. In another example, two amino acid sequences each having 19 residues will have at least 73% identity when at least 14 of the amino acids at corresponding positions are the same, at least 78% identity when at least 15 of the amino acids at corresponding positions are the same, at least 84% identity when at least 16 of the amino acids at corresponding positions are the same, at least 89% identity when at least 17 of the amino acids at corresponding positions are the same, and at least 94% identity when at least 18 of the amino acids at corresponding positions are the same.

Similarly, two amino acid sequences each having 20 residues will have at least 95% identity when 19 of the amino acids at corresponding positions are the same, or at least 90% identity when at least 18 of the amino acids at corresponding positions are the same, or at least 85% identity when at least 17 of the amino acids at corresponding positions are the same, or at least 80% identity when at least 16 of the amino acids at corresponding positions are the same. In other non-limiting examples, two amino acid sequences each having 100 residues will have 95% identity when 95 of the amino acids at corresponding positions are the same. Two amino acid sequences each having 100 residues will have at least 90% identity when at least 90 of the amino acids at corresponding positions are the same. Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

In at least certain embodiments, the present disclosure is directed to a peptide comprising at least 25 amino acids, wherein the peptide contains at least one D-amino acid up to at least 25 D-amino acids. In certain embodiments, the peptides of the present disclosure which have a sequence selected from SEQ ID NOS:1-6, said sequence may include at least one or more D-amino acids or may be entirely of D-amino acids. Peptides which include one or more D-amino acids possess certain properties in comparison to peptides which are made up of only L-amino acids, including but not limited to: (1) the ability to withstand all natural peptidases which can act on peptides comprising L-amino acids; (2) the capability for withstanding gastro-enteric exposure to natural peptidases and to limited acid hydrolysis; and (3) the potential for oral, nasal, or alveolar administration.

As discussed above, in certain embodiments, the peptides of the present disclosure comprise one or more β amino acids in which the primary amino group of the amino acid is bonded to the β carbon of the amino acid rather than to the α amino acid as in natural amino acids. Such β amino acids are commercially available. In alternate embodiments, the amino acids may be homo-amino acid or β-homo amino acid versions of the α amino acids described herein.

As discussed above, in certain embodiments, the term "peptide compound" as used herein also is intended to include peptoid versions of the peptides described herein. Peptoids include peptoid monomer analogs of the α amino acids described herein. All of the amino acids, or a portion of the amino acids of the peptides of the present disclosure may be peptoid monomer-equivalents of the α amino acids described elsewhere herein. Peptoids are made up of poly-N-substituted glycine monomers and comprise a class of peptidomimetics whose side chains are bonded to the nitrogen atom of the peptide backbone, rather than to the α-carbons (as they are in amino acids). Peptoids lack the amide hydrogen which is responsible for many of the secondary structure elements in peptides and proteins. Like D-amino acids peptides and β amino acid peptides, peptoids are resistant to proteolysis, and are therefore advantageous for therapeutic applications where proteolysis is a major issue.

Thus, where the 20 natural amino acids are identified herein, it is intended that each be read not only as a natural L-amino acid, but alternatively as a D-amino acid, as a β amino acid, as a homo-amino acid, as a β-homo amino acid, or as a peptoid monomer analog thereof.

In other non-limiting embodiments, the amino acid sequences of the presently disclosed peptide compounds may be "stapled" into a particular helical configuration meaning that certain non-adjacent residues, regions, portions, or domains of the peptide are connected to each other. Stapled peptides generally exhibit increased α-helical stability compared to a corresponding non-stapled peptide. In other embodiments, the stapled peptide exhibits increased thermal stability compared to a corresponding non-stapled peptide. In yet other embodiments, the stapled peptide exhibits increased biological activity compared to a corresponding non-stapled polypeptide. In still other embodiments, the stapled peptide exhibits increased resistance to proteolytic degradation compared to a corresponding non-stapled peptide. In yet other embodiments, the stapled peptide exhibits increased ability to penetrate living cells compared to a corresponding non-stapled peptide.

The term "stapled peptide" as used herein refers to a peptide having a selected number of standard (wild type or natural) or non-standard (non-wild type or non-natural) amino acids, and further having at least two moieties capable of undergoing reaction to promote carbon-carbon bond formation, that has been contacted with a reagent to generate at least one cross-linker between the at least two moieties, which modulates, for example, peptide stability. The term "stapling" as used herein introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an α-helix structure. The length and geometry of the cross-linker can be optimized to improve the yield of the desired secondary structure content. The constraint provided can, for example, prevent the secondary structure from unfolding and/or can reinforce the shape of the secondary structure. A secondary structure that is prevented from unfolding is, for example, more stable. Further examples of peptide stapling are shown in U.S. Pat. Nos. 8,586,707; 10,011,631; 10,308,684; and 10,682,388, each of which is hereby expressly incorporated by reference herein in its entirety.

In certain embodiments, the i position (where i is an integer), and i+4 position (or i+7 and/or i+11 positions, or others), of the α-helix can be stapled using various covalent bonding methods. Specifically, the amino acids at one or more positions selected from the group consisting of i, i+3, i+4, i+7, i+8, i+10 and i+11 may be stapled. The stapled peptide may have increased cell-penetrating ability versus the non-stapled version. In some cases, two or more amino acid positions selected from the group consisting of i, i+3, i+4, i+7, i+8, i+10 and i+11 may be stapled. Typically, two amino acids may be connected to each other by a disulfide bond, a carbon-carbon double bond or an amide bond. Examples of the method for linking two amino acids to each other include introduction of disulfide between two amino acid positions, introduction of a carbon-carbon double bond by a metathesis reaction, introduction of an amide bond, introduction of a short linker by the Michael reaction, and the like.

The term "peptide stapling" may encompass the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. In a specific embodiment, the introduction of a staple entails a modification of standard peptide synthesis, with α-methyl, α-alkenyl amino acids being introduced at two positions along the peptide chain, separated by either three or six intervening residues (i+4 or i+7). These spacings place the stapling amino acids on the same face of the α-helix, straddling either one (i+4) or two (i+7) helical turns. Additionally, the term "peptide stitching" refers to multiple and tandem "stapling" events in a single peptide chain to provide a "stitched" (multiply stapled) polypeptide. Published PCT application WO 2008/121767, which is hereby expressly incorporated by reference herein in its entirety, shows a specific example of stitched peptide technology.

In certain embodiments, the stapling process may be conducted using the "Stapled Peptide" technology of Aileron Therapeutics, wherein two key residues within the peptide are modified by attachment of linkers through the amino acid side chains. Once synthesized, the linkers are connected through a catalyst, thereby creating a bridge that physically constrains the peptide into its native α-helical shape.

In certain embodiments, when the peptide has a helical secondary structure, the staple is a macrocyclic ring, which is exogenous (not part of) core or inherent (non-stapled) helical peptide structure. The macrocyclic ring is comprised of a pyrazoline ring and incorporates at least two amino acids of the peptide. The size of the macrocyclic ring is determined by the number of helical peptide amino acids (y) in the ring and the number methylene groups in the moieties connecting the pyrazoline group to the peptide (m and n).

The stapled peptide has a least one peptide. In various embodiments, the stapled peptide has 1, 2, or 3 staples.

The peptide compounds of the present disclosure may further contain a labeling agent, which is conjugated to the peptide. Various methods of labeling peptides are known in the art and may be used in accordance with the present disclosure. Examples of labels for peptides and polypeptides include, but are not limited to, the following: radioisotopes or radionuclides, fluorescent labels, chemiluminescent labels, and the like. In some embodiments, the labeling agent may be attached to the peptide by a spacer or linker of various lengths to reduce potential steric hindrance. In addition, the terms "label," "labeling agent," "detectable marker," "detection moiety," and "reporter molecule" are used interchangeably herein. These conjugates are useful in various diagnostic methods.

Examples

Examples are provided hereinbelow. However, the present disclosure is to be understood as not limited in its application to the specific experimentation, results, and laboratory procedures disclosed below or elsewhere herein. Rather, each example is provided as one of various embodiments and are meant to be exemplary, not exhaustive.

In certain embodiments, the present disclosure is directed to peptide compounds which are entirely or partially made up of one or more of the following amino acid sequences:

$CG_{119-144}$: GTLCTVAGWGRVSMRRGTDTL-REVQL (SEQ ID NO:1), $NE_{119-145}$: GVQCLAMGWGLL-GRNRGIASVLQELNV (SEQ ID NO:2), $CAP37_{120-46}$: GTRCQVAGWGSQRSGGRLSRF-PRFVNV (SEQ ID NO:3), $CG_{20-47}$: IQSPAGQSRCGGFLVREDFVL-TAAHCWG (SEQ ID NO:4), $NE_{20-44}$: LRGGHFCGATLIAPNFVMSAAHCV (SEQ ID NO:5), and $CAP37_{20-44}$: NQGRHFCGGALIHARF-VMTAASCFQ (SEQ ID NO:6).

More particularly, the present disclosure includes, but is not limited to peptide variants of SEQ ID NOS: 1-6 which comprise specific substitutions as described below.

In certain non-limiting embodiments, variants of $CG_{119-144}$ (SEQ ID NO:1) comprising one or more of the following substitutions can be used to form the peptide compounds used herein: One or more of the four basic arginine residues (positions 11, 15, 16, 22) could be changed to lysine or histidine. The acidic residue aspartate in position 19 could be changed to glutamate, arginine, lysine, or histidine. The glutamate in position 23 could be changed to aspartate or a proline-arginine ("PR") pair. One or more of the threonine residues in positions 2, 5, 18, and 20 could be changed to another hydrophilic residue (asparagine, glutamine, serine, tyrosine) or to another small residue (serine, alanine, glycine, valine, proline). One or more of the two other hydrophilic residues, serine in position 13 and glutamine in position 25, can similarly be changed to another hydrophilic residue (asparagine, glutamine, serine, threonine, or tyrosine). One or more of the other residues in this sequence (being hydrophobic) could be substituted to another hydrophobic residue (alanine, glycine, cysteine, valine, proline, leucine, isoleucine, methionine, phenylalanine, tryptophan). Other possible substitutions or alterations are described in further detail below (see SEQ ID NO:7). Each of the amino acids identified above is intended to be read not only as an L-α-amino acid, but also alternatively as a D-amino acid, a β amino acid, a homo-amino acid, a β-homo amino acid, or a peptoid mononer analog thereof.

In other non-limiting embodiments, variants of $NE_{119-145}$ (SEQ ID NO:2) comprising one or more of the following substitutions can be used to form the peptide compounds used herein: The aromatic tryptophan residue in position 9 could be changed to another aromatic residue (tyrosine or phenylalanine). The acidic residue glutamate in position 24 could be changed to aspartate. One or more of the two basic arginine residues in positions 14 and 16 could be changed to another basic amino acid (lysine or histidine). One or more of the polar residues glutamine (positions 3 and 23), asparagine (position 15), and serine (position 20) could be changed to any other polar residue (asparagine, glutamine, serine, threonine, or tyrosine). Serine in position 20 could also be changed to another small residue (threonine, alanine, glycine, valine, proline). One or more of the other residues in this sequence (being hydrophobic) could be substituted to another hydrophobic residue (alanine, glycine, cysteine, valine, proline, leucine, isoleucine, methionine, phenylalanine, tryptophan). Other possible substitutions or alterations are described in further detail below (see SEQ ID NO:8). Each of the amino acids identified above is intended to be read not only as an L-α-amino acid, but also alternatively as a D-amino acid, a β amino acid, a homo-amino acid, a β-homo amino acid, or a peptoid mononer analog thereof.

In other non-limiting embodiments, variants of $CAP37_{120-146}$ (SEQ ID NO:3) comprising one or more of the following substitutions can be used to form the peptide compounds used herein: One or more of the small, hydrophobic glycine residues in positions 1, 8, 10, 15, 16 of this peptide could be changed to another hydrophobic amino acid (alanine, cysteine, valine, proline, leucine, isoleucine, methionine, phenylalanine or tryptophan), or to another small amino acid (alanine, serine, threonine, valine or proline). Similarly, One, 2, 3, 4, or all of the positively charged arginine residues in positions 3, 13, 17, 20, 23 could be changed to another basic amino acid (lysine or histidine). Other examples for this sequence would be to change one or more of the hydrophilic amino acids threonine in position 2, glutamines in positions 5 and 12, and serines in positions 14 and 19, to a different hydrophilic residue, e.g., threonine could be changed to asparagine, glutamine, serine or tyrosine; glutamine could be changed to asparagine, serine, threonine or tyrosine; and serine could be changed to asparagine, glutamine, threonine or tyrosine. One or more of the other residues in this sequence (being hydrophobic) could be substituted to another hydrophobic residue (alanine, glycine, cysteine, valine, proline, leucine, isoleucine, methionine, phenylalanine, tryptophan). Other possible substitutions or alterations are described in further detail below (see SEQ ID NO:9). Each of the amino acids identified above is intended to be read not only as an L-α-amino acid, but also alternatively as a D-amino acid, a β amino acid, a homo-amino acid, a β-homo amino acid, or a peptoid mononer analog thereof.

In other non-limiting embodiments, alternative variants of $CG_{20-47}$ (SEQ ID NO:4) comprising one or more of the following substitutions can be used to form the peptide compounds used herein: In this sequence, the two negatively charged residues, glutamate and aspartate (in positions 17 and 18 respectively) could be changed to two glutamates or to two aspartates, or could be inverted to aspartate and glutamate, respectively. One or more of the two positively charged arginine residues in positions 9 and 16 of this peptide could be conservatively changed to lysine or histidine, and the histidine residue in position 25 could be changed to arginine or lysine. One or more of the polar glutamine residues in positions 2 and 7 could be changed to asparagine, serine, threonine or tyrosine; and one or more of the polar serine residues in positions 3 and 8 could be changed to asparagines, glutamine, threonine or tyrosine. One or more of the other residues in this sequence (being hydrophobic) could be substituted to another hydrophobic residue (alanine, glycine, cysteine, valine, proline, leucine, isoleucine, methionine, phenylalanine, tryptophan). One or more of the aromatic residues phenylalanine 13 and 19, and tryptophan 27, could be changed to another aromatic residue (phenylalanine, tryptophan or tyrosine). Other possible substitutions or alterations are described in further detail below (see SEQ ID NO:10). Each of the amino acids identified above is intended to be read not only as an L-α-amino acid, but also alternatively as a D-amino acid, a β amino acid, a homo-amino acid, a β-homo amino acid, or a peptoid mononer analog thereof.

In other non-limiting embodiments, alternative variants of $NE_{20-44}$ (SEQ ID NO:5) comprising one or more of the following substitutions can be used to form the peptide compounds used herein: The positively charged arginine residue in position 2 of this peptide could be conservatively changed to lysine or histidine, and one or more of the two histidine residues in positions 5 and 22 could be changed to arginine or lysine. One or more of the two polar residues asparagine 15 and serine 19 could be changed to any other polar residue (asparagine, glutamine, serine, threonine or tyrosine). One or more of the other residues in this sequence (being hydrophobic) could be substituted to another hydrophobic residue (alanine, glycine, cysteine, valine, proline, leucine, isoleucine, methionine, phenylalanine, tryptophan). One or more of the phenylalanines in positions 6 and 16 could be changed to another aromatic residue, either tryptophan or tyrosine. Other possible substitutions or alterations are described in further detail below (see SEQ ID NO:11). Each of the amino acids identified above is intended to be read not only as an L-α-amino acid, but also alternatively as a D-amino acid, a β amino acid, a homo-amino acid, a β-homo amino acid, or a peptoid mononer analog thereof.

In other non-limiting embodiments, alternative variants of $CAP37_{20-44}$ (SEQ ID NO:6) comprising one or more of the following substitutions can be used to form the peptide compounds used herein: One or more of the two positively charged arginine residues in positions 4 and 15 of this peptide could be conservatively changed to lysine or histidine, and one or more of the two histidine residues in positions 5 and 13 could be changed to arginine or lysine. One or more of the three aromatic phenylalanine residues in positions 6, 16, 24 could be changed to other aromatic residues tryptophan or tyrosine. One or more of the polar residues asparagine 1, glutamines 2 and 25, threonine 19, and serine 22 could be changed to any other polar residues (asparagine, glutamine, serine, threonine or tyrosine). One or more of the other residues in this sequence (being hydrophobic) could be substituted to another hydrophobic residue (alanine, glycine, cysteine, valine, proline, leucine, isoleucine, methionine, phenylalanine, tryptophan). Other possible substitutions or alterations are described in further detail below (see SEQ ID NO:12). Each of the amino acids identified above is intended to be read not only as an L-α-amino acid, but also alternatively as a D-amino acid, a β amino acid, a homo-amino acid, a β-homo amino acid, or a peptoid mononer analog thereof.

Furthermore, the peptide compound may comprise a peptide having an amino acid sequence derived from $CG_{119-144}$ peptide, $NE_{119-145}$, $CAP37_{120}$-146, $CG_{20-47}$, $NE_{20-44}$, or $CAP37_{20-44}$ as shown in the sequences below (residues in boldface indicate the amino acids of the wild-type sequence).

In at least one embodiment, the peptide compound comprises a derivative of peptide $CG_{119-144}$ having the following amino acid sequence (SEQ ID NO:7):

$$X_1X_2X_3X_4X_5X_6X_7X_8X_9X_{10}X_{11}X_{12}X_{13}X_{14}X_{15}$$
$$X_{16}X_{17}X_{18}X_{19}X_{20}X_{21}X_{22}X_{23}X_{24}X_{25}X_{26}$$

wherein
$X_1$ is G,
$X_2$ is selected from A, F, G, I, L, M, P, S, T, W, and V,
$X_3$ is selected from A, F, G, H, I, K, L, M, N, P, Q, R, V, and W,
$X_4$ is selected from A, C, S, T, and V,
$X_5$ is selected from A, F, G, I, L, M, P, S, T, W, and V,
$X_6$ is selected from A, F, G, I, L, M, P, W, and V,
$X_7$ is selected from A, F, G, I, L, M, P, W, and V,
$X_8$ is G,
$X_9$ is selected from A, F, G, I, L, M, P, W, and V,
$X_{10}$ is G,
$X_{11}$ is selected from A, C, F, G, H, I, K, L, M, N, P, Q, R, S, T, V, W, and Y,
$X_{12}$ is selected from A, F, G, I, L, M, P, W, and V,
$X_{13}$ is selected from A, C, F, G, I, L, M, N, P, Q, S, T, V, W, and Y,
$X_{14}$ is selected from A, F, G, I, L, M, P, W, and V,
$X_{15}$ is selected from H, K, and R,
$X_{16}$ is selected from C, H, K, N, Q, R, S, T, and Y,
$X_{17}$ is G,
$X_{18}$ is selected from C, N, Q, S, T, and Y,
$X_{19}$ is selected from D, E, H, K, and R,
$X_{20}$ is selected from A, C, F, G, I, L, M, N, P, Q, S, T, V, W, and Y,
$X_{21}$ is selected from A, C, F, G, I, L, M, N, P, Q, S, T, V, W, and Y,
$X_{22}$ is selected from A, F, G, H, I, K, L, M, P, R, W, and V,
$X_{23}$ is selected from L, C, D, E, F, G, H, I, K, A, M, N, P, Q, R, PR, S, T, V, W, and Y,
$X_{24}$ is selected from A, F, G, I, L, M, P, W, and V,
$X_{25}$ is selected from C, N, Q, S, T, and Y, and
$X_{26}$ is selected from A, F, G, I, L, M, P, W, and V.

In alternate embodiments, positions $X_{17}$ and/or $X_{18}$ and/or $X_{23}$ of SEQ ID NO: 7 may be altered by deletion, insertion, or substitution as shown below in Table 1.

TABLE 1

Optional deletions/insertions/substitutions at $X_{17}$/$X_{18}$/$X_{23}$ in SEQ ID NO: 7

| $X_{17}$ | $X_{18}$ | $X_{23}$ |
|---|---|---|
| deleted | Any one of C, N, Q, S, T, Y | PR |
| G | deleted | PR |
| deleted | deleted | PR |
| G | G | PR |
| Any one of C, N, Q, S, T, Y | Any one of C, N, Q, S, T, Y | PR |
| Any one of C, N, Q, S, T, Y | Any two of C, N, Q, S, T, Y | PR |
| Any one of C, N, Q, S, T, Y | Any three of C, N, Q, S, T, Y | PR |

TABLE 1-continued

Optional deletions/insertions/substitutions at $X_{17}/X_{18}/X_{23}$ in SEQ ID NO: 7

| $X_{17}$ | $X_{18}$ | $X_{23}$ |
|---|---|---|
| G | Any two of C, N, Q, S, T, Y | PR |
| G | Any three of C, N, Q, S, T, Y | PR |
| G G | Any one of C, N, Q, S, T, Y | PR |
| G G | Any two of C, N, Q, S, T, Y | PR |

In at least one embodiment, the peptide compound comprises a derivative of peptide $NE_{119-145}$ having the following amino acid sequence (SEQ ID NO:8):

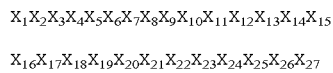

wherein
 $X_1$ is G,
 $X_2$ is selected from A, F, G, I, L, M, P, S, T, W, and V,
 $X_3$ is selected from A, F, G, H, I, K, L, M, N, P, Q, R, V, and W,
 $X_4$ is selected from A, C, S, T, and V,
 $X_5$ is selected from A, F, G, I, L, M, P, S, T, W, and V,
 $X_6$ is selected from A, F, G, I, L, M, P, W, and V,
 $X_7$ is selected from A, F, G, I, L, M, P, W, and V,
 $X_8$ is G,
 $X_9$ is selected from A, F, G, I, L, M, P, W, and V,
 $X_{10}$ is G,
 $X_{11}$ is selected from A, F, G, I, L, M, P, W, and V,
 $X_{12}$ is selected from A, C, F, G, I, L, M, N, P, Q, S, T, V, W, and Y,
 $X_{13}$ is selected from A, F, G, I, L, M, P, W, and V,
 $X_{14}$ is selected from H, K, and R,
 $X_{15}$ is selected from C, H, K, N, Q, R, S, T, and Y,
 $X_{16}$ is selected from A, F, G, H, I, K, L, M, P, R, W, and V,
 $X_{17}$ is G,
 $X_{18}$ is selected from D, A, E, F, G, I, L, M, P, W, and V,
 $X_{19}$ is selected from A, C, F, G, I, L, M, N, P, Q, S, T, V, W, and Y,
 $X_{20}$ is selected from A, C, F, G, I, L, M, N, P, Q, S, T, V, W, and Y,
 $X_{21}$ is selected from A, F, G, H, I, K, L, M, P, R, W, and V,
 $X_{22}$ is selected from A, C, F, G, I, L, M, N, P, Q, S, T, V, W, and Y,
 $X_{23}$ is selected from C, N, Q, S, T, and Y, and
 $X_{24}$ is selected from A, C, D, E, F, G, H, I, K, L, M, N, P, Q, R, S, T, V, W, and Y,
 $X_{25}$ is selected from A, F, G, I, L, M, P, W, and V,
 $X_{26}$ is selected from C, N, Q, S, T, and Y, and
 $X_{27}$ is selected from A, F, G, I, L, M, P, W, and V.

In alternate embodiments, positions $X_{16}$ and/or $X_{17}$ of SEQ ID NO: 8 may be altered by deletion, insertion, or substitution as shown below in Table 2.

TABLE 2

Optional deletions/insertions/substitutions at $X_{16}/X_{17}$ in SEQ ID NO: 8

| $X_{16}$ | $X_{17}$ |
|---|---|
| deleted | deleted |
| deleted | Any one of C, N, Q, S, T, Y |

TABLE 2-continued

Optional deletions/insertions/substitutions at $X_{16}/X_{17}$ in SEQ ID NO: 8

| $X_{16}$ | $X_{17}$ |
|---|---|
| deleted | Any two of C, N, Q, S, T, Y |
| deleted | Any three of C, N, Q, S, T, Y |
| G | deleted |
| G | G |
| G | Any one of C, N, Q, S, T, Y |
| G | Any two of C, N, Q, S, T, Y |
| G | Any three of C, N, Q, S, T, Y |
| GG | Any one of C, N, Q, S, T, Y |
| GG | Any two of C, N, Q, S, T, Y |
| Any one of C, N, Q, S, T, Y | Any one of C, N, Q, S, T, Y |
| Any one of C, N, Q, S, T, Y | Any two of C, N, Q, S, T, Y |
| Any one of C, N, Q, S, T, Y | Any three of C, N, Q, S, T, Y |
| Any one of C, N, Q, S, T, Y | G |
| Any one of C, N, Q, S, T, Y | GG |

In at least one embodiment, the peptide compound comprises a derivative of peptide $CAP37_{120-146}$ having the following amino acid sequence (SEQ ID NO:9):

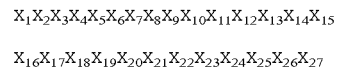

wherein
 $X_1$ is G,
 $X_2$ is selected from A, F, G, I, L, M, P, S, T, W, and V,
 $X_3$ is selected from A, F, G, H, I, K, L, M, N, P, Q, R, V, and W,
 $X_4$ is selected from A, C, S, T, and V,
 $X_5$ is selected from A, F, G, I, L, M, N, P, Q, S, T, W, and V,
 $X_6$ is selected from A, F, G, I, L, M, P, W, and V,
 $X_7$ is selected from A, F, G, I, L, M, P, W, and V,
 $X_8$ is G,
 $X_9$ is selected from A, F, G, I, L, M, P, W, and V,
 $X_{10}$ is G,
 $X_{11}$ is selected from A, C, F, G, I, L, M, N, P, Q, S, T, V, W, and Y,
 $X_{12}$ is selected from W, A, C, F, G, I, L, M, N, P, Q, S, T, V, and Y,
 $X_{13}$ is selected from C, H, K, N, Q, R, S, T, and Y,
 $X_{14}$ is selected from C, H, K, N, Q, R, S, T, and Y,
 $X_{15}$ is G,
 $X_{16}$ is selected from A, F, G, I, L, M, P, S, T, W, and V,
 $X_{17}$ is selected from D, A, E, F, G, I, K, L, M, P, R, S, T, V, W, and Y,
 $X_{18}$ is selected from A, C, F, G, I, L, M, N, P, Q, S, T, V, W, and Y,
 $X_{19}$ is selected from A, C, F, G, I, L, M, N, P, Q, S, T, V, W, and Y,
 $X_{20}$ is selected from A, F, G, H, I, K, L, M, P, R, W, and V,
 $X_{21}$ is selected from A, F, G, I, L, M, P, V, W, and Y,
 $X_{22}$ is selected from A, C, D, E, F, G, H, I, K, L, M, N, P, Q, R, S, T, V, W, and Y
 $X_{23}$ is selected from A, C, D, E, F, G, H, I, K, L, M, N, P, Q, R, S, T, V, W, and Y,
 $X_{24}$ is selected from A, F, G, I, L, M, P, W, and V,
 $X_{25}$ is selected from A, F, G, I, L, M, P, W, and V,
 $X_{26}$ is selected from C, N, Q, S, T, and Y, and
 $X_{27}$ is selected from A, F, G, I, L, M, P, W, and V.

In alternate embodiments, positions $X_{15}$ and/or $X_{16}$ of SEQ ID NO: 9 may be altered by deletion, insertion, or substitution as shown below in Table 3.

$$X_1X_2X_3X_4X_5X_6X_7X_8X_9X_{10}X_{11}X_{12}X_{13}X_{14}X_{15}$$

$$X_{16}X_{17}X_{18}X_{19}X_{20}X_{21}X_{22}X_{23}X_{24}X_{25}X_{26}X_{27}X_{28}$$

In at least one embodiment, the peptide compound comprises a derivative of peptide $CG_{20\text{-}47}$ having the following amino acid sequence (SEQ ID NO:10):

TABLE 3

| Optional deletions/insertions/substitutions at $X_{15}/X_{16}$ in SEQ ID NO: 9 | |
|---|---|
| $X_{15}$ | $X_{16}$ |
| deleted | deleted |
| deleted | Any one of C, N, Q, S, T, Y |
| deleted | Any two of C, N, Q, S, T, Y |
| deleted | Any three of C, N, Q, S, T, Y |
| G | deleted |
| G | Any one of C, N, Q, S, T, Y |
| G | Any two of C, N, Q, S, T, Y |
| G | Any three of C, N, Q, S, T, Y |
| GG | Any one of C, N, Q, S, T, Y |
| GG | Any two of C, N, Q, S, T, Y |
| Any one of C, N, Q, S, T, Y | Any three of C, N, Q, S, T, Y | wherein
- $X_1$ is selected from F, Y, W, A, V, I, L and M,
- $X_2$ is selected from N, S, T and Q,
- $X_3$ is selected from N, S, T and Q,
- $X_4$ is selected from P, F, Y, W, A, V, I, L, M and G,
- $X_5$ is selected from F, Y, W, A, V, I, L and M,
- $X_6$ is selected from G, A and V,
- $X_7$ is selected from N, S, T and Q,
- $X_8$ is selected from N, S, T and Q,
- $X_9$ is selected from R, H and K,
- $X_{10}$ is selected from C, S and T,
- $X_{11}$ is selected from G, A and V,
- $X_{12}$ is selected from G, A and V,
- $X_{13}$ is selected from F, Y, W, A, V, I, L and M,
- $X_{14}$ is selected from F, Y, W, A, V, I, L and M,
- $X_{15}$ is selected from F, Y, W, A, V, I, L and M,
- $X_{16}$ is selected from R, H and K,
- $X_{17}$ is selected from E and D,
- $X_{18}$ is selected from E and D,
- $X_{19}$ is selected from F, Y, W, A, V, I, L and M,
- $X_{20}$ is selected from F, Y, W, A, V, I, L and M,
- $X_{21}$ is selected from F, Y, W, A, V, I, L and M,
- $X_{22}$ is selected from N, S, T and Q,
- $X_{23}$ is selected from F, Y, W, A, V, I, L and M,
- $X_{24}$ is selected from F, Y, W, A, V, I, L and M,
- $X_{25}$ is selected from R, H and K,
- $X_{26}$ is selected from C, S and T,
- $X_{27}$ is selected from F, Y, W, A, V, I, L and M, and
- $X_{28}$ is selected from G, A and V.

In at least one embodiment, the peptide compound comprises a derivative of peptide $NE_{20\text{-}44}$ having the following amino acid sequence (SEQ ID NO:11):

$$X_1X_2X_3X_4X_5X_6X_7X_8X_9X_{10}X_{11}X_{12}X_{13}X_{14}X_{15}$$

$$X_{16}X_{17}X_{18}X_{19}X_{20}X_{21}X_{22}X_{23}X_{24}X_{25}$$

wherein
- $X_1$ is selected from F, Y, W, A, V, I, L and M,
- $X_2$ is selected from R, H and K,
- $X_3$ is selected from G, A and V,
- $X_4$ is selected from G, A and V,
- $X_5$ is selected from R, H and K,
- $X_6$ is selected from F, Y, W, A, V, I, L and M,
- $X_7$ is selected from C, S and T,
- $X_8$ is selected from G, A and V,
- $X_9$ is selected from F, Y, W, A, V, I, L and M,
- $X_{10}$ is selected from N, S, T and Q,
- $X_{11}$ is selected from F, Y, W, A, V, I, L and M,
- $X_{12}$ is selected from F, Y, W, A, V, I, L and M,
- $X_{13}$ is selected from F, Y, W, A, V, I, L and M,
- $X_{14}$ is selected from P, F, Y, W, A, V, I, L, M and G,
- $X_{15}$ is selected from N, S, T and Q,
- $X_{16}$ is selected from F, Y, W, A, V, I, L and M,
- $X_{17}$ is selected from F, Y, W, A, V, I, L and M,
- $X_{18}$ is selected from F, Y, W, A, V, I, L and M,
- $X_{19}$ is selected from N, S, T and Q,
- $X_{20}$ is selected from F, Y, W, A, V, I, L and M,
- $X_{21}$ is selected from F, Y, W, A, V, I, L and M,
- $X_{22}$ is selected from R, H and K,
- $X_{23}$ is selected from C, S and T,
- $X_{24}$ is selected from F, Y, W, A, V, I, L and M, and
- $X_{25}$ is selected from F, Y, W, A, V, I, L and M.

In at least one embodiment, the peptide compound comprises a derivative of peptide $CAP37_{20\text{-}44}$ having the following amino acid sequence (SEQ ID NO:12):

$$X_1X_2X_3X_4X_5X_6X_7X_8X_9X_{10}X_{11}X_{12}X_{13}X_{14}$$

$$X_{15}X_{16}X_{17}X_{18}X_{19}X_{20}X_{21}X_{22}X_{23}X_{24}X_{25}$$

wherein
- $X_1$ is selected from N, S, T and Q,
- $X_2$ is selected from N, S, T and Q,
- $X_3$ is selected from G, A and V,
- $X_4$ is selected from R, H and K,
- $X_5$ is selected from R, H and K,
- $X_6$ is selected from F, Y, W, A, V, I, L and M,
- $X_7$ is selected from C, S and T,
- $X_8$ is selected from G, A and V,
- $X_9$ is selected from G, A and V,
- $X_{10}$ is selected from F, Y, W, A, V, I, L and M,
- $X_{11}$ is selected from F, Y, W, A, V, I, L and M,
- $X_{12}$ is selected from F, Y, W, A, V, I, L and M,
- $X_{13}$ is selected from R, H and K,
- $X_{14}$ is selected from F, Y, W, A, V, I, L and M,
- $X_{15}$ is selected from R, H and K,
- $X_{16}$ is selected from F, Y, W, A, V, I, L and M,
- $X_{17}$ is selected from F, Y, W, A, V, I, L and M,
- $X_{18}$ is selected from F, Y, W, A, V, I, L and M,
- $X_{19}$ is selected from N, S, T and Q,
- $X_{20}$ is selected from F, Y, W, A, V, I, L and M,
- $X_{21}$ is selected from F, Y, W, A, V, I, L and M,
- $X_{22}$ is selected from N, S, T and Q,
- $X_{23}$ is selected from C, S and T,
- $X_{24}$ is selected from F, Y, W, A, V, I, L and M, and
- $X_{25}$ is selected from N, S, T and Q.

The peptide compounds may be administered alone or in combination with the other drug therapies and may be administered by a variety of administration routes. The particular mode selected will depend upon the compound selected, the condition being treated, the severity of the condition, whether the treatment is therapeutic or prophylactic, and the dosage required for efficacy. The methods of the present disclosure, generally speaking, may be practiced using any mode of administration that is medically acceptable, meaning any mode that produces effective levels of the active compounds without causing clinically unacceptable adverse effects. The administration may, for example, be oral, intraperitoneal, intra-cavity such as (but not limited to) rectal or vaginal, transdermal, topical, cutaneous, intranasal, inhalation, mucosal, interdermal, intraperitoneal, or parenteral routes. The term "parenteral" includes subcutaneous, intravenous, intramuscular, or infusion. In certain embodiments, it may be appropriate to administer the compound in a continuous infusion every several days, or once a week, or every several weeks, or once a month, or bimonthly, for example. Intravenous or intramuscular routes may be particularly used in emergency situations. Oral or intranasal administration may be used for prophylactic treatment because of the convenience to the patient as well as the dosing schedule. Likewise, sustained release devices may be useful in certain embodiments for prophylactic or post-surgery treatment, for example.

Particular pharmaceutical formulations of the presently disclosed peptide compositions include, but are not limited to, sterile aqueous or non-aqueous solutions, suspensions, and emulsions. Non-limiting examples of non-aqueous solvents include propylene glycol, polyethylene glycol, vegetable oils such as (but not limited to) olive oil, and injectable organic esters such as (but not limited to) ethyl oleate. Aqueous carriers include water, alcoholic/aqueous solutions, emulsions, or suspensions, including saline and buffered media. Parenteral vehicles include, for example, sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example (but not by way of limitation), antimicrobials, anti-oxidants, chelating compounds, inert gases, and the like. The pharmaceutical compositions may conveniently be presented in unit dosage form and may be prepared by any of the methods well known in the art of pharmacy.

Compositions suitable for oral administration may comprise discrete units, such as (but not limited to) capsules, pills, tablets, lozenges, melts, powders, suspensions, solutions, elixirs or emulsions, each containing a predetermined amount of the peptide composition. Other compositions include suspensions in aqueous liquids or non-aqueous liquids such as (but not limited to) syrup, an elixir, or an emulsion. In yet other embodiments, the particular vehicle is a biocompatible microparticle or implant that is suitable for implantation into the mammalian recipient.

Other embodiments of the peptide compositions include pharmaceutically acceptable compositions which comprise a therapeutically effective amount of one or more of the compounds described herein, formulated together with one or more pharmaceutically acceptable carriers (additives) and/or diluents. As described in detail herein, the pharmaceutically acceptable compositions may be specially formulated for administration in solid or liquid form, including, but not limited to, those adapted for the following: oral administration, for example, aqueous or non-aqueous solutions or suspensions, tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginal or intrarectal administration, for example, as a cream or foam; sublingual administration; ocular administration; transdermal administration; or nasal administration.

Some examples of materials which can serve as pharmaceutically-acceptable carriers include, but are not limited to: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

In solid dosage forms of the peptide compositions for oral administration (capsules, tablets, pills, powders, granules, and the like), the compound or compounds may be mixed with one or more pharmaceutically-acceptable carriers, including, but not limited to, sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose, and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as cetyl alcohol, glycerol monostearate, and non-ionic surfactants; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets, and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Liquid dosage forms for oral or nasal administration of the peptide compounds include, but are not limited to, pharmaceutically acceptable emulsions, microemulsions, solutions, suspensions, syrups, and elixirs. In addition to the active ingredient, the liquid dosage forms may contain inert diluents commonly used in the art, such as, for example (but not by way of limitation), water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Besides inert diluents, the oral compositions can also include adjuvants such as (but not limited to) wetting agents, emulsifying and suspending agents, sweetening, flavoring, coloring, perfuming, and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Generally, a therapeutically effective amount of a peptide of the present disclosure will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 µg/kg to about 2000 mg/kg, or from 1.0 µg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six, or more sub-doses, for example, administered separately at appropriate intervals throughout the day, optionally, in unit dosage forms. In some embodiments, the compositions are administered for more than 7 days, more than 10 days, more than 14 days, or more than 20 days. In still other embodiments, the peptide is administered over a period of weeks or months. In still other embodiments, the peptide is delivered on alternate days, for example, the agent may be delivered every two days, or every three days, or every four days, or every five days, or every six days, or every week, or every month.

In certain non-limiting embodiments, an effective amount or therapeutic dosage of a peptide compound of the present disclosure contains, sufficient active agent to deliver from about 0.001 µg/kg to about 100 mg/kg (weight of active agent/body weight of the subject). For example, the composition will deliver about 0.01 µg/kg to about 50 mg/kg, and more particularly about 0.1 µg/kg to about 10 mg/kg, and more particularly about 1 µg/kg to about 1 mg/kg. Practice of a method of the present disclosure may comprise administering to a subject an effective amount of the peptide compound in any suitable systemic and/or local formulation, in an amount effective to deliver the therapeutic dosage of the active agent. In certain embodiments, an effective dosage may be, in a range of about 1 µg/kg to about 1 mg/kg of the active agent.

Practice of the methods of the present disclosure may comprise administering to a subject a therapeutically effective amount of the peptide compound in any suitable systemic and/or local formulation, in an amount effective to deliver the dosages listed above. The dosage can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method of the present disclosure, the variant peptide compound is provided in an IV infusion in the range of from about 0.01 mg/kg to about 10 mg/kg of body weight once a day.

Oral formulations may be formulated such that the peptide compound passes through a portion of the digestive system before being released, for example it may not be released until reaching the small intestine, or the colon.

Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition may contain a solid carrier, such as a gelatin or an adjuvant. The tablet, capsule, and powder may contain from about 0.05 to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition particularly contains from about 0.005 to about 95% by weight of the active substance. For example, a dose of about 10 mg to about 1000 mg once or twice a day could be administered orally.

In another embodiment, the peptide compounds of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the peptide compound in an aqueous or non-aqueous pharmaceutically acceptable solvent which may also contain suspending agents, sweetening agents, flavoring agents, and preservative agents as are known in the art.

For parenteral administration, for example, the peptide compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives and buffers as are known in the art.

When an effective amount of the peptide compound is administered by intravenous, cutaneous, or subcutaneous injection, the compound is particularly in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the peptide compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical compositions of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the peptide compound selected, the condition to be treated, the stage of the condition, and other relevant circumstances using formulation technology known in the art, described, for example, in *Remington: The Science and Practice of Pharmacy*, $22^{nd}$ ed.

Additional pharmaceutical methods may be employed to control the duration of action of the peptide compound. Increased half-life and/or controlled release preparations may be achieved through the use of proteins or polymers to conjugate, complex with, and/or absorb the peptide compound as discussed previously herein. The controlled delivery and/or increased half-life may be achieved by selecting appropriate macromolecules (for example but not by way of limitation, polysaccharides, polyesters, polyamino acids, homopolymers, polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release.

Another possible method useful in controlling the duration of action of the peptide compound by controlled release preparations and half-life is incorporation of the peptide compound or its functional derivatives into particles of a polymeric material such as polyesters, polyamides, polyamino acids, hydrogels, poly(lactic acid), ethylene vinylacetate copolymers, copolymer micelles of, for example, polyethylene glycol (PEG) and poly(1-aspartamide).

It is also possible to entrap the peptide compounds in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the peptide compound is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

The peptide compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines, and substituted ethanolamines.

In certain embodiments, the present disclosure includes a peptide compound composition including: at least one peptide compound coupled directly or indirectly to a carrier molecule, wherein the at least one peptide of the peptide compound is from 20 to 50 amino acids in length.

In at least certain embodiments, the present disclosure is directed to the use of the full length CAP37, NE, and CG protein and/or peptide fragments thereof, and/or derivatives of such peptides, alone, in combination, or as peptide components of peptide compounds comprising non-peptide moieties (e.g., PEG molecules) for inhibition of the pro-inflammatory and neurotoxic effects of Aβ in Alzheimer's disease, cerebral amyloid angiopathy, and other neuroinflammatory conditions related to Aβ. In non-limiting examples, peptide compounds of the present disclosure include peptides having the amino acid sequences SEQ ID NOS:1-12 disclosed above.

Examples of CG-based, NE-based, and CAP37-based variant peptides that can be used in various embodiments of the peptide compounds of the present disclosure include, but are not limited to those shown in Table 4.

TABLE 4

Examples of CG-, NE-, and CAP37-based peptides and variants

| Peptide name | Amino Acid sequence | SEQ ID NO: |
|---|---|---|
| $CG_{119-144}$ | GTLCTVAGWGRVSMRRGTDTLREVQL | 1 |
| $CG_{119-144}$ C122S | GTLSTVAGWGRVSMRRGTDTLREVQL | 13 |
| $CG_{119-144}$ C122A | GTLATVAGWGRVSMRRGTDTLREVQL | 14 |
| $CG_{119-144}$ D137R: | GTLCTVAGWGRVSMRRGTRTLREVQL | 15 |
| $CG_{119-144}$ R140M | GTLCTVAGWGRVSMRRGTDTLMEVQL | 16 |
| $CG_{119-144}$ E141R: | GTLCTVAGWGRVSMRRGTDTLRRVQL | 17 |
| $CG_{119-144}$ EI41M: | GTLCTVAGWGRVSMRRGTDTLRMVQL | 18 |
| $CG_{119-144}$ E141L: | GTLCTVAGWGRVSMRRGTDTLRLVQL | 19 |
| $CG_{119-144}$ D137R, E141R: | GTLCTVAGWGRVSMRRGTRTLRRVQL | 20 |
| $CG_{119-144}$ R140M, E141R: | GTLCTVAGWGRVSMRRGTDTLMRVQL | 21 |
| $CG_{119-144}$ R140M, E141M: | GTLCTVAGWGRVSMRRGTDTLMMVQL | 22 |
| $CG_{119-144}$ AG135 and T136 | GTLCTVAGWGRVSMRRDTLREVQL | 23 |
| $CG_{119-144}$ + GT insertion between G135 and T136 | GTLCTVAGWGRVSMRRGGTTDTLREVQL | 41 |
| $CG_{119-144}$ E141PR | GTLCTVAGWGRVSMRRGTDTLRPRVQL | 43 |
| $CG_{119-144}$ D137R, E141PR | GTLCTVAGWGRVSMRRGTRTLRPRVQL | 44 |
| $NE_{119-145}$ | GVQCLAMGWGLLGRNRGIASVLQELNV | 2 |
| $NE_{119-145}$ C122A | GVQALAMGWGLLGRNRGIASVLQELNV | 24 |
| $NE_{119-145}$ I136D: | GVQCLAMGWGLLGRNRGDASVLQELNV | 25 |
| $NE_{119-145}$ E142R | GVQCLAMGWGLLGRNRGIASVLQRLNV | 26 |
| $NE_{119-145}$ E142L | GVQCLAMGWGLLGRNRGIASVLQLLNV | 27 |
| $NE_{119-145}$ I136R | GVQCLAMGWGLLGRNRGRASVLQELNV | 45 |
| $NE_{119-145}$ I136R, E142R | GVQCLAMGWGLLGRNRGRASVLQRLNV | 46 |
| $CAP37_{120-146}$: | GTRCQVAGWGSQRSGGRLSRFPRFVNV | 3 |
| $CAP37_{120-146}$ C123A | GTRAQVAGWGSQRSGGRLSRFPRFVNV | 28 |
| $CAP37_{120-146}$ Q131W | GTRCQVAGWGSWRSGGRLSRFPRFVNV | 29 |
| $CAP37_{120-146}$ S133R | GTRCQVAGWGSWRGGRLSRFPRFVNV | 30 |

TABLE 4 -continued

Examples of CG-, NE-, and CAP37-
based peptides and variants

| Peptide name | Amino Acid sequence | SEQ ID NO: |
|---|---|---|
| CAP37$_{120-146}$ R136D | GTRCQVAGWGSWRSGGDLSRFPRFVNV | 31 |
| CAP37$_{120-146}$ R139M: | GTRCQVAGWGSWRSGGRLSMFPRFVNV | 32 |
| CAP37$_{120-146}$ R142M | GTRCQVAGWGSWRSGGRLSRFPMFVNV | 33 |
| CAP37$_{120-146}$ R139M, R142M | GTRCQVAGWGSWRSGGRLSMFPMFVNV | 42 |
| CG$_{20-47}$ | IQSPAGQSRCGGFLVREDFVLTAAHCWG | 4 |
| CG$_{20-47}$ C29S | IQSPAGQSRSGGFLVREDFVLTAAHCWG | 34 |
| CG$_{20-47}$ C45S | IQSPAGQSRCGGFLVREDFVLTAAHSWG | 35 |
| CG$_{20-47}$ C29S, C45S | IQSPAGQSRSGGFLVREDFVLTAAHSWG | 36 |
| NE$_{20-44}$ | LRGGHFCGATLIAPNFVMSAAHCVA | 5 |
| NE$_{20-44}$ C26S | LRGGHFSGATLIAPNFVMSAAHCVA | 37 |
| NE$_{20-44}$ C42S | LRGGHFCGATLIAPNFVMSAAHSVA | 38 |
| NE$_{20-44}$ C26S, C42S | LRGGHFSGATLIAPNFVMSAAHSVA | 39 |
| CAP37$_{20-44}$ | NQGRHFCGGALIHARFVMTAASCFQ | 6 |
| CAP37$_{20-44}$C26S | NQGRHFSGGALIHARFVMTAASCFQ | 40 |

As shown in further detail below, the peptides of the present disclosure can be modified by the addition of R, K, and/or H moieties (e.g., 1-10 amino acids linked to the N- and/or C-terminal portion of the peptide) and "miniPEG" (AEEA, AEEEA, AEEP, and AEEEP) moieties linked to the N- and/or C-terminal portions of the tagged or untagged peptide sequences. Examples of such miniPEG moieties are shown, for example, in International Patent Publications WO2014/089088 and WO2014/172747, and U.S. Pat. Nos. 9,624,283, and 9,862,748.

In certain embodiments, the peptide compounds of the present disclosure are represented by Formula (I):

S—X$_R$-Pep-Y$_R$   (I)

wherein Pep is an amino acid sequence disclosed or described herein (e.g., SEQ ID NOS:1-46); X$_R$ and Y$_R$ are each independently 0, 1, 2, 3, 4, 5, 6, 7, 8, 9, or 10 R, K, or H residues, for example where X$_R$+Y$_R$=up to 10; and S is a solubilizing moiety made up of 1, 2, 3, 4, 5, 6, 7, 8, 9, or 10 (i.e., 1-10) short PEG subunits such as AEEA, AEEP, AEEEA, and AEEEP, as defined elsewhere herein, in any combination.

The —O(CH$_2$)$_q$CO— portion ("head group") of the PEG subunit (S) which is attached to the peptide (X$_R$-Pep-Y$_R$) may be further modified to comprise a number of alternate embodiments of the (CH$_2$)$_q$ portion of the head group. These alternate embodiments, as well as those described above, can be characterized by Formula (II):

—O(CR$_1$R$_2$)$_q$CO—   (II)

wherein R$_1$ and R$_2$ of Formula II are side groups on C (i.e., "R$_1$—C—R$_2$") wherein q=0-4, and R$_1$ and R$_2$ are selected from H, CH$_3$, and CH$_2$CH$_3$. When q=1, either or both of R$_1$ and R$_2$ can be selected from H, CH$_3$, and CH$_2$CH$_3$. When q=2, either of the two R$_1$ groups and either of the two R$_2$ groups can be selected from H, CH$_3$, and CH$_2$CH$_3$. When q=3, any of the three R$_1$ groups and any of the three R$_2$ groups can be selected from H, CH$_3$, and CH$_2$CH$_3$. When q=4, any of the four R$_1$ groups and any of the four R$_2$ groups can be selected from H, CH$_3$, and CH$_2$CH$_3$. Thus, in these non-limiting embodiments, the head group may comprise one or more substitutions for H on the carbons of the carbon backbone when C=1-4.

Examples of embodiments of head groups having Formula II include, but are not limited to:
1. —OCH$_2$ CH$_2$CO— (e.g., as in AEEP).
2. —OCH$_2$CO— (e.g., as in AEEA).
3. —OCH$_2$ CH$_2$ CH$_2$CO— (wherein q=3).
4. —OCH$_2$ CH$_2$ CH$_2$ CH$_2$CO— (wherein q=4 i.e., a pentanoic head group).
5. —OC(CH$_3$)$_2$CO— (wherein R$_1$ and R$_2$=CH$_3$ and q=1).
6. —OCH$_2$C(CH$_3$)$_2$CO— (wherein R$_1$ and R$_2$=H on the first carbon and R$_1$ and R$_2$=CH$_3$ on the second carbon and q=2).
7. —OCH$_2$ CH$_2$ CH$_2$CH(CH$_3$)CO— (wherein R$_1$=H and R$_2$=CH$_3$ on one carbon, and R$_1$ and R$_2$=H on every other carbon and q=4).
8. —OCH$_2$ CH$_2$ CH$_2$C(CH$_3$)$_2$CO— (wherein R$_1$ and R$_2$=CH$_3$ on one carbon, and R$_1$ and R$_2$=H on all other carbons).
9. —OCH$_2$ CH$_2$ CH$_2$CH(CH$_2$CH$_3$)CO— (wherein R$_1$=H and R$_2$=CH$_2$CH$_3$ on one carbon, and R$_1$ and R$_2$=H on all other carbons).
10. —OCH(CH$_3$) CH$_2$ CH$_2$CH(CH$_2$CH$_3$)CO— (wherein R$_1$=H and R$_2$=CH$_3$ on one carbon, R$_1$=H and R$_2$=CH$_2$CH$_3$ on one carbon, and R$_1$ and R$_2$=H on all other carbons).

All stereoisomers of the peptide compounds formed based on the solubilizing units described for Formula II are intended to be included in the present disclosure.

EXPERIMENTAL

Methods

Binding Assay

Enzyme-linked Immunosorbent Assay (ELISA) was used to quantify the binding of Aβ to CAP37, CAP37-derived peptides, NE, CG, and BSA (used as a negative control). CAP37, NE, and CG were purified from human neutrophils and purchased from Athens Research and Technology. BSA was from Sigma Aldrich. CAP37-derived peptides were synthesized by CS Bio Co with a purity >95%. Maxisorp plates from Nunc were coated with 100 μl neutrophil protein, peptide, or BSA diluted at 5 μg/ml in PBS with or without 1 mM PMSF purchased from Sigma Aldrich (for experiments with CAP37, NE, and BSA) or ±125 μM chymostatin purchased from Santa Cruz (for experiments with CG and BSA). Plate coating was done at room temperature for 2 hours with shaking and then at 4° C. overnight. Plates were washed three times in PBST (PBS+0.05% tween), then blocked with 3% BSA in PBST for 1 hour at room temperature with shaking. Plates were washed 3× in PBST, and 150 nM Aβ$_{1-42}$ (purchased from Bachem and reconstituted in 1 mM NaOH) was added in 0.1% BSA in PBST and incubated 70 minutes at 37° C. Plates were then washed 4 times with PBST and monoclonal mouse anti-amyloid precursor protein/amyloid beta antibody, purchased from Cell Signaling Technology was added at a 1:500 dilution in 1% BSA in PBST and incubated for 1 hour at room temperature with shaking. Plates were washed 4× in PBST and donkey anti mouse HRP-conjugated secondary antibody from Jackson ImmunoResearch Laboratories was added at 1:10,000 in PBST and incubated 1 hour at room temperature with shaking, then washed 4 times in PBST. Substrate buffer (49 mM citric acid, 102 mM sodium phosphate, pH adjusted to 5.0 with HCl, with 7.5 mM substrate o-phenylenediamine from Kodak, and 0.024% final $H_2O_2$ freshly added) was added to the plate and incubated for 30 minutes in the dark. Sulfuric acid (5N) was added to each well to stop the reaction, and the absorbance at 492 nm was read on a Biotek Synergy II plate reader.

Amyloid Beta (Aβ) Fibrillation Assay

The Amyloid Beta (1-42) Thioflavin T Aggregation Kit was purchased from Anaspec and used to monitor the formation of $A\beta_{1-42}$ peptide fibrils, according to the manufacturer's instructions, with some modifications. Thioflavin T dye was diluted to 250 µM in fibrillation buffer A and kept in the dark until use. $A\beta_{1-42}$ peptide was suspended at 250 µg/ml (or 55 (0.1 µM) in buffer A, incubated on ice 5 min, mixed by inversion of the tube multiple times, sonicated 5 minutes in a water bath sonicator at 4° C., mixed again, and centrifuged 5 minutes at 10,000×g. The supernatant was transferred to a new tube and stored at 4° C. until use. Inhibitors of aggregation CAP37, CAP37-derived peptides, NE, CG and BSA (used as negative control) were diluted in water to 20× the desired final concentration. In low light, 10 µl Thioflavin T dye was added to low-protein-binding black plates from Corning, 85 µl $A\beta_{1-42}$ prepared in Buffer A and 5 µl water or inhibitor of aggregation to be tested were also added. Neutrophil proteins were tested in the absence and presence of protease inhibitors. PMSF was dissolved in 100% ethanol and used at 1 mM final concentration in reactions with CAP37 and NE. Chymostatin was dissolved in DMSO and used at 125 µM final concentration in reactions with CG. Reactions were pipetted up and down twice in the wells with a multichannel pipette to ensure mixing, and fluorescence ($\Delta_{EX}$=440 nm, $\Delta_{Em}$=485 nm) was read every 5 minutes for 3 hours on a BioTek Synergy 2 plate reader with Gen 5 software, with a sensitivity set at 65.

Enzyme Activity Assay $A\beta_{1-42}$ treated with hexafluoroisopropanol was purchased from Bachem and reconstituted in anhydrous DMSO at 5 mM. Reactions were set up with increasing concentrations of enzyme (CAP37, NE or CG) and 10 µM $A\beta_{1-42}$ substrate in PBS, and incubated at 37° C. for 1 hour. Reactions were stopped by the addition of acetonitrile and trifluoroacetic acid (TFA) to final concentrations of 7.5% and 0.5% respectively. Internal standard ($A\beta_{40-1}$ from Bachem) dissolved in 10% acetic acid was added to a final concentration of 8 µg/ml. A 10 µl aliquot of this mixture was desalted on a C18 OMIX tip from Agilent Technologies. First, the C18 resin was rinsed with 2×10 µl of 50% methanol, then 2×10 µl of equilibration buffer (5% acetonitrile 0.5% TFA), then the sample was applied to the resin by pipetting 10 times through the resin, which was then washed twice with equilibration buffer and eluted with 75% acetonitrile 0.1% TFA.

Desalted samples were analyzed by Matrix Assisted Laser Desorption/Ionization-Time of Flight mass spectrometry (MARLDI-TOF) using a Bruker Ultraflex II instrument and Flex Control Software. Samples were spotted on a steel plate with 1 µl of α-cyano-4-hydroxycinnamic acid matrix in 30% acetonitrile 0.1% TFA. Each sample was spotted in triplicate. The plate was dried in a vacuum desiccator. Each chromatograph was the average of 5×200 shots at 28% laser power in Linear Positive Mode. Chromatographs were analyzed with Flex Analysis software. The chromatographs had a peak at around 4,330 m/z which corresponds to the Aβ40.1 internal standard and a peak at around 4,515 m/z, which corresponds to the $A\beta_{1-42}$ substrate. The ratio of the $A\beta_{1-42}$ peak intensity divided by the internal standard peak intensity was calculated for each spot, and triplicate spots were averaged to determine the amount of uncleaved Aβ in each enzymatic reaction.

Cell Culture and Neurotoxicity Assay

A mouse neuroblastoma cell line Neuro-2a from ATCC was used for these experiments. Cells were grown and seeded in 96 well plates at 20,000 cells per well in complete medium (MEM α, nucleosides, no phenol red from Gibco, with 10% heat inactivated fetal bovine serum from Gibco, and penicillin/streptomycin from Lonza). At 24 hours after seeding, cells were washed with warmed MEM α, and then incubated in 90 µl MEM α+N2 Supplements+20 µl test sample ($A\beta_{1-42}$ prepared as described below). Cells were incubated another 24 hours at 37° C., and then dislodged by pipetting up and down vigorously. 10 µl of cells were added to 10 µl trypan blue dye (0.4% solution) from BioRad, mixed and counted in a BioRad TC20 cell counter. The percent of living and dead cells was recorded for each well. In the case of the water and Triton X100 controls, 20 µl MEM α+N2 Supplements was added instead of the test sample and, just before counting the cells, 20 µl of medium was removed and replaced with 20 µl water or Triton X100 at a final concentration of 0.1%.

Preparation of Aβ, Monomer, Fibril, and Oligomer Test Samples

Monomeric $A\beta_{1-42}$ (hexafluoroisopropanol treated $A\beta_{1-42}$) from Bachem was reconstituted at 5 mM in anhydrous DMSO. Untreated $A\beta_{1-42}$ from CS Bio was also used in these experiments. It was first treated with 1 mM in hexafluoroisopropanol from Sigma Aldrich, incubated 30 min at room temperature, and left open to dry in the fume hood overnight. It was then vacuum desiccated for 1 hour at room temperature. Dry films of $A\beta_{1-42}$ were stored at –20° C. until use to keep it under a monomeric form. $A\beta_{1-42}$ from CS Bio was also reconstituted in anhydrous DMSO at 5 mM before use.

Toxicity of $A\beta_{1-42}$ monomers was tested by diluting freshly prepared $A\beta_{1-42}$ (5 mM in DMSO) in MEM α+N2 Supplements, at a final concentration of 18 µM. This mixture was used to replace the complete growth medium on the cells at 24 hours after seeding, and the toxicity of $A\beta_{1-42}$ monomers was measured after 24 hours incubation.

To prepare the fibril and oligomer test samples, monomeric $A\beta_{1-42}$ was placed under conditions favoring either formation of fibrils or oligomers. To form fibrils, 100 µM $A\beta_{1-42}$ was added to Anaspec fibrillation buffer A±neutrophil protein, and incubated at 37° C. 24 hours before addition to the cells at a final concentration of 18 µM. Neutrophil proteins were used at Aβ/Protein ratios that led to 50% inhibition of fibrillation (IC50), previously determined for each protein in the fibrillation assay. To form oligomers, MEM α+N2 Supplements was used instead of the fibrillation buffer A±increasing concentrations of neutrophil protein or CAP37-derived peptide. Each mixture was then added to a tube containing freshly prepared $A\beta_{1-42}$ in DMSO at a final concentration of 100 µM, and incubated 15 min at room temperature. These test samples were then tested on the cells at a final concentration of 18 µM.

Results

Figure 2:
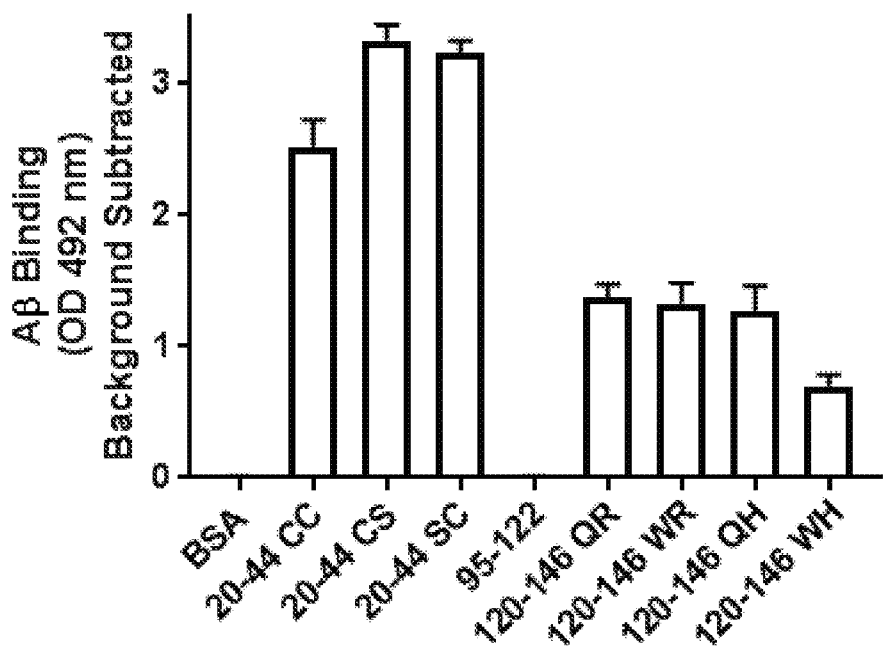
FIG. 2 shows levels of binding of $A\beta_{1-42}$ to wild-type CAP37-derived peptides 20-44 (20-44 CC, 95-122, and 120-146 QR) and to mutant CAP37-derived peptides (20-44 CS, 20-44 SC, 120-146 WR, 120-146 QH, and 120-146 WH). $A\beta_{1-42}$ did not bind to peptide 95-122.
Figure 3:
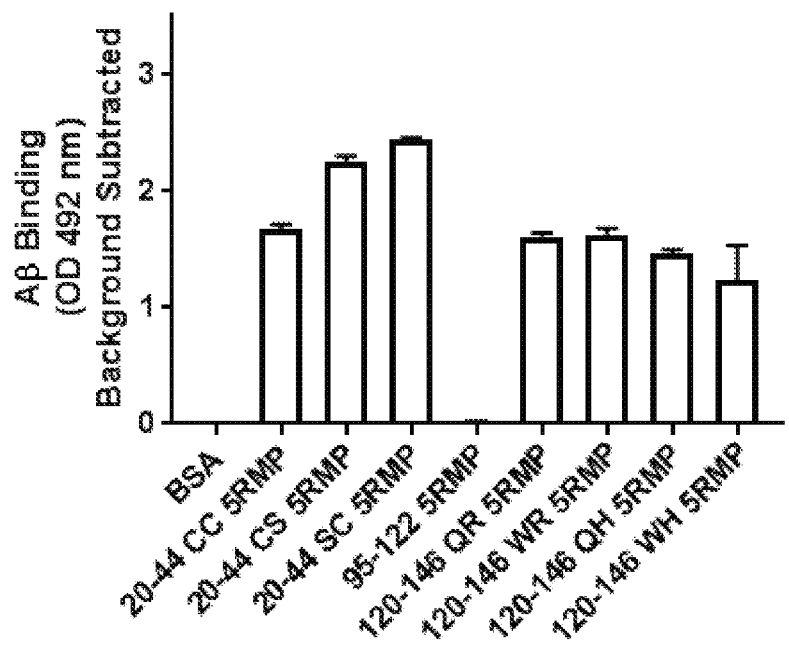
FIG. 3 shows levels of $A\beta_{1-42}$ binding to "5RMP"-modified CAP37-derived peptides of FIG. 2 (two AEEA mini-PEG molecules and 4 consecutive arginines linked to the N-terminal end of the peptide and one arginine linked to the C-terminal end of the peptide).

FIG. 1 shows binding of $A\beta_{1-42}$ to full-length CAP37, NE, and CG proteins. The binding is stronger with CAP37 and CG, and is not significantly changed by the addition of antiproteases (phenylmethylsulfonyl fluoride (PMSF) or chymostatin). The binding of $A\beta_{1-42}$ to NE is almost undetectable, but significantly increased in the presence of PMSF, which inhibits the cleavage of $A\beta_{1-42}$ by NE. These results show a stronger $A\beta_{1-42}$ binding to CAP37 and CG, and a weaker binding to NE. FIG. 2 shows levels of binding of $A\beta_{1-42}$ to wild-type CAP37-derived peptides 20-44 (20-44 CC, 95-122, and 120-146 QR) and to mutant CAP37-derived peptides (20-44 CS, 20-44 SC, 120-146 WR, 120-146 QH, and 120-146 WH). $A\beta_{1-42}$ did not bind to peptide 95-122. FIG. 3 shows levels of $A\beta_{1-42}$ binding to "5RMP"-modified CAP37-derived peptides of FIG. 2 (two AEEA mini-PEG molecules and 4 consecutive arginine residues linked to the N-terminal end of the peptide and one arginine linked to the C-terminal end of the peptide). These results show that $A\beta_{1-42}$ binds to wild-type and mutant CAP37-derived peptides 20-44 and 120-146 with or without the "5RMP" modification, but not to peptide 95-122 with or without the "5RMP" modification.

Figure 4:
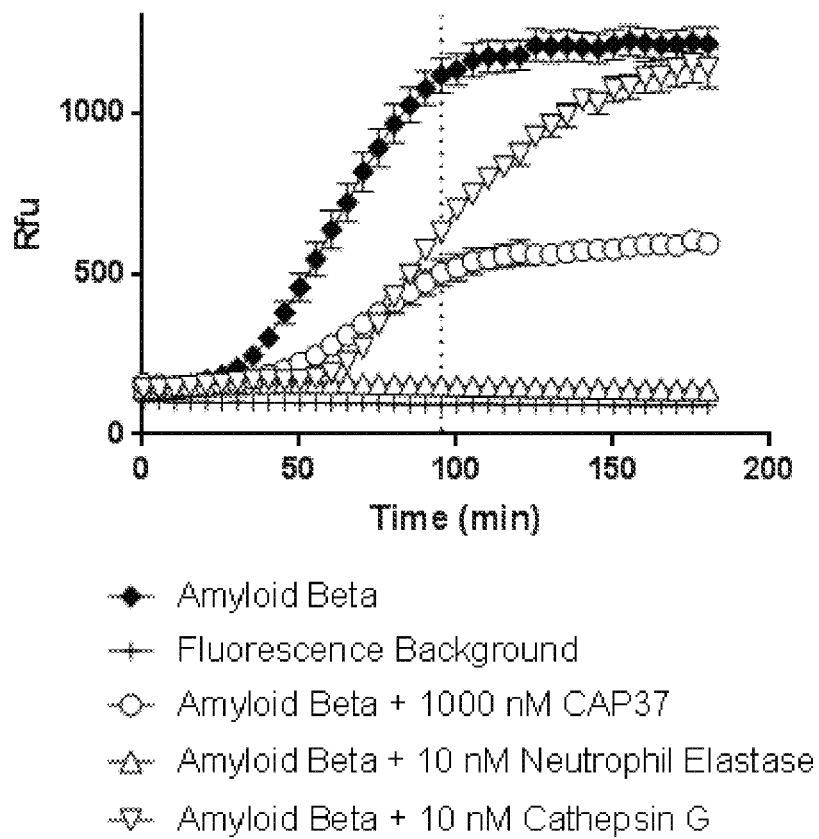
FIG. 4 is a graph showing levels of fibrillation (aggregation) of $A\beta_{1-42}$ in the presence of indicated concentrations of full-length CAP37, NE, or CG. The time of complete fibrillation of $A\beta_{1-42}$ (when no protein is added) is indicated by the vertical dotted line.
Figure 5:
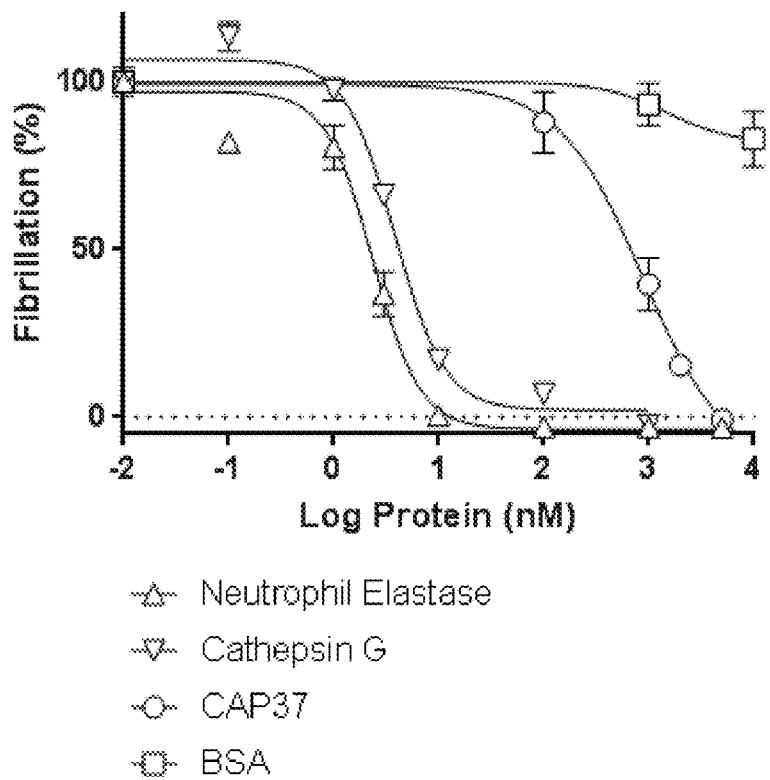
FIG. 5 is a graph showing levels of fibrillation (aggregation) of $A\beta_{1-42}$ in the presence of full-length CAP37, NE, or CG at varying concentrations of protein. NE has the highest inhibitory effect on $A\beta_{1-42}$ fibrillation, followed by CG, then by CAP37.

FIGS. 4-7, 10, and 13 show fibrillation of $A\beta_{1-42}$, recorded as relative fluorescence unit (Rfu), in the absence and presence of increasing concentrations of the three neutrophil granule proteins and specific wild-type and mutant CAP37-derived peptides. FIG. 4 shows levels of fibrillation (aggregation) of $A\beta_{1-42}$ in the presence of indicated concentrations of full-length CAP37, NE, or CG. The time of complete fibrillation of $A\beta_{1-42}$ (when no protein is added) is indicated by the vertical dotted line. Fibrillation is either partially or completely inhibited in the presence of these proteins. FIG. 5 shows levels of fibrillation (aggregation) of $A\beta_{1-42}$ in the presence of full-length CAP37, NE, or CG at varying concentrations of protein. NE has the highest inhibitory effect on $A\beta_{1-42}$ fibrillation, followed by CG, then by CAP37. FIG. 5 shows a dose-response performed with each full-length protein. Percent fibrillations shown in FIG. 5 were calculated at time points corresponding to complete fibrillation of the $A\beta_{1-42}$ control, as indicated by the dotted line in FIG. 4. These dose-response experiments show that NE has the highest inhibitory effect on $A\beta_{1-42}$ fibrillation (with an IC50 of 2.4 nM corresponding to a molar ratio for NE/$A\beta_{1-42}$ of 1/4,167), followed by CG (IC50 of 3.8 nM; molar ratio of 1/2,632) and CAP37 (IC50 of 876 nM; molar ratio of 1/11).

Figure 6:
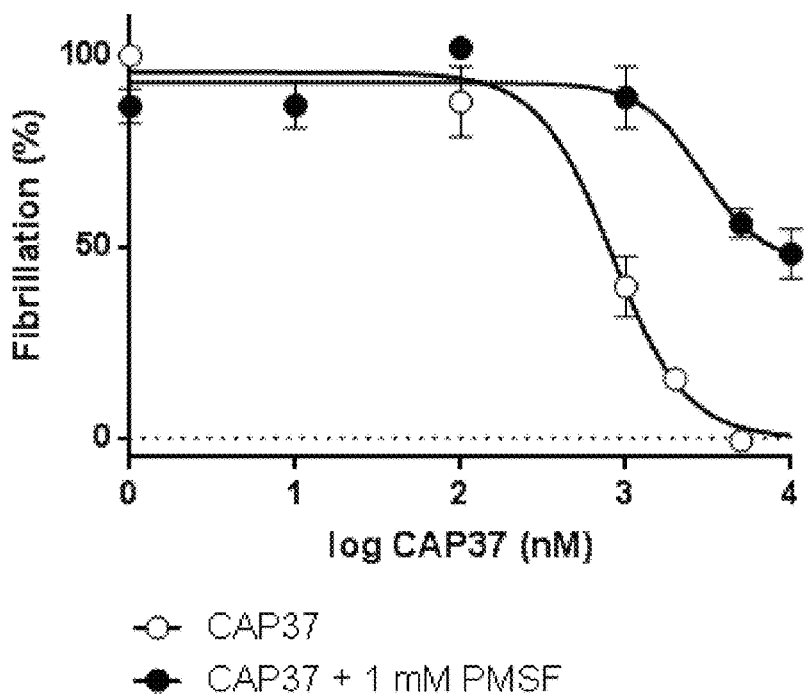
FIG. 6 shows that the protease inhibitor PMSF impairs the inhibitory effects of CAP37 on $A\beta_{1-42}$ fibrillation. The IC50 of CAP37 is increased by 3.5-times in the presence of PMSF. This indicates that the inhibitory effect of CAP37 on fibrillation is due, at least partially, to the cleavage of $A\beta_{1-42}$.
Figure 7:
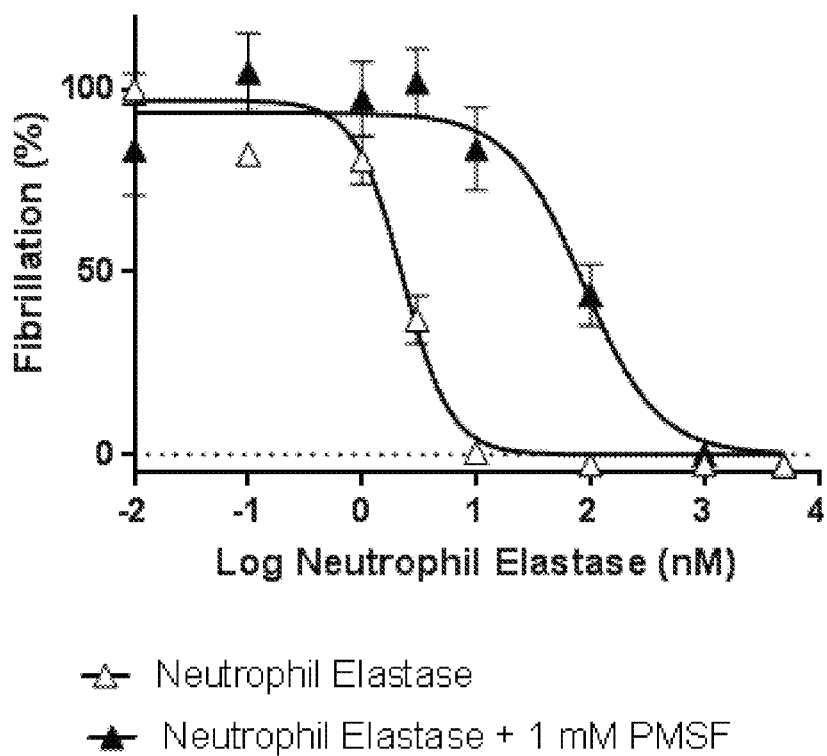
FIG. 7 shows that the protease inhibitor PMSF impairs the inhibitory effects of NE on $A\beta_{1-42}$ fibrillation. The IC50 of NE is increased by 36-times in the presence of PMSF. This indicates that the inhibitory effect of NE on fibrillation is due, at least partially, to the cleavage of $A\beta_{1-42}$.
Figure 13:
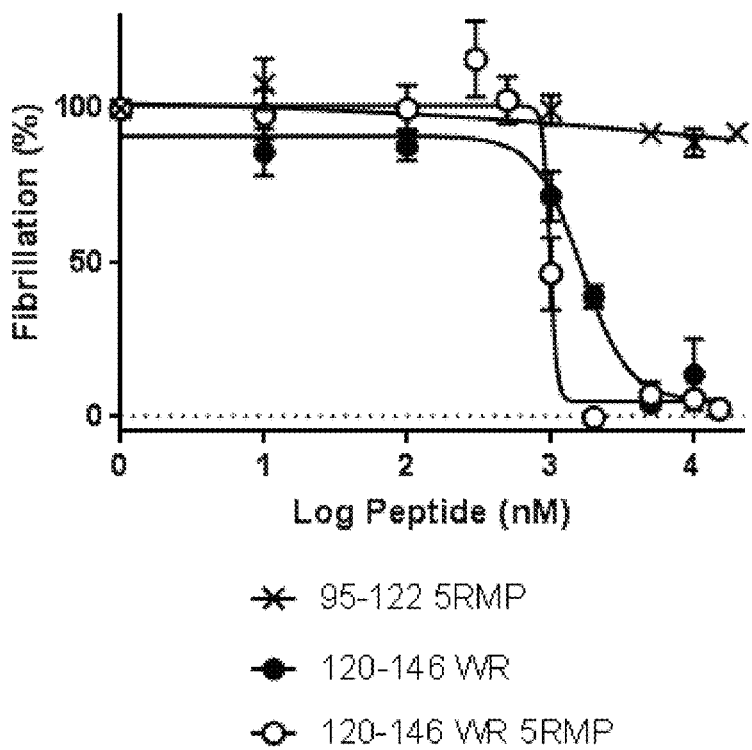
FIG. 13 shows that CAP37-derived peptides 120-146 WR and 120-146 WR 5RMP inhibit. Peptide 95-122 5RMP does not inhibit fibrillation.

FIG. 6 shows that the protease inhibitor PMSF impairs the inhibitory effects of CAP37 on $A\beta_{1-42}$ fibrillation. The IC50 of CAP37 is increased by 3.5-times in the presence of PMSF. This indicates that the inhibitory effect of CAP37 on fibrillation is due, at least partially, to the cleavage of $A\beta_{1-42}$. FIG. 7 shows that the protease inhibitor PMSF impairs the inhibitory effects of NE on $A\beta_{1-42}$ fibrillation. The IC50 of NE is increased by 36-times in the presence of PMSF. This indicates that the inhibitory effect of NE on fibrillation is due, at least partially, to the cleavage of $A\beta_{1-42}$. The three neutrophil granule proteins were previously found to cleave $A\beta_{1-42}$ so in FIGS. 6, 7, and 10, CAP37, NE and CG were tested in the absence and presence of adequate protease inhibitor (PMSF for CAP37 and NE, and chymostatin for CG) to determine if the cleavage of $A\beta_{1-42}$ is necessary for inhibition of fibrillation. In all three experiments, inhibition of the enzymatic cleavage of $A\beta_{1-42}$ also impaired the inhibitory effects of these proteins on fibrillation. This indicates that the inhibitory effects on fibrillation are due, at least partially, to the cleavage of $A\beta_{1-42}$. FIG. 13 shows a dose-response performed with increasing concentrations of CAP37-derived peptides 95-122 5RMP, 120-146 WR 5RMP, and 120-146 WR. Peptide 95-122 5RMP does not interact with $A\beta_{1-42}$ (FIG. 3) and did not inhibit fibrillation. Peptides 120-146 WR 5RMP and 120-146 WR both interact with $A\beta_{1-42}$ (FIGS. 2 and 3) and were able to inhibit fibrillation. The inhibitory effects of these CAP37-derived peptides were similar to that of the full-length CAP37 (IC50s of ~1000 nM; molar ratios of ~1/10) even though the peptides do not have enzymatic activities on $A\beta_{1-42}$. Without wishing to be bound by theory, this indicates that cleavage of $A\beta_{1-42}$ is not the only mechanism for inhibition of $A\beta_{1-42}$ fibrillation. Direct binding to $A\beta_{1-42}$ appears to also play a role in inhibition of fibrillation.

Figure 8:
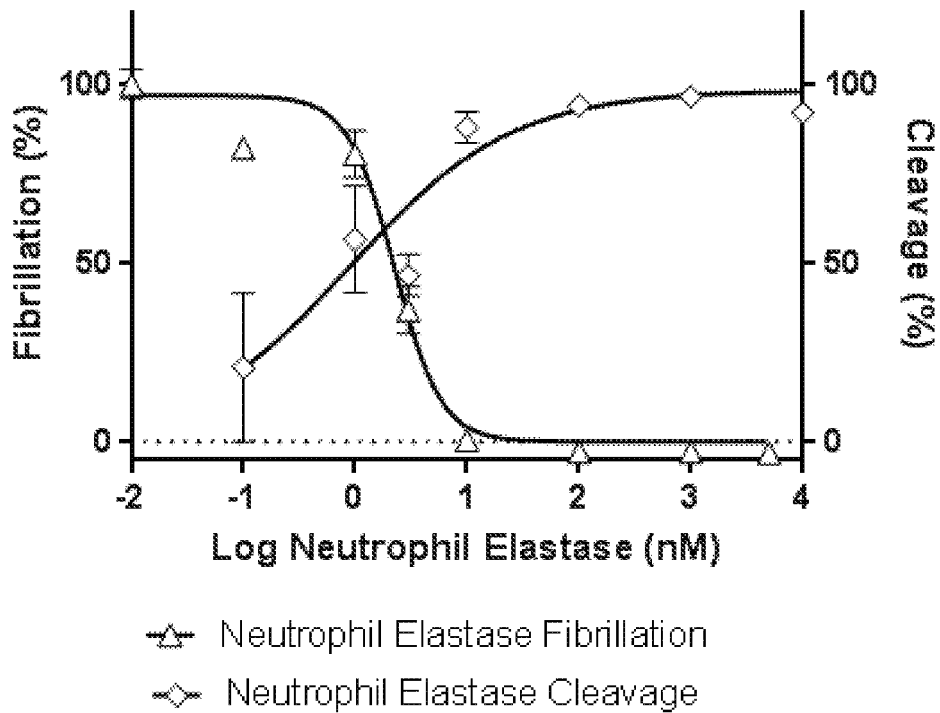
FIG. 8 shows a direct correlation between the cleavage of $A\beta_{1-42}$ and the inhibition of fibrillation by NE. This correlation supports the notion that NE's inhibition of fibrillation is mainly mediated by the cleavage of Aβ. This experiment was performed in the absence of PMSF.
Figure 9:
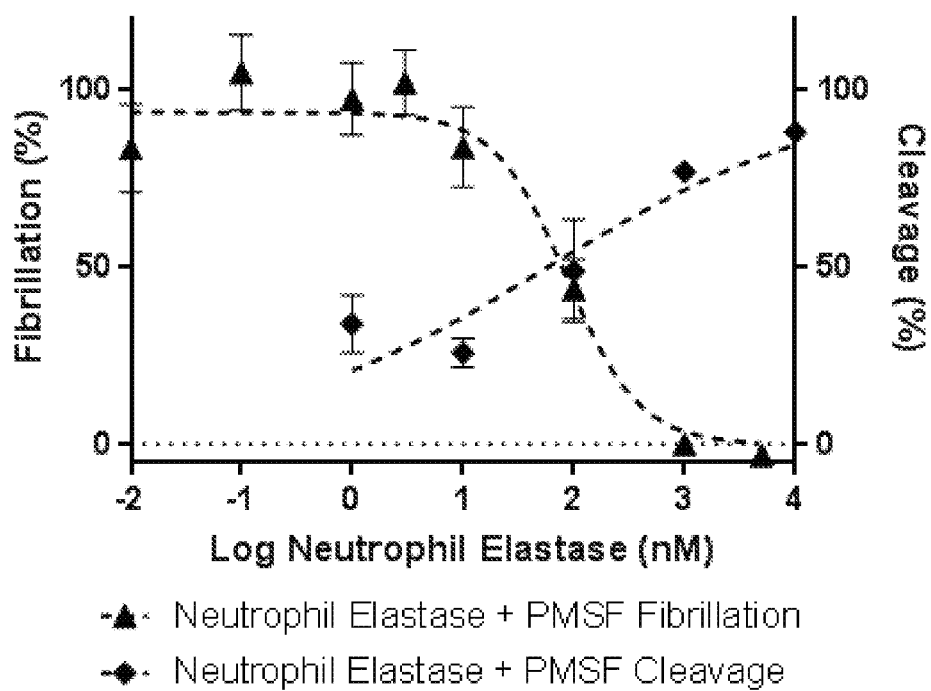
FIG. 9 shows a direct correlation between the cleavage of $A\beta_{1-42}$ and the inhibition of fibrillation by NE. This experiment was performed in the presence of PMSF.
Figure 10:
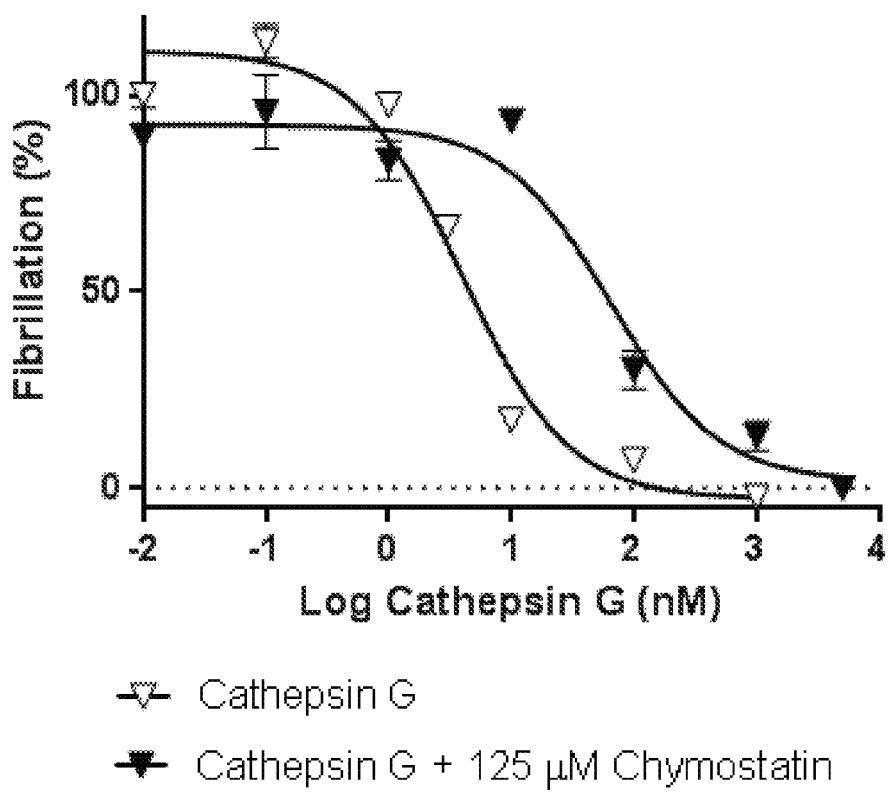
FIG. 10 shows that the protease inhibitor chymostatin impairs the inhibitory effects of CG on $A\beta_{1-42}$ fibrillation. The IC50 of CG is increased by 17-times in the presence of chymostatin. This indicates that the inhibitory effect of CG on fibrillation is due, at least partially, to the cleavage of $A\beta_{1-42}$.
Figure 11:
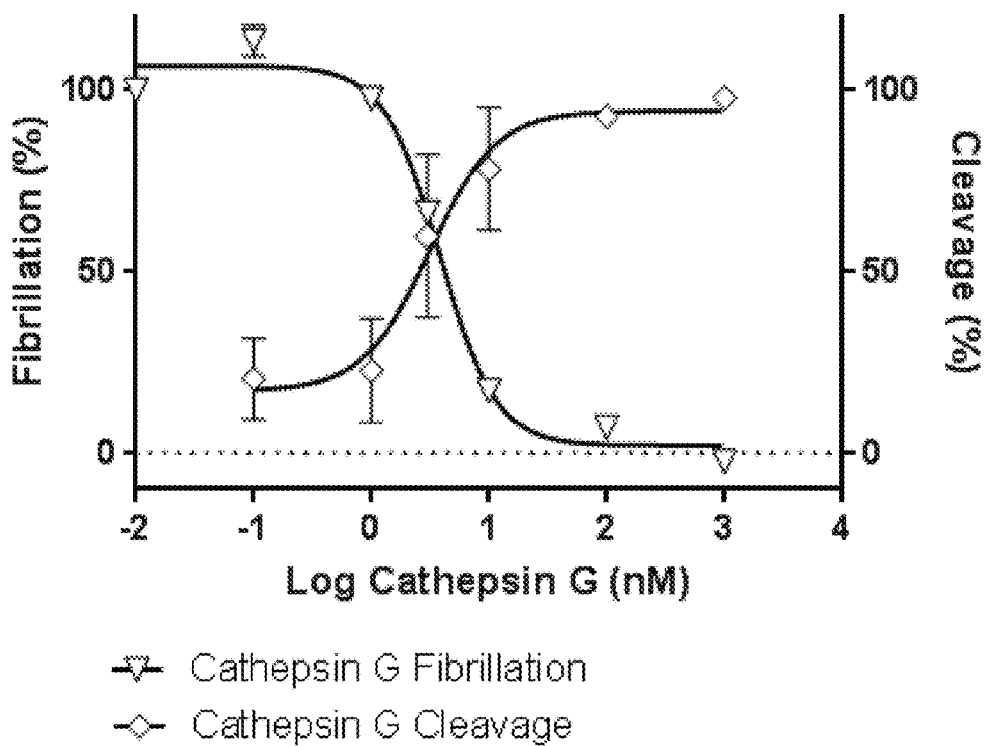
FIG. 11 shows a direct correlation between the cleavage of $A\beta_{1-42}$ and the inhibition of fibrillation by CG. This correlation supports the notion that CG's inhibition of fibrillation is mainly mediated by the cleavage of $A\beta$. This experiment was performed in the absence of chymostatin.
Figure 12:
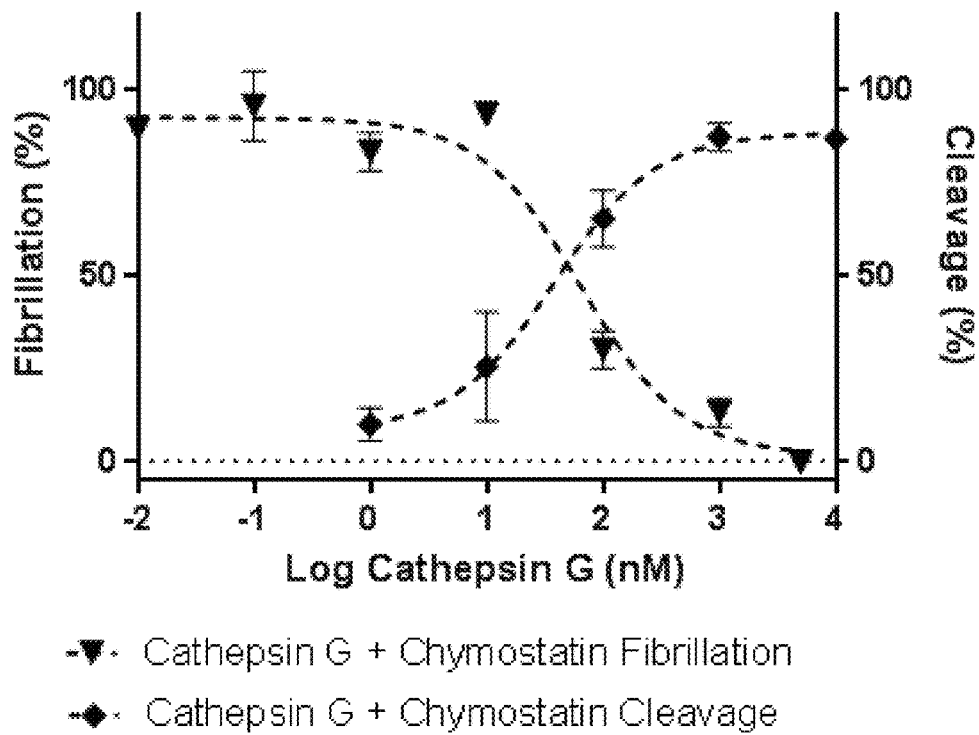
FIG. 12 shows a direct correlation between the cleavage of $A\beta_{1-42}$ and the inhibition of fibrillation by CG. This experiment was performed in the presence of chymostatin.

FIGS. 8, 9, 11, and 12 show percent fibrillation and corresponding percent cleavage of $A\beta_{1-42}$ on the right y-axis, in experiments performed with increasing concentrations of the full-length neutrophil granule proteins, in the absence and presence of protease inhibitors. FIG. 8 shows a direct correlation between the cleavage of $A\beta_{1-42}$ and the inhibition of fibrillation by NE. This correlation supports the notion that NE's inhibition of fibrillation is mainly mediated by the cleavage of $A\beta$. This experiment was performed in the absence of PMSF. FIG. 9 shows a direct correlation between the cleavage of $A\beta_{1-42}$ and the inhibition of fibrillation by NE. This experiment was performed in the presence of PMSF. FIG. 11 shows a direct correlation between the cleavage of $A\beta_{1-42}$ and the inhibition of fibrillation by CG. This correlation supports the notion that CG's inhibition of fibrillation is mainly mediated by the cleavage of $A\beta$. This experiment was performed in the absence of chymostatin. FIG. 12 shows a direct correlation between the cleavage of $A\beta_{1-42}$ and the inhibition of fibrillation by CG. This experiment was performed in the presence of chymostatin. These results establish a direct correlation between cleavage and inhibition of fibrillation, supporting the notion that cleavage of $A\beta_{1-42}$ is the main mechanism explaining inhibition of fibrillation mediated by the full-length proteins.

Figure 14:
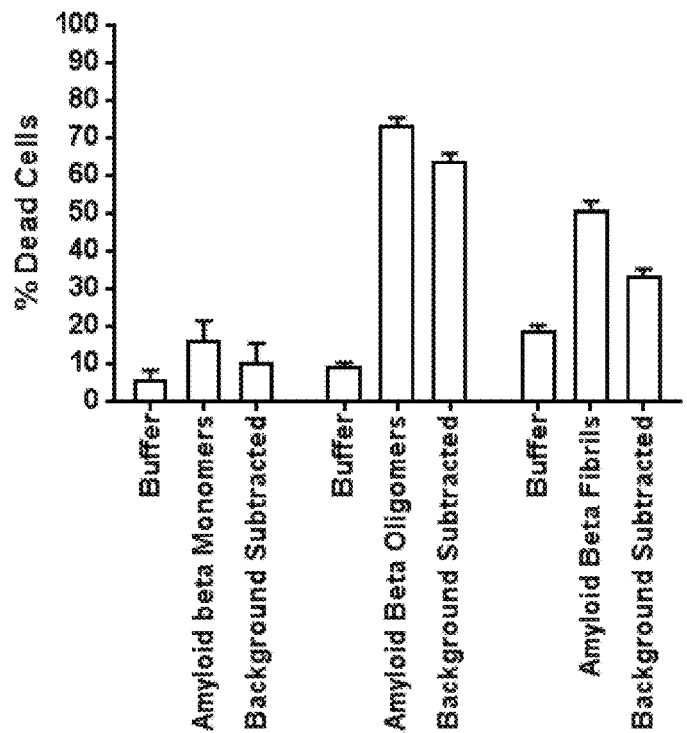
FIG. 14 shows that $A\beta_{1-42}$ oligomers are more toxic than fibrils on neurons. The monomeric form of $A\beta_{1-42}$ is the least toxic.

FIG. 14 shows the toxicity of various conformations of $A\beta_{1-42}$ in neurons. Conditions favoring monomer, oligomer or fibril conformations of $A\beta_{1-42}$ were used. FIG. 14 shows that $A\beta_{1-42}$ oligomers are more toxic than fibrils on neurons. The monomeric form of $A\beta_{1-42}$ is the least toxic. These results confirm previously published results by other groups, showing the highest toxicity for oligomers, followed by fibrils, and then monomers.

Figure 15:
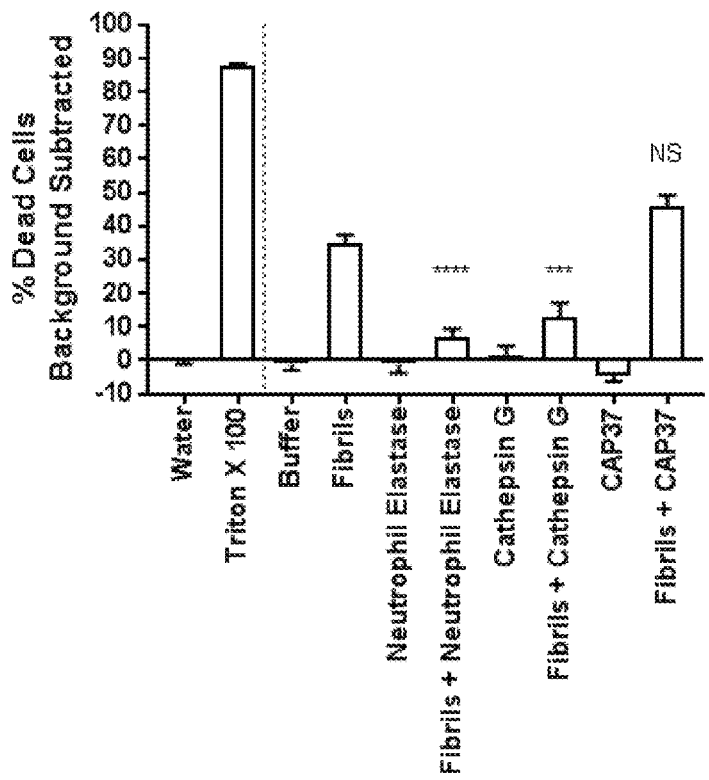
FIG. 15 shows that NE and CG, but not CAP37, inhibit the toxicity of Aβ1-42, when incubated under conditions that favor fibril formation.

FIG. 15 shows that NE and CG, but not CAP37, inhibit the toxicity of $A\beta_{1-42}$, when incubated under conditions that favor fibril formation. FIG. 15 shows the toxicity of $A\beta_{1-42}$ fibrils, formed in the absence or presence of neutrophil granule proteins, used at concentrations that inhibit approximately 50% of fibrillation (IC50s), previously determined for each protein in FIG. 5. This experiment shows significant inhibition of fibril toxicity by NE and CG. CAP37 appears to have no effect on the toxicity of $A\beta_{1-42}$ under these conditions. In experiments with fibrils, all three neutrophil granule proteins are pre-incubated with $A\beta_{1-42}$ for 24 hours before addition to the cells. The percent cleavage of $A\beta_{1-42}$ during this 24 hours fibrillation step is likely to be more than 50%. Cleavage is important for the inhibition of fibrils toxicity, in the case of NE and CG. By contrast, the cleavage of $A\beta_{1-42}$ by CAP37 is involved in the inhibition of fibrillation as determined in FIG. 6, but is not able to inhibit the toxicity of $A\beta_{1-42}$, when preincubated in fibrillation conditions. This could be explained by the fact that NE and CG have more cleavage sites than CAP37 on $A\beta_{1-42}$, generating smaller products. It is thus possible that the larger products generated by CAP37 cleavage are still able to form toxic aggregates under fibrillation conditions.

Figure 16:
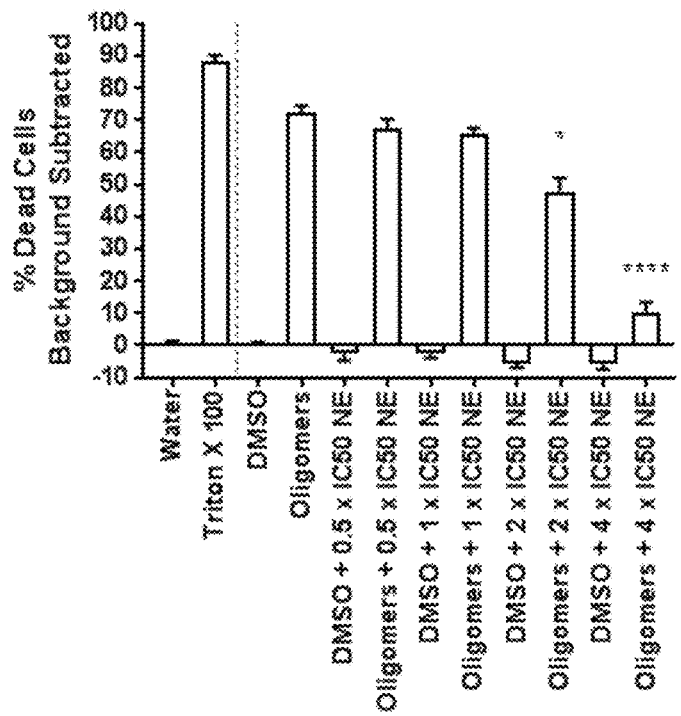
FIG. 16 shows effects of $A\beta_{1-42}$ oligomers on neuron cells in the presence of varying concentrations of NE. NE significantly inhibited $A\beta_{1-42}$ oligomer toxicity in a dose-dependent manner.

FIGS. 16-20 show the toxicity of $A\beta_{1-42}$ oligomers, formed in the absence or presence of increasing concentrations of the three neutrophil granule proteins and the two CAP37-derived peptides that were found to inhibit fibrillation in FIG. 13. FIG. 16 shows effects of $A\beta_{1-42}$ oligomers on neuron cells in the presence of varying concentrations of NE. NE significantly inhibited $A\beta_{1-42}$ oligomer toxicity in a dose-dependent manner. NE was used at 0.5, 1, 2, and 4-fold the IC50 determined in FIG. 5. Results show a significant inhibition of oligomer toxicity by NE, starting at 2×IC50.

Figure 17:
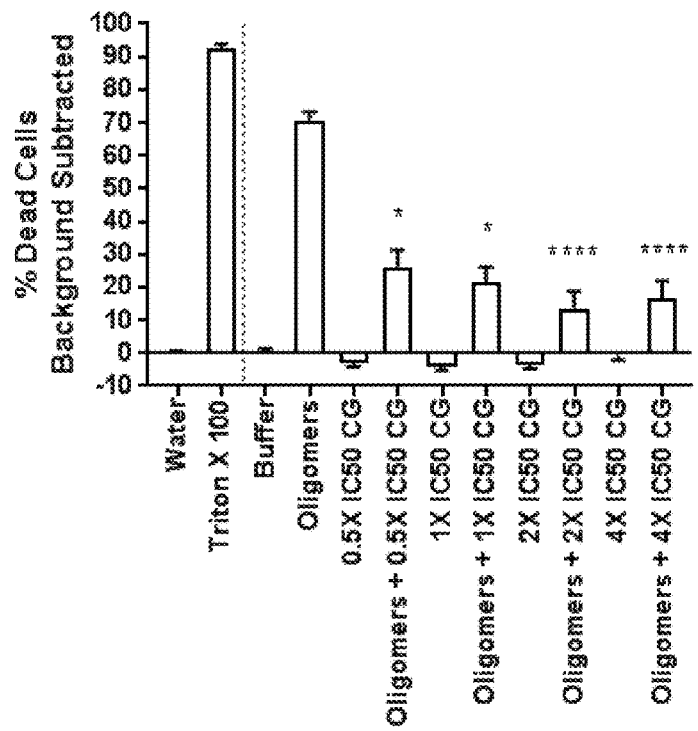
FIG. 17 shows effects of $A\beta_{1-42}$ oligomers on neuron cells in the presence of varying concentrations of CG. CG significantly inhibited $A\beta_{1-42}$ oligomer toxicity in a dose-dependent manner.

FIG. 17 shows effects of $A\beta_{1-42}$ oligomers on neuron cells in the presence of varying concentrations of CG. CG significantly inhibited $A\beta_{1-42}$ oligomer toxicity in a dose-dependent manner. Conditions similar to FIG. 16 were used in FIG. 17, with CG and show a stronger inhibition of oligomer toxicity by CG, starting at 0.5×IC50.

Figure 18:
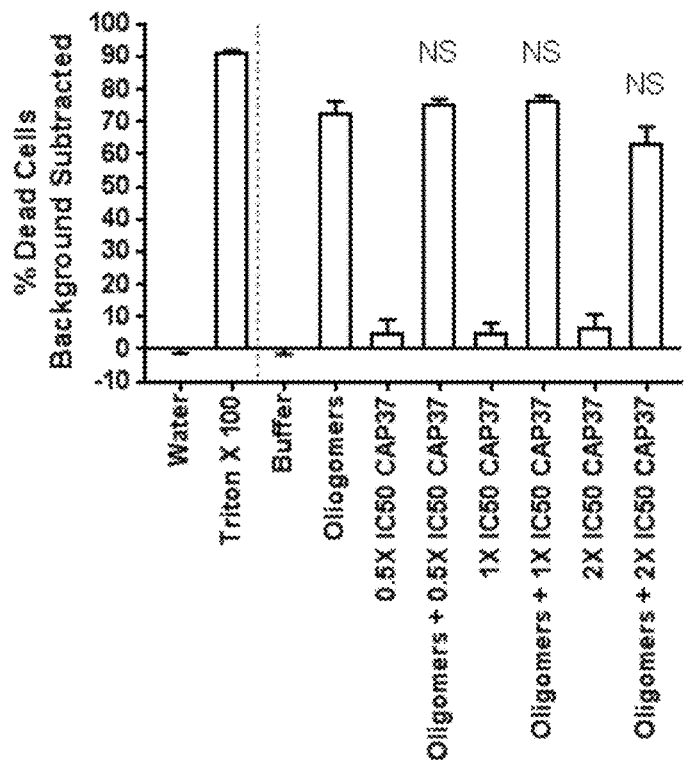
FIG. 18 shows effects of $A\beta_{1-42}$ oligomers on neuron cells in the presence of varying concentrations of CAP37 protein. Full-length CAP37 does not inhibit $A\beta_{1-42}$ oligomer toxicity.

FIG. 18 shows effects of $A\beta_{1-42}$ oligomers on neuron cells in the presence of varying concentrations of CAP37 protein. Under the conditions used, full-length CAP37 does not inhibit $A\beta_{1-42}$ oligomer toxicity. Notably, in these experiments with oligomers, all three neutrophil granule proteins are pre-incubated with $A\beta_{1-42}$ for only 15 min before addition to the cells. The percent cleavage of $A\beta_{1-42}$ during the 15 min oligomerization step is unknown. As discussed above, it is also possible that the larger products generated by CAP37 cleavage are still able to form toxic aggregates under oligomerization conditions.

Figure 19:
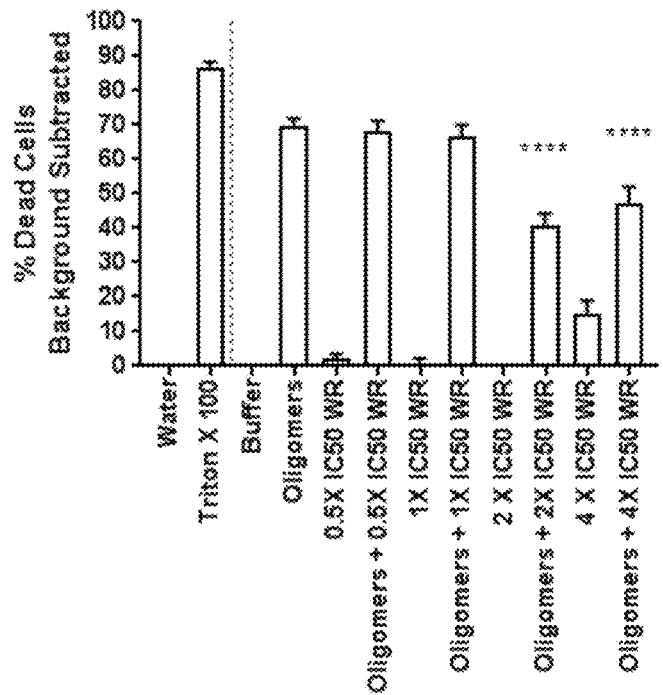
FIG. 19 shows effects of $A\beta_{1-42}$ oligomers on neuron cells in the presence of varying concentrations of CAP37-derived peptide 120-146 WR. The modified CAP37 peptide significantly inhibited $A\beta_{1-42}$ oligomer toxicity in a dose-dependent manner.
Figure 20:
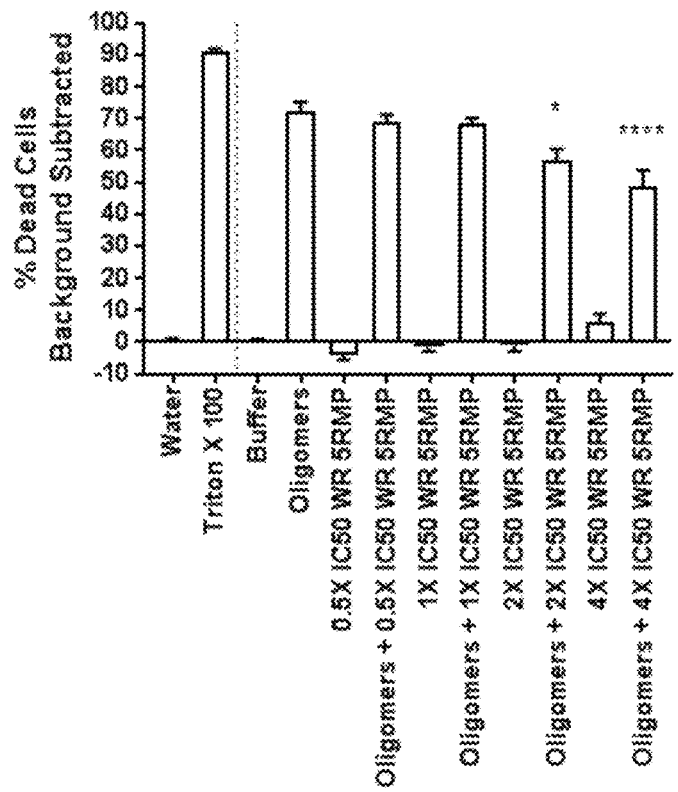
FIG. 20 shows effects of $A\beta_{1-42}$ oligomers on neuron cells in the presence of varying concentrations of CAP37-derived peptide 120-146 WR-5RMP. The 5RMP-modified CAP37 peptide variant significantly inhibited $A\beta_{1-42}$ oligomer toxicity in a dose-dependent manner.

FIG. 19 shows effects of $A\beta_{1-42}$ oligomers on neuron cells in the presence of varying concentrations of CAP37-derived peptide 120-146 WR. The modified CAP37 peptide significantly inhibited $A\beta_{1-42}$ oligomer toxicity in a dose-dependent manner. FIG. 20 shows effects of $A\beta_{1-42}$ oligomers on neuron cells in the presence of varying concentrations of CAP37-derived peptide 120-146 WR-5RMP. The 5RMP-modified CAP37 peptide variant significantly inhibited $A\beta_{1-42}$ oligomer toxicity in a dose-dependent manner. In FIGS. 19 and 20, peptides 120-146 WR and 120-146 WR 5RMP, both interacting with $A\beta_{1-42}$ (FIGS. 2 and 3) and inhibiting fibrillation (FIG. 13), were also able to significantly decrease the toxicity of oligomers. The peptides do not have enzymatic activities on $A\beta_{1-42}$, which suggests that cleavage of $A\beta_{1-42}$ is not the only mechanism for inhibition of $A\beta_{1-42}$ oligomerization and toxicity. Direct binding to $A\beta_{1-42}$ might inhibit oligomerization.

Figure 21:
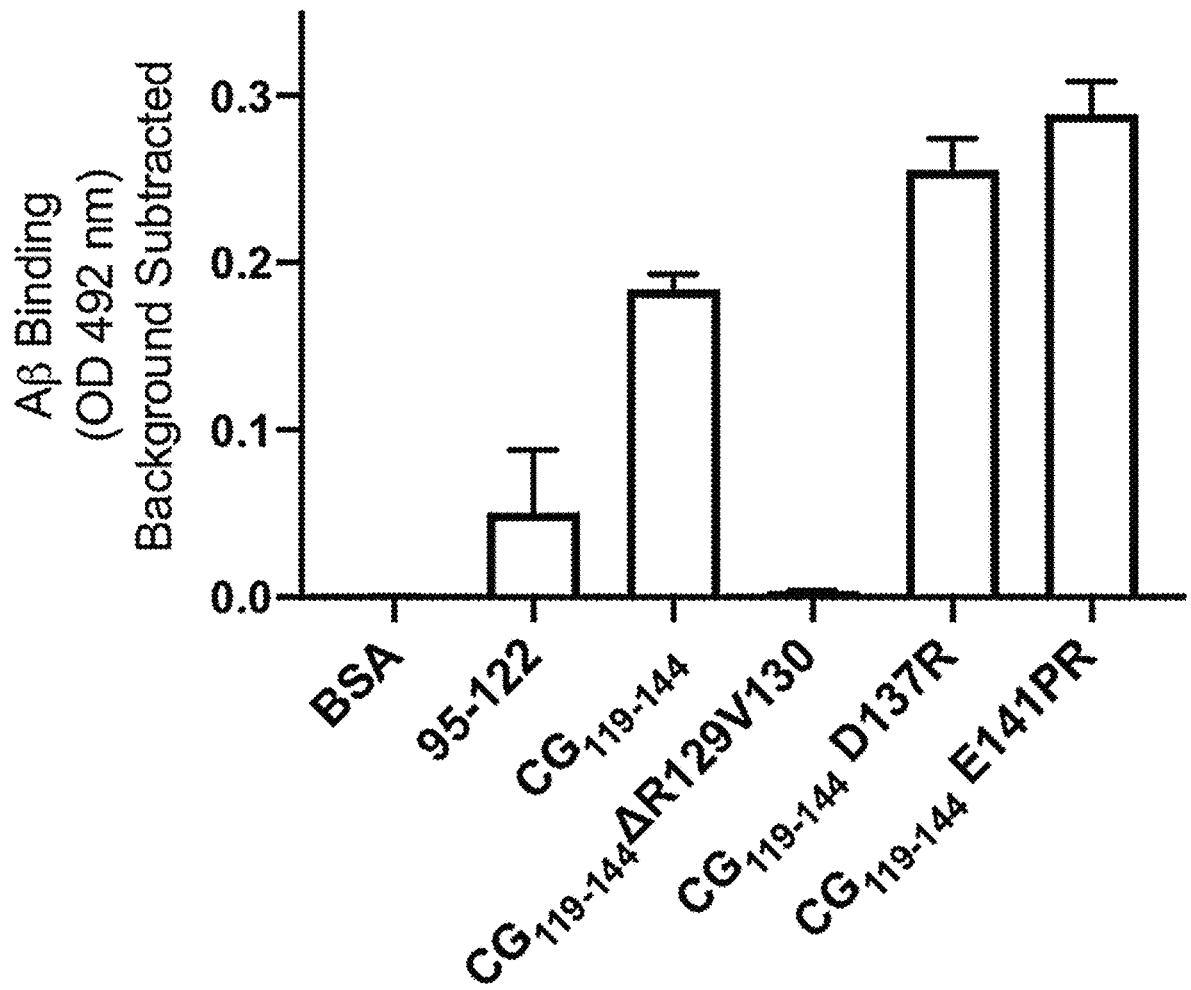
FIG. 21 shows levels of biding of $A\beta_{1-42}$ to wild-type CAP37-derived peptide 95-122 and CG-derived peptide $CG_{119-144}$ and to mutant CG-derived peptides ($CG_{119-144}$ ΔR129V130, $CG_{119-144}$ D137R, and $CG_{119-144}$ E141PR). Highest levels of $A\beta_{1-42}$ bound peptides $CG_{119-144}$, $CG_{119-144}$ D137R, and $CG_{119-144}$ E141PR.

FIG. 21 shows levels of binding of $A\beta_{1-42}$ to wild-type and mutant CG-derived peptides. Replacing each of the two negatively charged residues in $CG_{119-144}$ by positively charged Rs in peptides $CG_{119-144}$ D137R and $CG_{119-144}$ E141PR increased the binding to $A\beta_{1-42}$. Deleting positively charged R129 in peptide $CG_{119-144}$ ΔR129V130 abolished the binding to $A\beta_{1-42}$.

Figure 22:
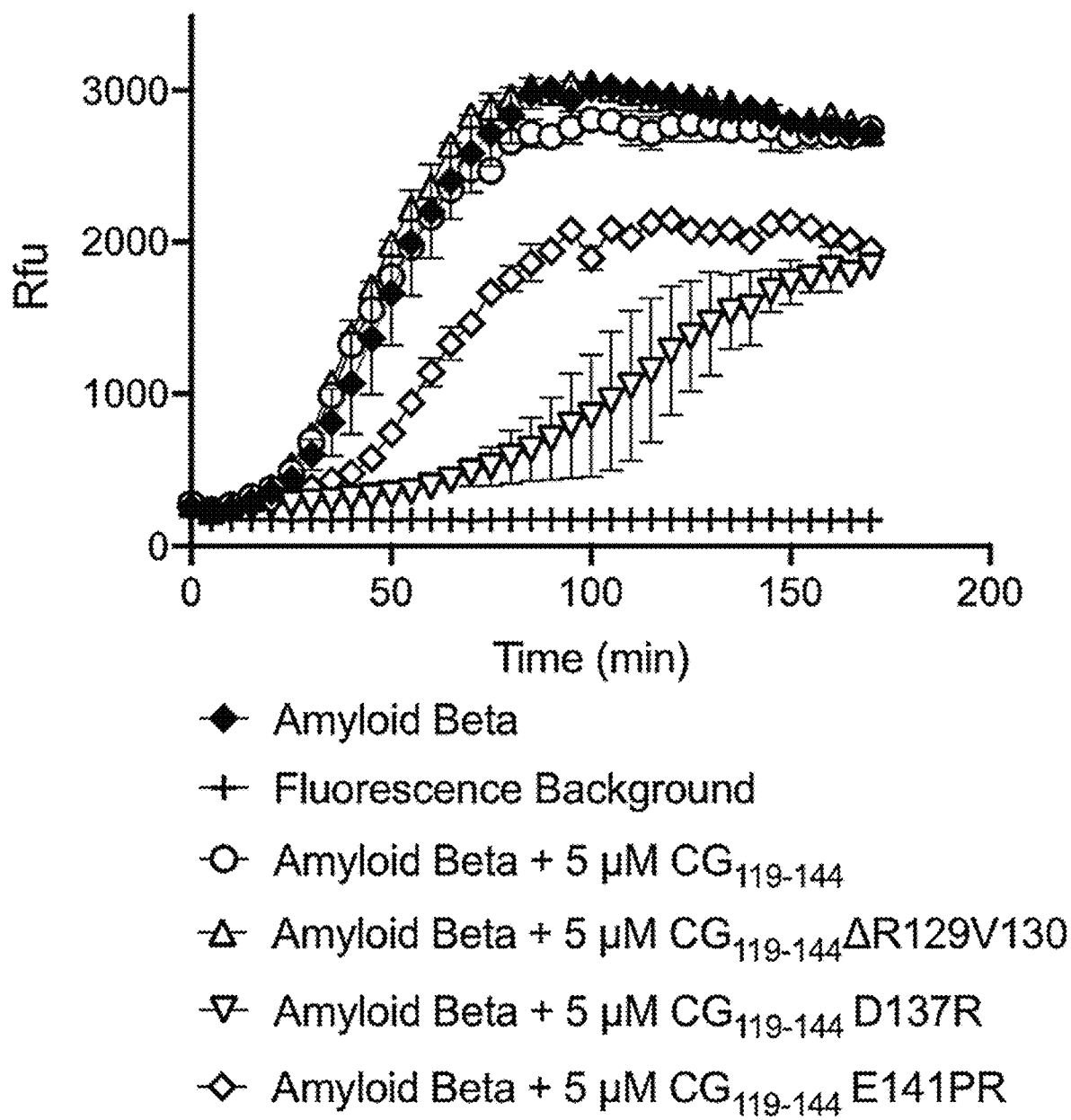
FIG. 22 shows levels of $A\beta_{1-42}$ fibrillation recorded as relative fluorescence unit (Rfu) in the presence of indicated concentrations of wild-type and mutant CG peptides. Mutants $CG_{119-144}$ D137R, and $CG_{119-144}$ E141PR have inhibitory effects on $A\beta_{1-42}$ fibrillation. Wild-type $CG_{119-144}$ and mutant $CG_{119-144}$ ΔR129V130 have no inhibitory effect.
Figure 23:
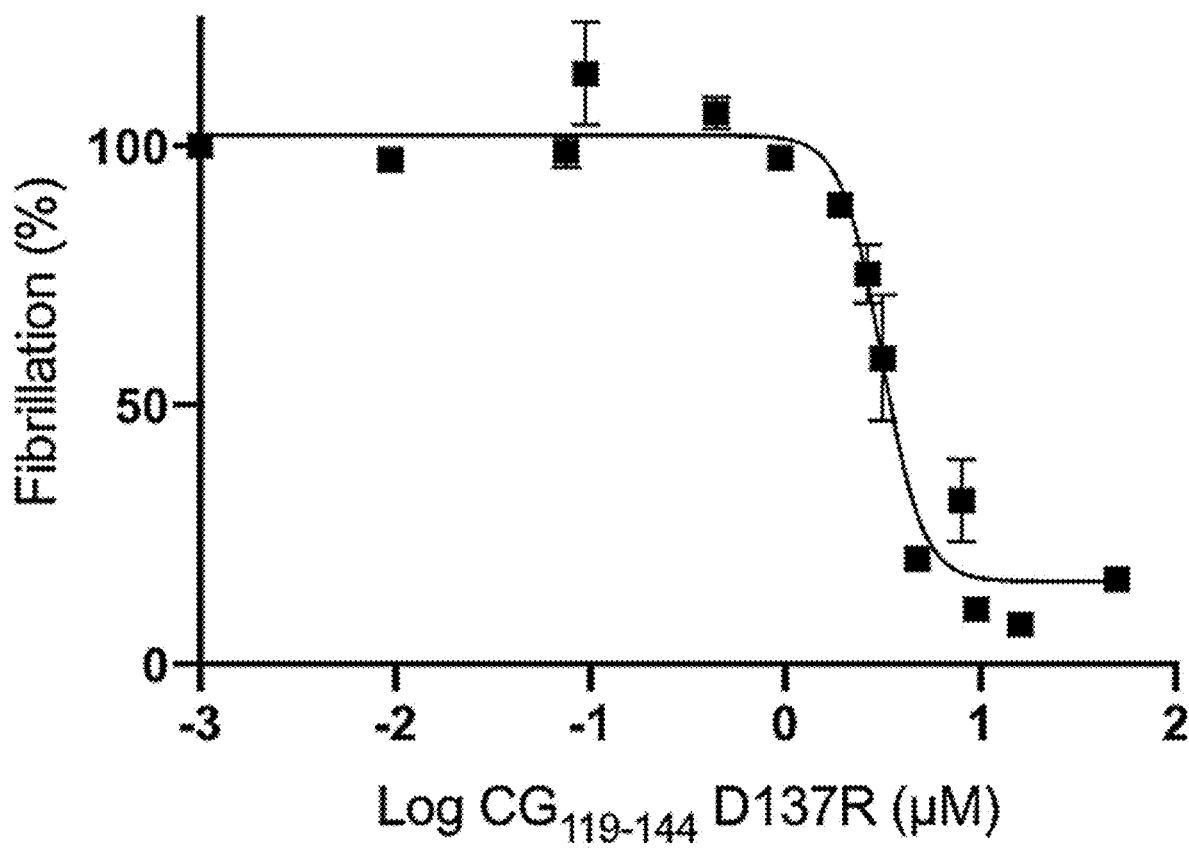
FIG. 23 shows that peptide $CG_{119-144}$ D137R inhibits $A\beta_{1-42}$ fibrillation in a dose-dependent manner.

FIGS. 22 and 23 show fibrillation of $A\beta_{1-42}$ in the absence and presence of increasing concentrations of CG-derived peptides. FIG. 23 shows a dose-dependent inhibition of $A\beta_{1-42}$ fibrillation by mutant $CG_{119-144}$ D137R. The IC50 of $CG_{119-144}$ D137R is 3.1 µM corresponding to a molar ratio for $CG_{119-144}$ D137R/$A\beta_{1-42}$ of 1/3.

Figure 24:
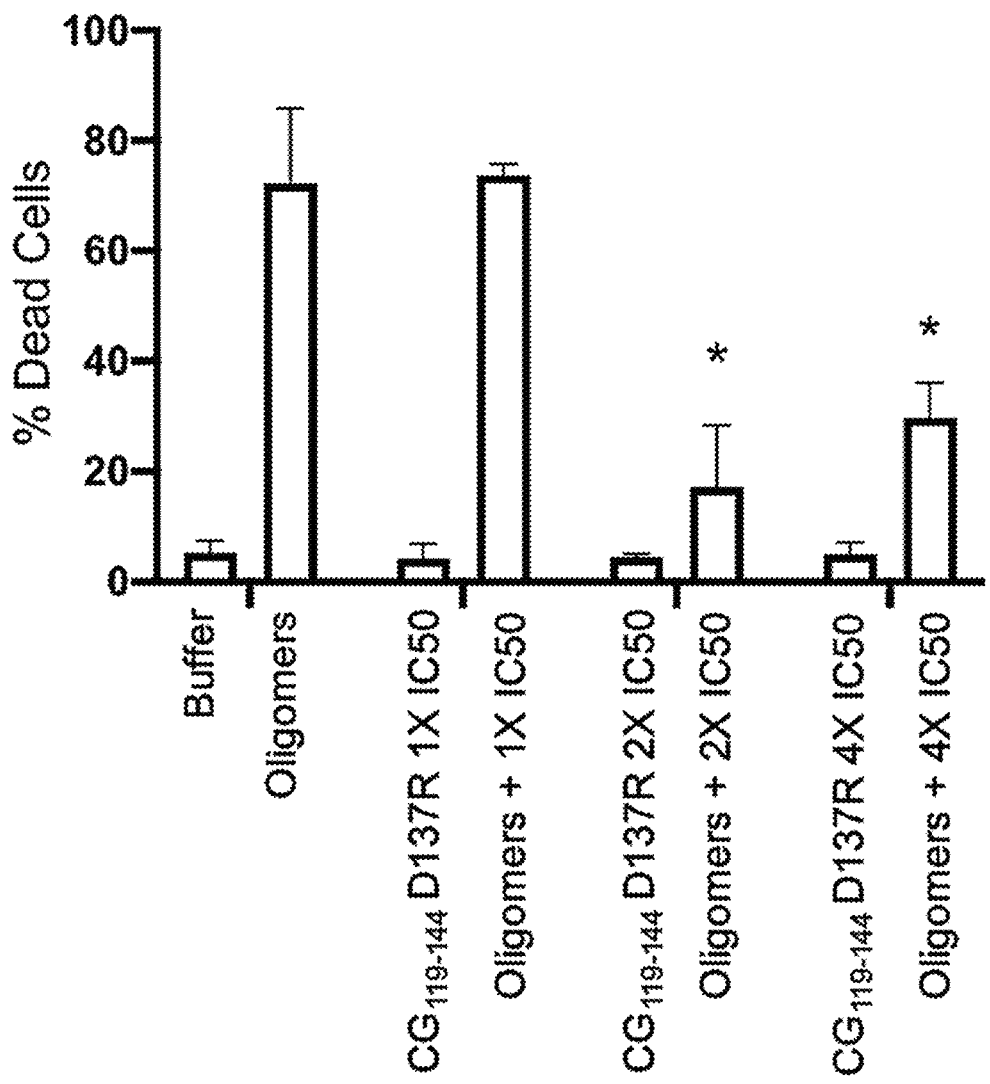
FIG. 24 shows effects of $A\beta_{1-42}$ oligomers on neuron cells in the presence of varying concentrations of CG-derived mutant peptide $CG_{119-144}$ D137R. This mutant CG peptide significantly inhibited $A\beta_{1-42}$ oligomer toxicity in a dose-dependent manner.

FIG. 24 shows the effect of $A\beta_{1-42}$ oligomers on neuron cells in the presence of varying concentrations of peptide $CG_{119-144}$ D137R. This CG-derived mutant, interacting with $A\beta_{1-42}$ (FIG. 21) and inhibiting fibrillation (FIGS. 22 and 23), was also able to significantly decrease the toxicity of oligomers.

Figure 25:
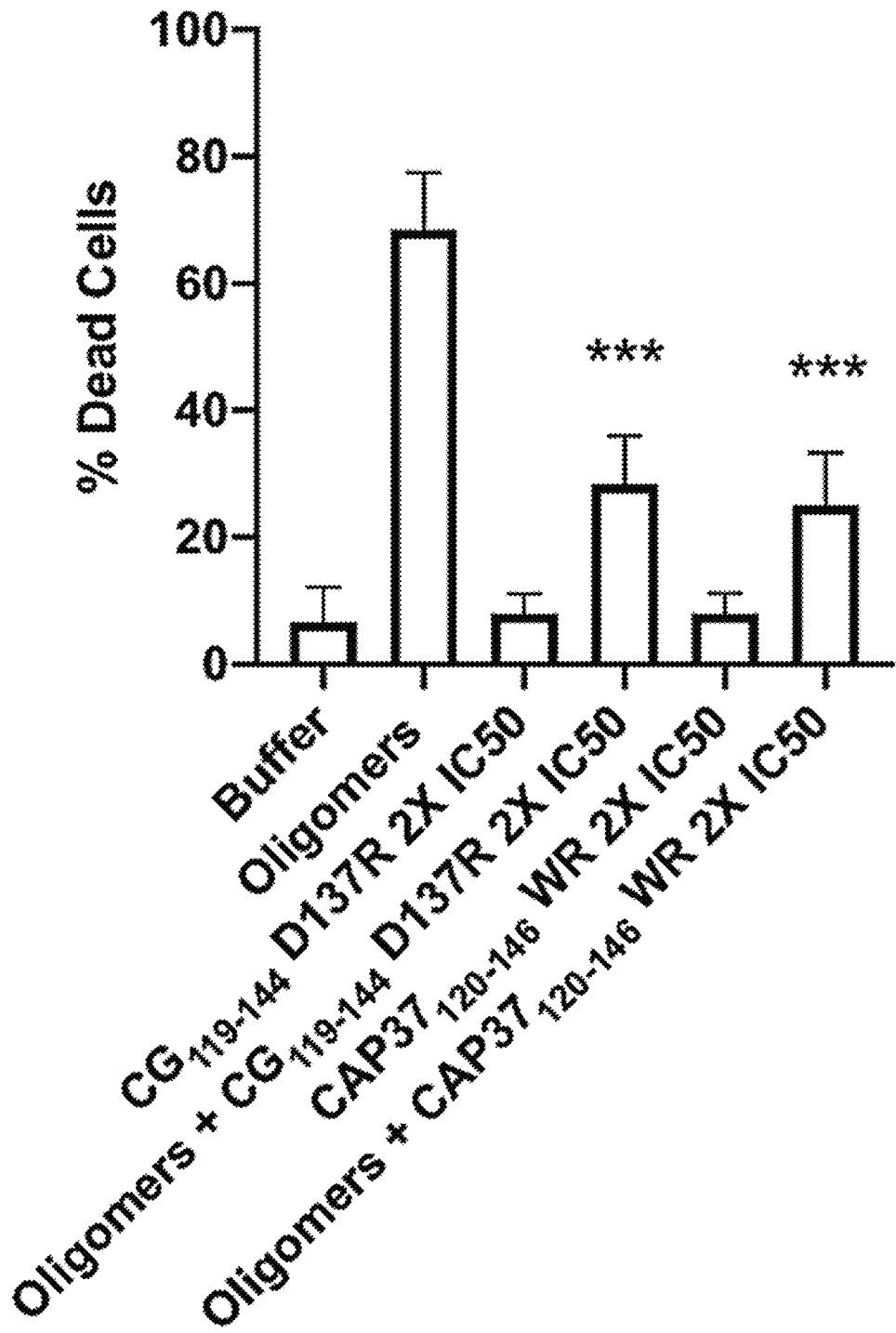
FIG. 25 shows effects of CAP37- and CG-derived peptides preincubation with $A\beta_{1-42}$ oligomers on neurotoxicity. Oligomers are formed first and then incubated in the presence or absence of CG mutant $CG_{119-144}$ D137R or CAP37 mutant 120-146 WR-5RMP for 3 days before treating on neuron cells. Both peptides significantly reversed the neurotoxicity of $A\beta_{1-42}$ oligomers.

Oligomers were formed by incubating 100 µM $A\beta_{1-42}$ in MEMα+N2 Supplements at 4° C. for 3 days. Then, vehicle (water) or peptide at a final concentration of 2×IC50 was added and incubated with oligomers for 3 days at 4° C. Finally, these oligomers were added to neurons at a final concentration of 18 µM, and percent cell death was measured at 24 h. FIG. 25 shows the effects of CG and CAP37 peptides on $A\beta_{1-42}$ oligomers. These peptides, interacting with $A\beta_{1-42}$ (FIGS. 2 and 20) and inhibiting fibrillation (FIGS. 13, 19, 22 and 23), were also able to significantly decrease the toxicity of $A\beta_{1-42}$ oligomers.

While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods and compositions. Changes may be made in the formulation of the various compositions described herein, the methods described herein or in the steps or the sequence of steps of the methods described herein without departing from the spirit and scope of the present disclosure.

What is claimed is:

1. A peptide compound comprising a peptide comprising amino acid sequence SEQ ID NO: 20.

2. The peptide compound of claim 1, wherein the peptide compound inhibits and/or reverses polymerization of amyloid β (Aβ) peptide into Aβ oligomers.

3. The peptide compound of claim 2, wherein the Aβ peptide is at least one of $A\beta_{1-40}$ and $A\beta_{1-42}$.

4. The peptide compound of claim 1, wherein the peptide compound inhibits and/or reverses polymerization of amyloid β (Aβ) peptide into Aβ fibrils.

5. The peptide compound of claim 4, wherein the Aβ peptide is at least one of $A\beta_{1-40}$ and $A\beta_{1-42}$.

6. The peptide compound of claim 1, wherein the peptide compound is effective in causing disaggregation of Aβ plaques.

7. A peptide compound comprising a peptide comprising amino acid sequence SEQ ID NO: 44.

8. The peptide compound of claim 7, wherein the peptide compound inhibits and/or reverses polymerization of amyloid β (Aβ) peptide into Aβ oligomers.

9. The peptide compound of claim 8, wherein the Aβ peptide is at least one of $A\beta_{1-40}$ and $A\beta_{1-42}$.

10. The peptide compound of claim 7, wherein the peptide compound inhibits and/or reverses polymerization of amyloid β (Aβ) peptide into Aβ fibrils.

11. The peptide compound of claim 10, wherein the Aβ peptide is at least one of $A\beta_{1-40}$ and $A\beta_{1-42}$.

12. The peptide compound of claim 7, wherein the peptide compound is effective in causing disaggregation of Aβ plaques.

13. A peptide compound comprising a peptide comprising an amino acid sequence selected from the group consisting of SEQ ID NO: 43 and SEQ ID NO: 15.

14. The peptide compound of claim 13, wherein the peptide compound inhibits and/or reverses polymerization of amyloid β (Aβ) peptide into Aβ oligomers.

15. The peptide compound of claim 14, wherein the AB peptide is at least one of $A\beta_{1-40}$ and $A\beta_{1-42}$.

16. The peptide compound of claim 13, wherein the peptide compound inhibits and/or reverses polymerization of amyloid β (Aβ) peptide into Aβ fibrils.

17. The peptide compound of claim 16, wherein the Aβ peptide is at least one of $A\beta_{1-40}$ and $A\beta_{1-42}$.

18. The peptide compound of claim 17, wherein the peptide compound is effective in causing disaggregation of Aβ plaques.

* * * * *

SEQUENCE LISTING

<160> NUMBER OF SEQ ID NOS: 46

<210> SEQ ID NO 1
<211> LENGTH: 26
<212> TYPE: PRT
<213> ORGANISM: Artificial Sequence
<220> FEATURE:
<223> OTHER INFORMATION: Completely synthesized in the lab. Amino acids 119-144 of Cathepsin G protein.

<400> SEQUENCE: 1

Gly Thr Leu Cys Thr Val Ala Gly Trp Gly Arg Val Ser Met Arg Arg
1               5                   10                  15

Gly Thr Asp Thr Leu Arg Glu Val Gln Leu
            20                  25

<210> SEQ ID NO 2

```
<211> LENGTH: 27
<212> TYPE: PRT
<213> ORGANISM: Artificial Sequence
<220> FEATURE:
<223> OTHER INFORMATION: Completely synthesized in the lab. Amino acids
      119-145 of Neutrophil elastase.

<400> SEQUENCE: 2

Gly Val Gln Cys Leu Ala Met Gly Trp Gly Leu Leu Gly Arg Asn Arg
1               5                   10                  15

Gly Ile Ala Ser Val Leu Gln Glu Leu Asn Val
            20                  25

<210> SEQ ID NO 3
<211> LENGTH: 27
<212> TYPE: PRT
<213> ORGANISM: Artificial Sequence
<220> FEATURE:
<223> OTHER INFORMATION: Completely synthesized in the lab. Amino acids
      120-146 of CAP37 protein.

<400> SEQUENCE: 3

Gly Thr Arg Cys Gln Val Ala Gly Trp Gly Ser Gln Arg Ser Gly Gly
1               5                   10                  15

Arg Leu Ser Arg Phe Pro Arg Phe Val Asn Val
            20                  25

<210> SEQ ID NO 4
<211> LENGTH: 28
<212> TYPE: PRT
<213> ORGANISM: Artificial Sequence
<220> FEATURE:
<223> OTHER INFORMATION: Completely synthesized in the lab. Amino acids
      20-47 of Cathepsin G protein protein.

<400> SEQUENCE: 4

Ile Gln Ser Pro Ala Gly Gln Ser Arg Cys Gly Gly Phe Leu Val Arg
1               5                   10                  15

Glu Asp Phe Val Leu Thr Ala Ala His Cys Trp Gly
            20                  25

<210> SEQ ID NO 5
<211> LENGTH: 25
<212> TYPE: PRT
<213> ORGANISM: Artificial Sequence
<220> FEATURE:
<223> OTHER INFORMATION: Completely synthesized in the lab. Amino acids
      20-44 of Neutrophil elastase.

<400> SEQUENCE: 5

Leu Arg Gly Gly His Phe Cys Gly Ala Thr Leu Ile Ala Pro Asn Phe
1               5                   10                  15

Val Met Ser Ala Ala His Cys Val Ala
            20                  25

<210> SEQ ID NO 6
<211> LENGTH: 25
<212> TYPE: PRT
<213> ORGANISM: Artificial Sequence
<220> FEATURE:
<223> OTHER INFORMATION: Completely synthesized in the lab. Amino acids
      20-44 of CAP37 protein.

<400> SEQUENCE: 6

Asn Gln Gly Arg His Phe Cys Gly Gly Ala Leu Ile His Ala Arg Phe
1               5                   10                  15
```

Val Met Thr Ala Ala Ser Cys Phe Gln
         20                  25

<210> SEQ ID NO 7
<211> LENGTH: 26
<212> TYPE: PRT
<213> ORGANISM: Artificial Sequence
<220> FEATURE:
<223> OTHER INFORMATION: Completely synthesized in the lab. Derivative
      of amino acids 119-144 of Cathepsin G protein.
<220> FEATURE:
<221> NAME/KEY: misc_feature
<222> LOCATION: (2)..(2)
<223> OTHER INFORMATION: Ala, Phe, Gly, Ile, Leu, Met, Pro, Ser, Thr,
      Trp, or Val
<220> FEATURE:
<221> NAME/KEY: misc_feature
<222> LOCATION: (3)..(3)
<223> OTHER INFORMATION: Ala, Phe, Gly, His, Ile, Lys, Leu, Met, Asn,
      Pro, Gln, Arg, Val, or Trp
<220> FEATURE:
<221> NAME/KEY: misc_feature
<222> LOCATION: (4)..(4)
<223> OTHER INFORMATION: Ala, Cys, Ser, Thr, or Val
<220> FEATURE:
<221> NAME/KEY: misc_feature
<222> LOCATION: (5)..(5)
<223> OTHER INFORMATION: Ala, Phe, Gly, Ile, Leu, Met, Pro, Ser, Thr,
      Trp, or Val
<220> FEATURE:
<221> NAME/KEY: misc_feature
<222> LOCATION: (6)..(6)
<223> OTHER INFORMATION: Ala, Phe, Gly, Ile, Leu, Met, Pro, Trp, or Val
<220> FEATURE:
<221> NAME/KEY: misc_feature
<222> LOCATION: (7)..(7)
<223> OTHER INFORMATION: Ala, Phe, Gly, Ile, Leu, Met, Pro, Trp, or Val
<220> FEATURE:
<221> NAME/KEY: misc_feature
<222> LOCATION: (9)..(9)
<223> OTHER INFORMATION: Ala, Phe, Gly, Ile, Leu, Met, Pro, Trp, or Val
<220> FEATURE:
<221> NAME/KEY: misc_feature
<222> LOCATION: (11)..(11)
<223> OTHER INFORMATION: Ala, Cys, Phe, Gly, His, Ile, Lys, Leu, Met,
      Asn, Pro, Gln, Arg, Ser, Thr, Val, Trp, or Tyr
<220> FEATURE:
<221> NAME/KEY: misc_feature
<222> LOCATION: (12)..(12)
<223> OTHER INFORMATION: Ala, Phe, Gly, Ile, Leu, Met, Pro, Trp, or Val
<220> FEATURE:
<221> NAME/KEY: misc_feature
<222> LOCATION: (13)..(13)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (14)..(14)
<223> OTHER INFORMATION: Ala, Phe, Gly, Ile, Leu, Met, Pro, Trp, or Val
<220> FEATURE:
<221> NAME/KEY: misc_feature
<222> LOCATION: (15)..(15)
<223> OTHER INFORMATION: His, Lys, or Arg
<220> FEATURE:
<221> NAME/KEY: misc_feature
<222> LOCATION: (16)..(16)
<223> OTHER INFORMATION: Cys, His, Lys, Asn, Gln, Arg, Ser, Thr, or Tyr
<220> FEATURE:
<221> NAME/KEY: misc_feature
<222> LOCATION: (18)..(18)
<223> OTHER INFORMATION: Cys, Asn, Gln, Ser, Thr, or Tyr
<220> FEATURE:
<221> NAME/KEY: misc_feature
<222> LOCATION: (19)..(19)
<223> OTHER INFORMATION: Arg, Asp, Glu, His, or Lys
<220> FEATURE:
<221> NAME/KEY: misc_feature
<222> LOCATION: (20)..(20)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (21)..(21)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (22)..(22)
<223> OTHER INFORMATION: Ala, Phe, Gly, His, Ile, Lys, Leu, Met, Pro,
      Arg, Trp, or Val
<220> FEATURE:
<221> NAME/KEY: misc_feature
<222> LOCATION: (23)..(23)
<223> OTHER INFORMATION: Leu, Ala, Cys, Asp, Glu, Phe, Gly, His, Ile,
      Lys, Met, Asn, Pro, Gln, Arg, Ser, Thr, Val, Trp, Pro-Arg, or Tyr
<220> FEATURE:
<221> NAME/KEY: misc_feature
<222> LOCATION: (24)..(24)
<223> OTHER INFORMATION: Ala, Phe, Gly, Ile, Leu, Met, Pro, Trp, or Val
<220> FEATURE:
<221> NAME/KEY: misc_feature
<222> LOCATION: (25)..(25)
<223> OTHER INFORMATION: Cys, Asn, Gln, Ser, Thr, or Tyr
<220> FEATURE:
<221> NAME/KEY: misc_feature
<222> LOCATION: (26)..(26)
<223> OTHER INFORMATION: Ala, Phe, Gly, Ile, Leu, Met, Pro, Trp, or Val

<400> SEQUENCE: 7

Gly Xaa Xaa Xaa Xaa Xaa Xaa Gly Xaa Gly Xaa Xaa Xaa Xaa Xaa Xaa
1               5                   10                  15

Gly Xaa Xaa Xaa Xaa Xaa Xaa Xaa Xaa Xaa
            20                  25

<210> SEQ ID NO 8
<211> LENGTH: 27
<212> TYPE: PRT
<213> ORGANISM: Artificial Sequence
<220> FEATURE:
<223> OTHER INFORMATION: Completely synthesized in the lab. Derivative
      of amino acids 119-145 of Neutrophil elastase.
<220> FEATURE:
<221> NAME/KEY: misc_feature
<222> LOCATION: (2)..(2)
<223> OTHER INFORMATION: Ala, Phe, Gly, Ile, Leu, Met, Pro, Ser, Thr,
      Trp, or Val
<220> FEATURE:
<221> NAME/KEY: misc_feature
<222> LOCATION: (3)..(3)
<223> OTHER INFORMATION: Ala, Phe, Gly, His, Ile, Lys, Leu, Met, Asn,
      Pro, Gln, Arg, Val, or Trp
<220> FEATURE:
<221> NAME/KEY: misc_feature
<222> LOCATION: (4)..(4)
<223> OTHER INFORMATION: Ala, Cys, Ser, Thr, or Val
<220> FEATURE:
<221> NAME/KEY: misc_feature
<222> LOCATION: (5)..(5)
<223> OTHER INFORMATION: Ala, Phe, Gly, Ile, Leu, Met, Pro, Ser, Thr,
      Trp, or Val
<220> FEATURE:
<221> NAME/KEY: misc_feature
<222> LOCATION: (6)..(6)
<223> OTHER INFORMATION: Ala, Phe, Gly, Ile, Leu, Met, Pro, Trp, or Val
<220> FEATURE:
<221> NAME/KEY: misc_feature
<222> LOCATION: (7)..(7)
<223> OTHER INFORMATION: Ala, Phe, Gly, Ile, Leu, Met, Pro, Trp, or Val
<220> FEATURE:
<221> NAME/KEY: misc_feature
<222> LOCATION: (9)..(9)
<223> OTHER INFORMATION: Ala, Phe, Gly, Ile, Leu, Met, Pro, Trp, or Val
<220> FEATURE:

```
<221> NAME/KEY: misc_feature
<222> LOCATION: (11)..(11)
<223> OTHER INFORMATION: Ala, Phe, Gly, Ile, Leu, Met, Pro, Trp, or Val
<220> FEATURE:
<221> NAME/KEY: misc_feature
<222> LOCATION: (12)..(12)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (13)..(13)
<223> OTHER INFORMATION: Ala, Phe, Gly, Ile, Leu, Met, Pro, Trp, or Val
<220> FEATURE:
<221> NAME/KEY: misc_feature
<222> LOCATION: (14)..(14)
<223> OTHER INFORMATION: His, Lys, or Arg
<220> FEATURE:
<221> NAME/KEY: misc_feature
<222> LOCATION: (15)..(15)
<223> OTHER INFORMATION: Cys, His, Lys, Asn, Gln, Arg, Ser, Thr, or Tyr
<220> FEATURE:
<221> NAME/KEY: misc_feature
<222> LOCATION: (16)..(16)
<223> OTHER INFORMATION: Ala, Phe, Gly, His, Ile, Lys, Leu, Met, Pro,
      Arg, Trp, or Val
<220> FEATURE:
<221> NAME/KEY: misc_feature
<222> LOCATION: (18)..(18)
<223> OTHER INFORMATION: Asp, Ala, Glu, Phe, Gly, Ile, Leu, Met, Pro,
      Trp, or Val
<220> FEATURE:
<221> NAME/KEY: misc_feature
<222> LOCATION: (19)..(19)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (20)..(20)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (21)..(21)
<223> OTHER INFORMATION: Ala, Phe, Gly, His, Ile, Lys, Leu, Met, Pro,
      Arg, Trp, or Val
<220> FEATURE:
<221> NAME/KEY: misc_feature
<222> LOCATION: (22)..(22)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (23)..(23)
<223> OTHER INFORMATION: Cys, Asn, Gln, Ser, Thr, or Tyr
<220> FEATURE:
<221> NAME/KEY: misc_feature
<222> LOCATION: (24)..(24)
<223> OTHER INFORMATION: Ala, Cys, Asp, Glu, Phe, Gly, His, Ile, Lys,
      Leu, Met, Asn, Pro, Gln, Arg, Ser, Thr, Val, Trp, or Tyr
<220> FEATURE:
<221> NAME/KEY: misc_feature
<222> LOCATION: (25)..(25)
<223> OTHER INFORMATION: Ala, Phe, Gly, Ile, Leu, Met, Pro, Trp, or Val
<220> FEATURE:
<221> NAME/KEY: misc_feature
<222> LOCATION: (26)..(26)
<223> OTHER INFORMATION: Cys, Asn, Gln, Ser, Thr, or Tyr
<220> FEATURE:
<221> NAME/KEY: misc_feature
<222> LOCATION: (27)..(27)
<223> OTHER INFORMATION: Ala, Phe, Gly, Ile, Leu, Met, Pro, Trp, or Val

<400> SEQUENCE: 8

Gly Xaa Xaa Xaa Xaa Xaa Xaa Gly Xaa Gly Xaa Xaa Xaa Xaa Xaa Xaa
1               5                   10                  15

Gly Xaa Xaa Xaa Xaa Xaa Xaa Xaa Xaa Xaa Xaa
            20                  25
```

<210> SEQ ID NO 9
<211> LENGTH: 27
<212> TYPE: PRT
<213> ORGANISM: Artificial Sequence
<220> FEATURE:
<223> OTHER INFORMATION: Completely synthesized in the lab. Derivative
      of amino acids 120-146 of CAP37 protein.
<220> FEATURE:
<221> NAME/KEY: misc_feature
<222> LOCATION: (2)..(2)
<223> OTHER INFORMATION: Ala, Phe, Gly, Ile, Leu, Met, Pro, Ser, Thr,
      Trp, or Val
<220> FEATURE:
<221> NAME/KEY: misc_feature
<222> LOCATION: (3)..(3)
<223> OTHER INFORMATION: Ala, Phe, Gly, His, Ile, Lys, Leu, Met, Asn,
      Pro, Gln, Arg, Val, or Trp
<220> FEATURE:
<221> NAME/KEY: misc_feature
<222> LOCATION: (4)..(4)
<223> OTHER INFORMATION: Ala, Cys, Ser, Thr, or Val
<220> FEATURE:
<221> NAME/KEY: misc_feature
<222> LOCATION: (5)..(5)
<223> OTHER INFORMATION: Ala, Phe, Gly, Ile, Leu, Met, Asn, Pro, Gln,
      Ser, Thr, Trp, or Val
<220> FEATURE:
<221> NAME/KEY: misc_feature
<222> LOCATION: (6)..(6)
<223> OTHER INFORMATION: Ala, Phe, Gly, Ile, Leu, Met, Pro, Trp, or Val
<220> FEATURE:
<221> NAME/KEY: misc_feature
<222> LOCATION: (7)..(7)
<223> OTHER INFORMATION: Ala, Phe, Gly, Ile, Leu, Met, Pro, Trp, or Val
<220> FEATURE:
<221> NAME/KEY: misc_feature
<222> LOCATION: (9)..(9)
<223> OTHER INFORMATION: Ala, Phe, Gly, Ile, Leu, Met, Pro, Trp, or Val
<220> FEATURE:
<221> NAME/KEY: misc_feature
<222> LOCATION: (11)..(11)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (12)..(12)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (13)..(13)
<223> OTHER INFORMATION: Cys, His, Lys, Asn, Gln, Arg, Ser, Thr, or Tyr
<220> FEATURE:
<221> NAME/KEY: misc_feature
<222> LOCATION: (14)..(14)
<223> OTHER INFORMATION: Cys, His, Lys, Asn, Gln, Arg, Ser, Thr, or Tyr
<220> FEATURE:
<221> NAME/KEY: misc_feature
<222> LOCATION: (16)..(16)
<223> OTHER INFORMATION: Ala, Phe, Gly, Ile, Leu, Met, Pro, Ser, Thr,
      Trp, or Val
<220> FEATURE:
<221> NAME/KEY: misc_feature
<222> LOCATION: (17)..(17)
<223> OTHER INFORMATION: Asp, Ala, Glu, Phe, Gly, Ile, Lys, Leu, Met,
      Pro, Arg, Ser, Thr, Val, Trp, or Tyr
<220> FEATURE:
<221> NAME/KEY: misc_feature
<222> LOCATION: (18)..(18)
<223> OTHER INFORMATION: Ala, Cys, Phe, Gly, Ile, Leu, Met, Asn, Pro,
      Gln, Ser, Thr, Val, Trp, or Tyr
<220> FEATURE:
<221> NAME/KEY: misc_feature
<222> LOCATION: (19)..(19)
<223> OTHER INFORMATION: Ala, Cys, Phe, Gly, Ile, Leu, Met, Asn, Pro,
      Gln, Ser, Thr, Val, Trp, or Tyr
<220> FEATURE:

```
<221> NAME/KEY: misc_feature
<222> LOCATION: (20)..(20)
<223> OTHER INFORMATION: Ala, Phe, Gly, His, Ile, Lys, Leu, Met, Pro,
      Arg, Thr, or Val
<220> FEATURE:
<221> NAME/KEY: misc_feature
<222> LOCATION: (21)..(21)
<223> OTHER INFORMATION: Ala, Phe, Gly, Ile, Leu, Met, Pro, Val, Trp, or
      Tyr
<220> FEATURE:
<221> NAME/KEY: misc_feature
<222> LOCATION: (22)..(22)
<223> OTHER INFORMATION: Ala, Cys, Asp, Glu, Phe, Gly, His, Ile, Lys,
      Leu, Met, Asn, Pro, Gln, Arg, Ser, Thr, Val, Trp, or Tyr
<220> FEATURE:
<221> NAME/KEY: misc_feature
<222> LOCATION: (23)..(23)
<223> OTHER INFORMATION: Ala, Cys, Asp, Glu, Phe, Gly, His, Ile, Lys,
      Leu, Met, Asn, Pro, Gln, Arg, Ser, Thr, Val, Trp, or Tyr
<220> FEATURE:
<221> NAME/KEY: misc_feature
<222> LOCATION: (24)..(24)
<223> OTHER INFORMATION: Ala, Phe, Gly, Ile, Leu, Met, Pro, Trp, or Val
<220> FEATURE:
<221> NAME/KEY: misc_feature
<222> LOCATION: (25)..(25)
<223> OTHER INFORMATION: Ala, Phe, Gly, Ile, Leu, Met, Pro, Trp, or Val
<220> FEATURE:
<221> NAME/KEY: misc_feature
<222> LOCATION: (26)..(26)
<223> OTHER INFORMATION: Cys, Asn, Gln, Ser, Thr, or Tyr
<220> FEATURE:
<221> NAME/KEY: misc_feature
<222> LOCATION: (27)..(27)
<223> OTHER INFORMATION: Ala, Phe, Gly, Ile, Leu, Met, Pro, Trp, or Val

<400> SEQUENCE: 9

Gly Xaa Xaa Xaa Xaa Xaa Xaa Gly Xaa Gly Xaa Xaa Xaa Xaa Gly Xaa
1               5                   10                  15

Xaa Xaa Xaa Xaa Xaa Xaa Xaa Xaa Xaa Xaa Xaa
            20                  25

<210> SEQ ID NO 10
<211> LENGTH: 28
<212> TYPE: PRT
<213> ORGANISM: Artificial Sequence
<220> FEATURE:
<223> OTHER INFORMATION: Completely synthesized in the lab. Derivative
      of amino acids 20-47 of Cathepsin G protein protein.
<220> FEATURE:
<221> NAME/KEY: misc_feature
<222> LOCATION: (1)..(1)
<223> OTHER INFORMATION: Phe, Tyr, Trp, Ala, Val, Ile, Leu, or Met
<220> FEATURE:
<221> NAME/KEY: misc_feature
<222> LOCATION: (2)..(2)
<223> OTHER INFORMATION: Asn, Ser, Thr, or Gln
<220> FEATURE:
<221> NAME/KEY: misc_feature
<222> LOCATION: (3)..(3)
<223> OTHER INFORMATION: Asn, Ser, Thr, or Gln
<220> FEATURE:
<221> NAME/KEY: misc_feature
<222> LOCATION: (4)..(4)
<223> OTHER INFORMATION: Pro, Phe, Tyr, Trp, Ala, Val, Ile, Leu, Met, or
      Gly
<220> FEATURE:
<221> NAME/KEY: misc_feature
<222> LOCATION: (5)..(5)
<223> OTHER INFORMATION: Phe, Tyr, Trp, Ala, Val, Ile, Leu, or Met
<220> FEATURE:
<221> NAME/KEY: misc_feature
<222> LOCATION: (6)..(6)
<223> OTHER INFORMATION: Gly, Ala, or Val
<220> FEATURE:
<221> NAME/KEY: misc_feature
```

```
<222> LOCATION: (7)..(7)
<223> OTHER INFORMATION: Asn, Ser, Thr, or Gln
<220> FEATURE:
<221> NAME/KEY: misc_feature
<222> LOCATION: (8)..(8)
<223> OTHER INFORMATION: Asn, Ser, Thr, or Gln
<220> FEATURE:
<221> NAME/KEY: misc_feature
<222> LOCATION: (9)..(9)
<223> OTHER INFORMATION: Arg, His, or Lys
<220> FEATURE:
<221> NAME/KEY: misc_feature
<222> LOCATION: (10)..(10)
<223> OTHER INFORMATION: Cys, Ser, or Thr
<220> FEATURE:
<221> NAME/KEY: misc_feature
<222> LOCATION: (11)..(11)
<223> OTHER INFORMATION: Gly, Ala, or Val
<220> FEATURE:
<221> NAME/KEY: misc_feature
<222> LOCATION: (12)..(12)
<223> OTHER INFORMATION: Gly, Ala, or Val
<220> FEATURE:
<221> NAME/KEY: misc_feature
<222> LOCATION: (13)..(13)
<223> OTHER INFORMATION: Phe, Tyr, Trp, Ala, Val, Ile, Leu, or Met
<220> FEATURE:
<221> NAME/KEY: misc_feature
<222> LOCATION: (14)..(14)
<223> OTHER INFORMATION: Phe, Tyr, Trp, Ala, Val, Ile, Leu, or Met
<220> FEATURE:
<221> NAME/KEY: misc_feature
<222> LOCATION: (15)..(15)
<223> OTHER INFORMATION: Phe, Tyr, Trp, Ala, Val, Ile, Leu, or Met
<220> FEATURE:
<221> NAME/KEY: misc_feature
<222> LOCATION: (16)..(16)
<223> OTHER INFORMATION: Arg, His, or Lys
<220> FEATURE:
<221> NAME/KEY: misc_feature
<222> LOCATION: (17)..(17)
<223> OTHER INFORMATION: Glu or Asp
<220> FEATURE:
<221> NAME/KEY: misc_feature
<222> LOCATION: (18)..(18)
<223> OTHER INFORMATION: Glu or Asp
<220> FEATURE:
<221> NAME/KEY: misc_feature
<222> LOCATION: (19)..(19)
<223> OTHER INFORMATION: Phe, Tyr, Trp, Ala, Val, Ile, Leu, or Met
<220> FEATURE:
<221> NAME/KEY: misc_feature
<222> LOCATION: (20)..(20)
<223> OTHER INFORMATION: Phe, Tyr, Trp, Ala, Val, Ile, Leu, or Met
<220> FEATURE:
<221> NAME/KEY: misc_feature
<222> LOCATION: (21)..(21)
<223> OTHER INFORMATION: Phe, Tyr, Trp, Ala, Val, Ile, Leu, or Met
<220> FEATURE:
<221> NAME/KEY: misc_feature
<222> LOCATION: (22)..(22)
<223> OTHER INFORMATION: Asn, Ser, Thr, or Gln
<220> FEATURE:
<221> NAME/KEY: misc_feature
<222> LOCATION: (23)..(23)
<223> OTHER INFORMATION: Phe, Tyr, Trp, Ala, Val, Ile, Leu, or Met
<220> FEATURE:
<221> NAME/KEY: misc_feature
<222> LOCATION: (24)..(24)
<223> OTHER INFORMATION: Phe, Tyr, Trp, Ala, Val, Ile, Leu, or Met
<220> FEATURE:
<221> NAME/KEY: misc_feature
<222> LOCATION: (25)..(25)
<223> OTHER INFORMATION: Arg, His, or Lys
<220> FEATURE:
<221> NAME/KEY: misc_feature
<222> LOCATION: (26)..(26)
<223> OTHER INFORMATION: Cys, Ser, or Thr
<220> FEATURE:
```

```
<221> NAME/KEY: misc_feature
<222> LOCATION: (27)..(27)
<223> OTHER INFORMATION: Phe, Tyr, Trp, Ala, Val, Ile, Leu, or Met
<220> FEATURE:
<221> NAME/KEY: misc_feature
<222> LOCATION: (28)..(28)
<223> OTHER INFORMATION: Gly, Ala, or Val

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 11
<211> LENGTH: 25
<212> TYPE: PRT
<213> ORGANISM: Artificial Sequence
<220> FEATURE:
<223> OTHER INFORMATION: Completely synthesized in the lab. Derivative
      of amino acids 20-44 of Neutrophil elastase.
<220> FEATURE:
<221> NAME/KEY: misc_feature
<222> LOCATION: (1)..(1)
<223> OTHER INFORMATION: Phe, Tyr, Trp, Ala, Val, Ile, Leu, or Met
<220> FEATURE:
<221> NAME/KEY: misc_feature
<222> LOCATION: (2)..(2)
<223> OTHER INFORMATION: Arg, His, or Lys
<220> FEATURE:
<221> NAME/KEY: misc_feature
<222> LOCATION: (3)..(3)
<223> OTHER INFORMATION: Gly, Ala, or Val
<220> FEATURE:
<221> NAME/KEY: misc_feature
<222> LOCATION: (4)..(4)
<223> OTHER INFORMATION: Gly, Ala, or Val
<220> FEATURE:
<221> NAME/KEY: misc_feature
<222> LOCATION: (5)..(5)
<223> OTHER INFORMATION: Arg, His, or Lys
<220> FEATURE:
<221> NAME/KEY: misc_feature
<222> LOCATION: (6)..(6)
<223> OTHER INFORMATION: Phe, Tyr, Trp, Ala, val, Ile, Leu, or Met
<220> FEATURE:
<221> NAME/KEY: misc_feature
<222> LOCATION: (7)..(7)
<223> OTHER INFORMATION: Cys, Ser, or Thr
<220> FEATURE:
<221> NAME/KEY: misc_feature
<222> LOCATION: (8)..(8)
<223> OTHER INFORMATION: Gly, Ala, or Val
<220> FEATURE:
<221> NAME/KEY: misc_feature
<222> LOCATION: (9)..(9)
<223> OTHER INFORMATION: Phe, Tyr, Trp, Ala, Val, Ile, Leu, or Met
<220> FEATURE:
<221> NAME/KEY: misc_feature
<222> LOCATION: (10)..(10)
<223> OTHER INFORMATION: Asn, Ser, Thr, or Gln
<220> FEATURE:
<221> NAME/KEY: misc_feature
<222> LOCATION: (11)..(11)
<223> OTHER INFORMATION: Phe, Tyr, Trp, Ala, Val, Ile, Leu, or Met
<220> FEATURE:
<221> NAME/KEY: misc_feature
<222> LOCATION: (12)..(12)
<223> OTHER INFORMATION: Phe, Tyr, Trp, Ala, Val, Ile, Leu, or Met
<220> FEATURE:
<221> NAME/KEY: misc_feature
<222> LOCATION: (13)..(13)
<223> OTHER INFORMATION: Phe, Tyr, Trp, Ala, Val, Ile, Leu, or Met
<220> FEATURE:
<221> NAME/KEY: misc_feature
<222> LOCATION: (14)..(14)
```

```
<223> OTHER INFORMATION: Pro, Phe, Tyr, Trp, Ala, Val, Ile, Leu, Met, or
      Gly
<220> FEATURE:
<221> NAME/KEY: misc_feature
<222> LOCATION: (15)..(15)
<223> OTHER INFORMATION: Asn, Ser, Thr, or Gln
<220> FEATURE:
<221> NAME/KEY: misc_feature
<222> LOCATION: (16)..(16)
<223> OTHER INFORMATION: Phe, Tyr, Trp, Ala, Val, Ile, Leu, or Met
<220> FEATURE:
<221> NAME/KEY: misc_feature
<222> LOCATION: (17)..(17)
<223> OTHER INFORMATION: Phe, Tyr, Trp, Ala, Val, Ile, Leu, or Met
<220> FEATURE:
<221> NAME/KEY: misc_feature
<222> LOCATION: (18)..(18)
<223> OTHER INFORMATION: Phe, Tyr, Trp, Ala, Val, Ile, Leu, or Met
<220> FEATURE:
<221> NAME/KEY: misc_feature
<222> LOCATION: (19)..(19)
<223> OTHER INFORMATION: Asn, Ser, Thr, or Gln
<220> FEATURE:
<221> NAME/KEY: misc_feature
<222> LOCATION: (20)..(20)
<223> OTHER INFORMATION: Phe, Tyr, Trp, Ala, Val, Ile, Leu, or Met
<220> FEATURE:
<221> NAME/KEY: misc_feature
<222> LOCATION: (21)..(21)
<223> OTHER INFORMATION: Phe, Tyr, Trp, Ala, Val, Ile, Leu, or Met
<220> FEATURE:
<221> NAME/KEY: misc_feature
<222> LOCATION: (22)..(22)
<223> OTHER INFORMATION: Arg, His, or Lys
<220> FEATURE:
<221> NAME/KEY: misc_feature
<222> LOCATION: (23)..(23)
<223> OTHER INFORMATION: Cys, Ser, or Thr
<220> FEATURE:
<221> NAME/KEY: misc_feature
<222> LOCATION: (24)..(24)
<223> OTHER INFORMATION: Phe, Tyr, Trp, Ala, Val, Ile, Leu, or Met
<220> FEATURE:
<221> NAME/KEY: misc_feature
<222> LOCATION: (25)..(25)
<223> OTHER INFORMATION: Phe, Tyr, Trp, Ala, Val, Ile, Leu, or Met

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 12
<211> LENGTH: 25
<212> TYPE: PRT
<213> ORGANISM: Artificial Sequence
<220> FEATURE:
<223> OTHER INFORMATION: Completely synthesized in the lab. Derivative
      of amino acids 20-44 of CAP37 protein.
<220> FEATURE:
<221> NAME/KEY: misc_feature
<222> LOCATION: (1)..(1)
<223> OTHER INFORMATION: Asn, Ser, Thr, or Gln
<220> FEATURE:
<221> NAME/KEY: misc_feature
<222> LOCATION: (2)..(2)
<223> OTHER INFORMATION: Asn, Ser, Thr, or Gln
<220> FEATURE:
<221> NAME/KEY: misc_feature
<222> LOCATION: (3)..(3)
<223> OTHER INFORMATION: Gly, Ala, or Val
<220> FEATURE:
<221> NAME/KEY: misc_feature
<222> LOCATION: (4)..(4)
<223> OTHER INFORMATION: Arg, His, or Lys
```

```
<220> FEATURE:
<221> NAME/KEY: misc_feature
<222> LOCATION: (5)..(5)
<223> OTHER INFORMATION: Arg, His, or Lys
<220> FEATURE:
<221> NAME/KEY: misc_feature
<222> LOCATION: (6)..(6)
<223> OTHER INFORMATION: Phe, Tyr, Trp, Ala, val, Ile, Leu, or Met
<220> FEATURE:
<221> NAME/KEY: misc_feature
<222> LOCATION: (7)..(7)
<223> OTHER INFORMATION: Cys, Ser, or Thr
<220> FEATURE:
<221> NAME/KEY: misc_feature
<222> LOCATION: (8)..(8)
<223> OTHER INFORMATION: Gly, Ala, or Val
<220> FEATURE:
<221> NAME/KEY: misc_feature
<222> LOCATION: (9)..(9)
<223> OTHER INFORMATION: Gly, Ala, or Val
<220> FEATURE:
<221> NAME/KEY: misc_feature
<222> LOCATION: (10)..(10)
<223> OTHER INFORMATION: Phe, Tyr, Trp, Ala, Val, Ile, Leu, or Met
<220> FEATURE:
<221> NAME/KEY: misc_feature
<222> LOCATION: (11)..(11)
<223> OTHER INFORMATION: Phe, Tyr, Trp, Ala, Val, Ile, Leu, or Met
<220> FEATURE:
<221> NAME/KEY: misc_feature
<222> LOCATION: (12)..(12)
<223> OTHER INFORMATION: Phe, Tyr, Trp, Ala, Val, Ile, Leu, or Met
<220> FEATURE:
<221> NAME/KEY: misc_feature
<222> LOCATION: (13)..(13)
<223> OTHER INFORMATION: Arg, His, or Lys
<220> FEATURE:
<221> NAME/KEY: misc_feature
<222> LOCATION: (14)..(14)
<223> OTHER INFORMATION: Phe, Tyr, Trp, Ala, Val, Ile, Leu, or Met
<220> FEATURE:
<221> NAME/KEY: misc_feature
<222> LOCATION: (15)..(15)
<223> OTHER INFORMATION: Arg, His, or Lys
<220> FEATURE:
<221> NAME/KEY: misc_feature
<222> LOCATION: (16)..(16)
<223> OTHER INFORMATION: Phe, Tyr, Trp, Ala, Val, Ile, Leu, or Met
<220> FEATURE:
<221> NAME/KEY: misc_feature
<222> LOCATION: (17)..(17)
<223> OTHER INFORMATION: Phe, Tyr, Trp, Ala, Val, Ile, Leu, or Met
<220> FEATURE:
<221> NAME/KEY: misc_feature
<222> LOCATION: (18)..(18)
<223> OTHER INFORMATION: Phe, Tyr, Trp, Ala, Val, Ile, Leu, or Met
<220> FEATURE:
<221> NAME/KEY: misc_feature
<222> LOCATION: (19)..(19)
<223> OTHER INFORMATION: Asn, Ser, Thr, or Gln
<220> FEATURE:
<221> NAME/KEY: misc_feature
<222> LOCATION: (20)..(20)
<223> OTHER INFORMATION: Phe, Tyr, Trp, Ala, Val, Ile, Leu, or Met
<220> FEATURE:
<221> NAME/KEY: misc_feature
<222> LOCATION: (21)..(21)
<223> OTHER INFORMATION: Phe, Tyr, Trp, Ala, Val, Ile, Leu, or Met
<220> FEATURE:
<221> NAME/KEY: misc_feature
<222> LOCATION: (22)..(22)
<223> OTHER INFORMATION: Asn, Ser, Thr, or Gln
<220> FEATURE:
<221> NAME/KEY: misc_feature
<222> LOCATION: (23)..(23)
<223> OTHER INFORMATION: Cys, Ser, or Thr
<220> FEATURE:
<221> NAME/KEY: misc_feature
<222> LOCATION: (24)..(24)
```

```
<223> OTHER INFORMATION: Phe, Tyr, Trp, Ala, Val, Ile, Leu, or Met
<220> FEATURE:
<221> NAME/KEY: misc_feature
<222> LOCATION: (25)..(25)
<223> OTHER INFORMATION: Asn, Ser, Thr, or Gln

<400> SEQUENCE: 12

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 13
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 C122S.

<400> SEQUENCE: 13

Gly Thr Leu Ser Thr Val Ala Gly Trp Gly Arg Val Ser Met Arg Arg
1               5                   10                  15

Gly Thr Asp Thr Leu Arg Glu Val Gln Leu
            20                  25

<210> SEQ ID NO 14
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 C122A.

<400> SEQUENCE: 14

Gly Thr Leu Ala Thr Val Ala Gly Trp Gly Arg Val Ser Met Arg Arg
1               5                   10                  15

Gly Thr Asp Thr Leu Arg Glu Val Gln Leu
            20                  25

<210> SEQ ID NO 15
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 D137R.

<400> SEQUENCE: 15

Gly Thr Leu Cys Thr Val Ala Gly Trp Gly Arg Val Ser Met Arg Arg
1               5                   10                  15

Gly Thr Arg Thr Leu Arg Glu Val Gln Leu
            20                  25

<210> SEQ ID NO 16
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 R140M.

<400> SEQUENCE: 16

Gly Thr Leu Cys Thr Val Ala Gly Trp Gly Arg Val Ser Met Arg Arg
1               5                   10                  15
```

Gly Thr Asp Thr Leu Met Glu Val Gln Leu
            20                  25

<210> SEQ ID NO 17
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 E141R.

<400> SEQUENCE: 17

Gly Thr Leu Cys Thr Val Ala Gly Trp Gly Arg Val Ser Met Arg Arg
1               5                   10                  15

Gly Thr Asp Thr Leu Arg Arg Val Gln Leu
            20                  25

<210> SEQ ID NO 18
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 E141M.

<400> SEQUENCE: 18

Gly Thr Leu Cys Thr Val Ala Gly Trp Gly Arg Val Ser Met Arg Arg
1               5                   10                  15

Gly Thr Asp Thr Leu Arg Met Val Gln Leu
            20                  25

<210> SEQ ID NO 19
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 E141L.

<400> SEQUENCE: 19

Gly Thr Leu Cys Thr Val Ala Gly Trp Gly Arg Val Ser Met Arg Arg
1               5                   10                  15

Gly Thr Asp Thr Leu Arg Leu Val Gln Leu
            20                  25

<210> SEQ ID NO 20
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 D137R, E141R.

<400> SEQUENCE: 20

Gly Thr Leu Cys Thr Val Ala Gly Trp Gly Arg Val Ser Met Arg Arg
1               5                   10                  15

Gly Thr Arg Thr Leu Arg Arg Val Gln Leu
            20                  25

<210> SEQ ID NO 21
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 R140M,E141R.

```
<400> SEQUENCE: 21

Gly Thr Leu Cys Thr Val Ala Gly Trp Gly Arg Val Ser Met Arg Arg
1               5                   10                  15

Gly Thr Asp Thr Leu Met Arg Val Gln Leu
            20                  25

<210> SEQ ID NO 22
<211> LENGTH: 26
<212> TYPE: PRT
<213> ORGANISM: Artificial Sequence
<220> FEATURE:
<223> OTHER INFORMATION: Completely synthesized in the lab. Peptide
      CG119-144 R140M,E141M.

<400> SEQUENCE: 22

Gly Thr Leu Cys Thr Val Ala Gly Trp Gly Arg Val Ser Met Arg Arg
1               5                   10                  15

Gly Thr Asp Thr Leu Met Met Val Gln Leu
            20                  25

<210> SEQ ID NO 23
<211> LENGTH: 24
<212> TYPE: PRT
<213> ORGANISM: Artificial Sequence
<220> FEATURE:
<223> OTHER INFORMATION: Completely synthesized in the lab. Peptide
      CG119-144, G135 and T136.

<400> SEQUENCE: 23

Gly Thr Leu Cys Thr Val Ala Gly Trp Gly Arg Val Ser Met Arg Arg
1               5                   10                  15

Asp Thr Leu Arg Glu Val Gln Leu
            20

<210> SEQ ID NO 24
<211> LENGTH: 27
<212> TYPE: PRT
<213> ORGANISM: Artificial Sequence
<220> FEATURE:
<223> OTHER INFORMATION: Completely synthesized in the lab. Peptide
      NE119-145 C122A.

<400> SEQUENCE: 24

Gly Val Gln Ala Leu Ala Met Gly Trp Gly Leu Leu Gly Arg Asn Arg
1               5                   10                  15

Gly Ile Ala Ser Val Leu Gln Glu Leu Asn Val
            20                  25

<210> SEQ ID NO 25
<211> LENGTH: 27
<212> TYPE: PRT
<213> ORGANISM: Artificial Sequence
<220> FEATURE:
<223> OTHER INFORMATION: Completely synthesized in the lab. Peptide
      NE119-145 I136D.

<400> SEQUENCE: 25

Gly Val Gln Cys Leu Ala Met Gly Trp Gly Leu Leu Gly Arg Asn Arg
1               5                   10                  15

Gly Asp Ala Ser Val Leu Gln Glu Leu Asn Val
            20                  25

<210> SEQ ID NO 26
```

```
-continued

<211> LENGTH: 27
<212> TYPE: PRT
<213> ORGANISM: Artificial Sequence
<220> FEATURE:
<223> OTHER INFORMATION: Completely synthesized in the lab. Peptide
      NE119-145 E142R.

<400> SEQUENCE: 26

Gly Val Gln Cys Leu Ala Met Gly Trp Gly Leu Leu Gly Arg Asn Arg
1               5                   10                  15

Gly Ile Ala Ser Val Leu Gln Arg Leu Asn Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: Completely synthesized in the lab. Peptide
      NE119-145 E142L.

<400> SEQUENCE: 27

Gly Val Gln Cys Leu Ala Met Gly Trp Gly Leu Leu Gly Arg Asn Arg
1               5                   10                  15

Gly Ile Ala Ser Val Leu Gln Leu Leu Asn Val
            20                  25

<210> SEQ ID NO 28
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37120-146 C123A.

<400> SEQUENCE: 28

Gly Thr Arg Ala Gln Val Ala Gly Trp Gly Ser Gln Arg Ser Gly Gly
1               5                   10                  15

Arg Leu Ser Arg Phe Pro Arg Phe Val Asn Val
            20                  25

<210> SEQ ID NO 29
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37120-146 Q131W.

<400> SEQUENCE: 29

Gly Thr Arg Cys Gln Val Ala Gly Trp Gly Ser Trp Arg Ser Gly Gly
1               5                   10                  15

Arg Leu Ser Arg Phe Pro Arg Phe Val Asn Val
            20                  25

<210> SEQ ID NO 30
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37120-146 S133R.

<400> SEQUENCE: 30

Gly Thr Arg Cys Gln Val Ala Gly Trp Gly Ser Trp Arg Arg Gly Gly
1               5                   10                  15
```

Arg Leu Ser Arg Phe Pro Arg Phe Val Asn Val
            20                  25

<210> SEQ ID NO 31
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37120-146 R136D.

<400> SEQUENCE: 31

Gly Thr Arg Cys Gln Val Ala Gly Trp Gly Ser Trp Arg Ser Gly Gly
1               5                   10                  15

Asp Leu Ser Arg Phe Pro Arg Phe Val Asn Val
            20                  25

<210> SEQ ID NO 32
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37120-146 R139M.

<400> SEQUENCE: 32

Gly Thr Arg Cys Gln Val Ala Gly Trp Gly Ser Trp Arg Ser Gly Gly
1               5                   10                  15

Arg Leu Ser Met Phe Pro Arg Phe Val Asn Val
            20                  25

<210> SEQ ID NO 33
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37120-146 R142M.

<400> SEQUENCE: 33

Gly Thr Arg Cys Gln Val Ala Gly Trp Gly Ser Trp Arg Ser Gly Gly
1               5                   10                  15

Arg Leu Ser Arg Phe Pro Met Phe Val Asn Val
            20                  25

<210> SEQ ID NO 34
<211> LENGTH: 28
<212> TYPE: PRT
<213> ORGANISM: Artificial Sequence
<220> FEATURE:
<223> OTHER INFORMATION: Completely synthesized in the lab. Peptide
      CG20-47 C29S.

<400> SEQUENCE: 34

Ile Gln Ser Pro Ala Gly Gln Ser Arg Ser Gly Gly Phe Leu Val Arg
1               5                   10                  15

Glu Asp Phe Val Leu Thr Ala Ala His Cys Trp Gly
            20                  25

<210> SEQ ID NO 35
<211> LENGTH: 28
<212> TYPE: PRT
<213> ORGANISM: Artificial Sequence
<220> FEATURE:
<223> OTHER INFORMATION: Completely synthesized in the lab. Peptide

CG20-47 C45S.

<400> SEQUENCE: 35

Ile Gln Ser Pro Ala Gly Gln Ser Arg Cys Gly Gly Phe Leu Val Arg
1               5                   10                  15

Glu Asp Phe Val Leu Thr Ala Ala His Ser Trp Gly
            20                  25

<210> SEQ ID NO 36
<211> LENGTH: 28
<212> TYPE: PRT
<213> ORGANISM: Artificial Sequence
<220> FEATURE:
<223> OTHER INFORMATION: Completely synthesized in the lab. Peptide
      CG20-47 C29S, C45S.

<400> SEQUENCE: 36

Ile Gln Ser Pro Ala Gly Gln Ser Arg Ser Gly Gly Phe Leu Val Arg
1               5                   10                  15

Glu Asp Phe Val Leu Thr Ala Ala His Ser Trp Gly
            20                  25

<210> SEQ ID NO 37
<211> LENGTH: 25
<212> TYPE: PRT
<213> ORGANISM: Artificial Sequence
<220> FEATURE:
<223> OTHER INFORMATION: Completely synthesized in the lab. Peptide
      NE20-44 C26S.

<400> SEQUENCE: 37

Leu Arg Gly Gly His Phe Ser Gly Ala Thr Leu Ile Ala Pro Asn Phe
1               5                   10                  15

Val Met Ser Ala Ala His Cys Val Ala
            20                  25

<210> SEQ ID NO 38
<211> LENGTH: 25
<212> TYPE: PRT
<213> ORGANISM: Artificial Sequence
<220> FEATURE:
<223> OTHER INFORMATION: Completely synthesized in the lab. Peptide
      NE20-44 C42S.

<400> SEQUENCE: 38

Leu Arg Gly Gly His Phe Cys Gly Ala Thr Leu Ile Ala Pro Asn Phe
1               5                   10                  15

Val Met Ser Ala Ala His Ser Val Ala
            20                  25

<210> SEQ ID NO 39
<211> LENGTH: 25
<212> TYPE: PRT
<213> ORGANISM: Artificial Sequence
<220> FEATURE:
<223> OTHER INFORMATION: Completely synthesized in the lab. Peptide
      NE20-44 C26S, C42S.

<400> SEQUENCE: 39

Leu Arg Gly Gly His Phe Ser Gly Ala Thr Leu Ile Ala Pro Asn Phe
1               5                   10                  15

Val Met Ser Ala Ala His Ser Val Ala
            20                  25

-continued

```
<210> SEQ ID NO 40
<211> LENGTH: 25
<212> TYPE: PRT
<213> ORGANISM: Artificial Sequence
<220> FEATURE:
<223> OTHER INFORMATION: Completely synthesized in the lab. Peptide
      CAP3720-44C26S.

<400> SEQUENCE: 40

Asn Gln Gly Arg His Phe Ser Gly Gly Ala Leu Ile His Ala Arg Phe
1               5                   10                  15

Val Met Thr Ala Ala Ser Cys Phe Gln
            20                  25

<210> SEQ ID NO 41
<211> LENGTH: 28
<212> TYPE: PRT
<213> ORGANISM: Artificial Sequence
<220> FEATURE:
<223> OTHER INFORMATION: Completely synthesized in the lab. Peptide
      CG119-144.

<400> SEQUENCE: 41

Gly Thr Leu Cys Thr Val Ala Gly Trp Gly Arg Val Ser Met Arg Arg
1               5                   10                  15

Gly Gly Thr Thr Asp Thr Leu Arg Glu Val Gln Leu
            20                  25

<210> SEQ ID NO 42
<211> LENGTH: 27
<212> TYPE: PRT
<213> ORGANISM: Artificial Sequence
<220> FEATURE:
<223> OTHER INFORMATION: Completely synthesized in the lab. Peptide
      CAP37 120-146.

<400> SEQUENCE: 42

Gly Thr Arg Cys Gln Val Ala Gly Trp Gly Ser Trp Arg Ser Gly Gly
1               5                   10                  15

Arg Leu Ser Met Phe Pro Met Phe Val Asn Val
            20                  25

<210> SEQ ID NO 43
<211> LENGTH: 27
<212> TYPE: PRT
<213> ORGANISM: Artificial Sequence
<220> FEATURE:
<223> OTHER INFORMATION: Completely synthesized in the lab. Peptide
      CG119-144.

<400> SEQUENCE: 43

Gly Thr Leu Cys Thr Val Ala Gly Trp Gly Arg Val Ser Met Arg Arg
1               5                   10                  15

Gly Thr Asp Thr Leu Arg Pro Arg Val Gln Leu
            20                  25

<210> SEQ ID NO 44
<211> LENGTH: 27
<212> TYPE: PRT
<213> ORGANISM: Artificial Sequence
<220> FEATURE:
<223> OTHER INFORMATION: Completely synthesized in the lab. Peptide
      CG119-144.

<400> SEQUENCE: 44

Gly Thr Leu Cys Thr Val Ala Gly Trp Gly Arg Val Ser Met Arg Arg
```

```
1               5                   10                  15
Gly Thr Arg Thr Leu Arg Pro Arg Val Gln Leu
                20                  25

<210> SEQ ID NO 45
<211> LENGTH: 27
<212> TYPE: PRT
<213> ORGANISM: Artificial Sequence
<220> FEATURE:
<223> OTHER INFORMATION: Completely synthesized in the lab. Peptide
      NE119-145

<400> SEQUENCE: 45

Gly Val Gln Cys Leu Ala Met Gly Trp Gly Leu Leu Gly Arg Asn Arg
1               5                   10                  15

Gly Arg Ala Ser Val Leu Gln Glu Leu Asn Val
                20                  25

<210> SEQ ID NO 46
<211> LENGTH: 27
<212> TYPE: PRT
<213> ORGANISM: Artificial Sequence
<220> FEATURE:
<223> OTHER INFORMATION: Completely synthesized in the lab. Peptide
      NE119-145

<400> SEQUENCE: 46

Gly Val Gln Cys Leu Ala Met Gly Trp Gly Leu Leu Gly Arg Asn Arg
1               5                   10                  15

Gly Arg Ala Ser Val Leu Gln Arg Leu Asn Val
                20                  25
```